United States Patent
Valent

(10) Patent No.: US 8,076,321 B2
(45) Date of Patent: Dec. 13, 2011

(54) COMPOSITIONS FOR TREATMENT OF SYSTEMIC MASTOCYTOSIS

(76) Inventor: Peter Valent, Vienna (AT)

( * ) Notice: Subject to any disclaimer, the term of this patent is extended or adjusted under 35 U.S.C. 154(b) by 423 days.

(21) Appl. No.: 11/996,081

(22) PCT Filed: Jul. 19, 2006

(86) PCT No.: PCT/EP2006/064431
§ 371 (c)(1),
(2), (4) Date: May 29, 2008

(87) PCT Pub. No.: WO2007/010014
PCT Pub. Date: Jan. 25, 2007

(65) Prior Publication Data
US 2009/0221550 A1 Sep. 3, 2009

Related U.S. Application Data

(60) Provisional application No. 60/701,098, filed on Jul. 20, 2005.

(51) Int. Cl.
*A61K 31/00* (2006.01)
*A61K 31/553* (2006.01)
*A61K 31/505* (2006.01)

(52) U.S. Cl. ............... 514/211.08; 514/211.09; 514/275

(58) Field of Classification Search .................... 514/341
See application file for complete search history.

(56) References Cited

U.S. PATENT DOCUMENTS 6,545,634 B1 * 4/2003 Heide et al. ............... 342/128
2003/0170720 A1 * 9/2003 van der Kuyl et al. ......... 435/7.1

FOREIGN PATENT DOCUMENTS

| WO | 2005/027971 | 3/2005 |
| WO | 2005/049032 | 6/2005 |
| WO | 2006/135790 | 12/2006 |

OTHER PUBLICATIONS

Pettigrew et al. (Contemporary challenges in mastocytosis, Clin Rev Allergy Immunol. Apr. 2010; 38(2-3): 125-34.*
Kluin-Nelemans Hanneke C et al. "Cladribine Therapy for Systemic Mastocytosis", Blood, vol. 102, No. 13, pp. 4270-4276, (2003).
Shah Neil P et al. "BMS-354825 is a SRC/ABL Inhibitor With High Nanomolar Activity Against The Kit D816V Mutation, Which Drives Systemic Mastocytosis and is Imatinib-Resistant", Blood, vol. 104, No. 11, part 1, pp. 228A, (2004).
Gleixner K V et al. "PKC412 Inhibits In Vitro Growth of Neoplastic Human Mast Cells Expressing the D816V-Mutated Variant of KIT: Comparison with AMN107, Imatinib, and Cladribine (2CdA) and Evaluation of Cooperative Drug Effects", Blood vol. 107, No. 2, pp. 752-759 (2005).
Pardanani et al. "Pathogenesis, Clinical Features and Treatment Advanced in Mastocytosis", Best Practice & Research Clinical Haematology, vol. 19, No. 3, pp. 595-615 (2006).
Barbie D A et al. "Systemic Mastocytosis: Current Classification and Novel Therapeutic Options", Clinical Advanced in Hematology and Oncology 2006 United States, vol. 4, No. 10, pp. 768-775.
Perez-Perez Maria-Jesus et al. "Mitochondrial Thymidine Kinase Inhibitors", Current Topics in Medicinal Chemistry, Bentham Science Publishers, vol. 5, No. 13, pp. 1205-1219 (2005).
Chalandon Y et al. "Targeting Mutated Protein Tyrosine Kinases and Their Signaling Pathways in Hematologic Malignancies", Haematologica 2005 Italy, vol. 90, No. 7, pp. 949-968 (2005).
English Translation of Russian Office Action dated Jul. 21, 2010.

* cited by examiner

*Primary Examiner* — ShengJun Wang
*Assistant Examiner* — Timothy E Betton
(74) *Attorney, Agent, or Firm* — George R. Dohmann

(57) ABSTRACT

The present invention relates to the use of the combination of tyrosine phosphate inhibitors AMN107 and PKC412 for the preparation of a drug for the treatment of a mast cell-related proliferative disease. The present invention is also drawn to a combination treatment of a tyrosine phosphate inhibitor and a TK-inhibitor that is effective against a mast cell-related proliferative disease, including especially systemic mastocytosis (SM) including aggressive SM (ASM) and mast cell leukemia (MCL).

15 Claims, 24 Drawing Sheets

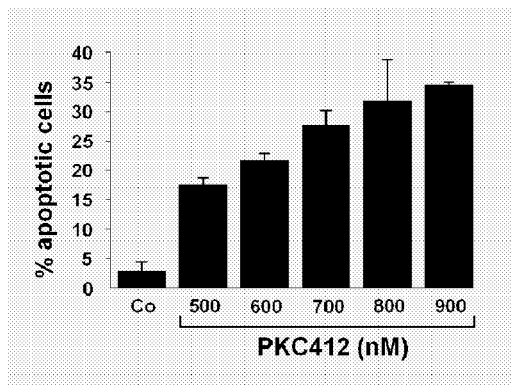
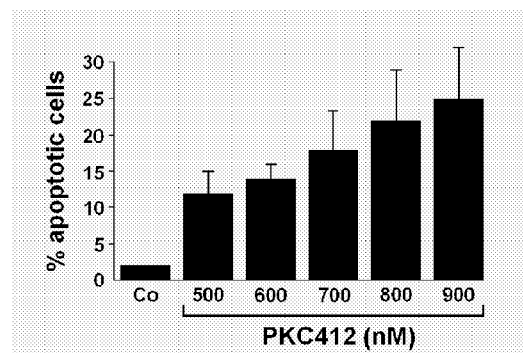
Figure 5A
Figure 5B
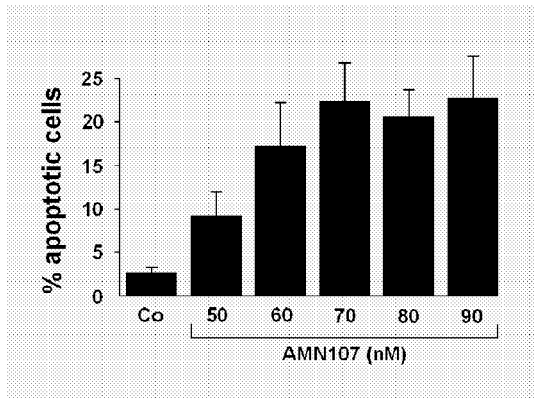
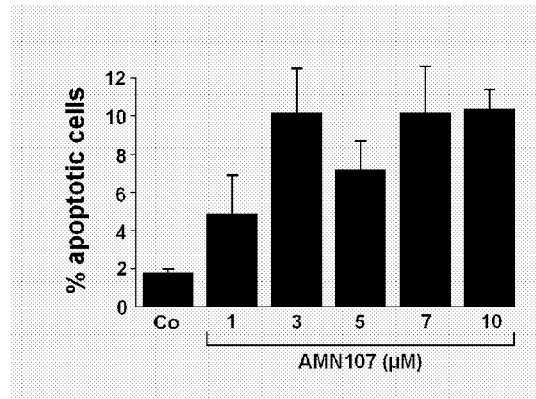
Figure 5C
Figure 5D
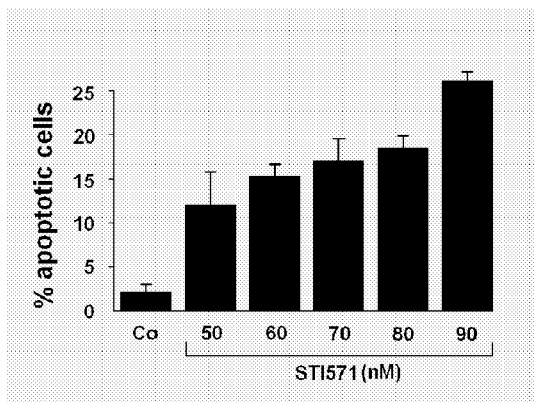
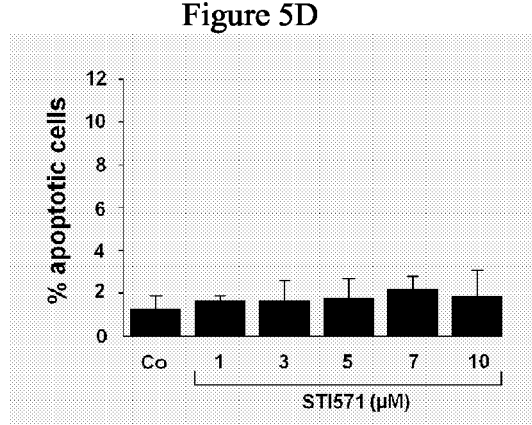
Figure 5E
Figure 5F

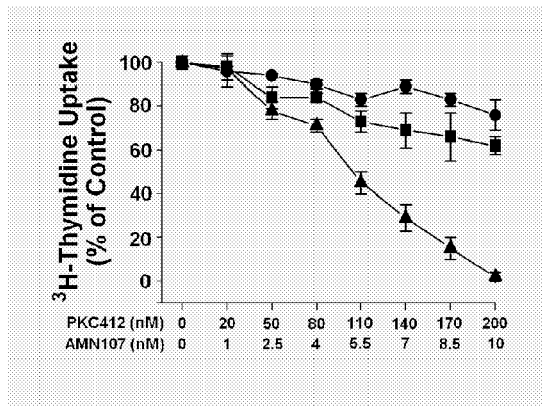 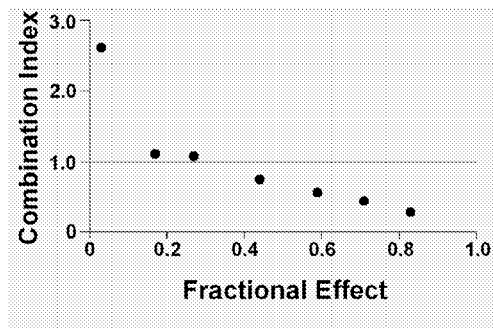
Figure 10A   Figure 10B
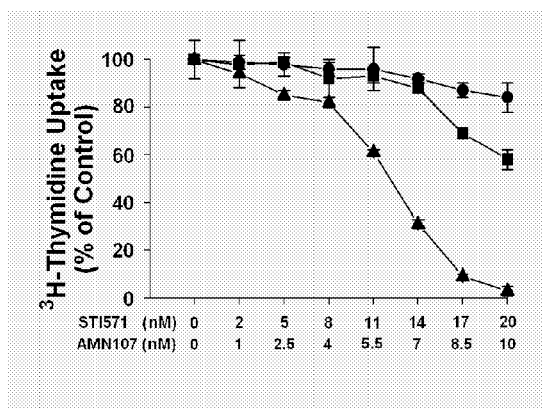 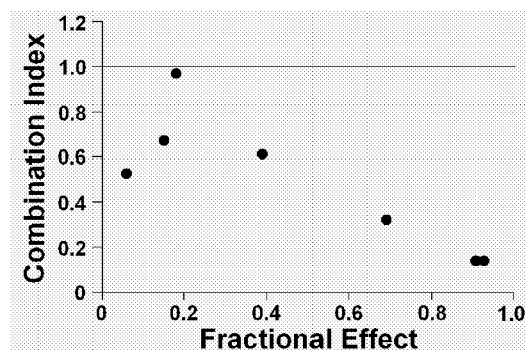
Figure 10C   Figure 10D
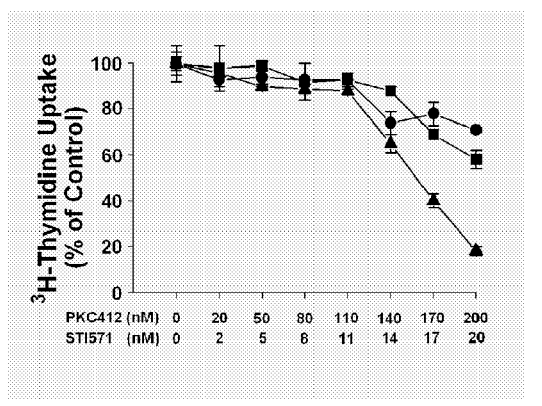 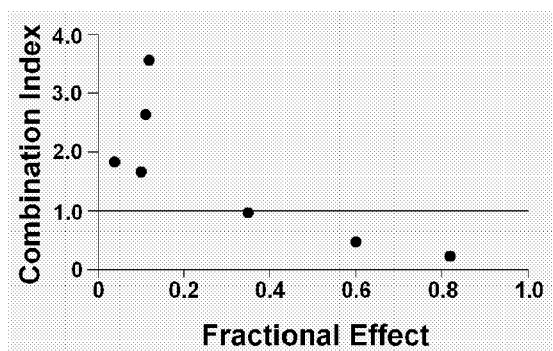
Figure 10E   Figure 10F

COMPOSITIONS FOR TREATMENT OF SYSTEMIC MASTOCYTOSIS

This application claims benefit of U.S. Provisional Application No. 60/701,098, filed Jul. 20, 2005, which in its entirety is herein incorporated by reference.

FIELD OF THE INVENTION

The present invention relates to the use of tyrosine kinase inhibitors for the preparation of a drug for the treatment of systemic mastocytosis. The present invention also relates to a method of treating systemic mastocytosis.

BACKGROUND OF THE INVENTION

Systemic mastocytosis (SM) can be classified into indolent SM (little or no evidence of impaired organ function), aggressive SM (presence of impaired organ function), SM associated hematologic non-mast cell disease (SM-AHNMD) and mast cell leukemia. Clinical presentation in adult SM is heterogenous and includes skin disease (usually urticaria pigmentosa), mast cell mediator-release symptoms (headache, flushing, lightheadedness, syncope, anaphylaxis, etc), and direct or indirect organ damage (bone pain from lytic bone lesions, osteoporosis or bone fractures, hepatosplenomegaly, cytopenia from bone marrow involvement). In addition, around 20% of patients with SM may display significant and sometimes isolated blood eosinophilia (Tefferi and Pardanani 2004).

In general, mast cell leukemia is a terminal disease with survival measured in months and no effective therapy to date. The natural history of indolent SM is far better with median survival measured in decades and infrequent progression to aggressive SM and SM-AHNMD. Outcome in SM-AHNMD is determined by the associated AHNMD and is significantly worse than SM without AHNMD. In both indolent and aggressive SM without AHNMD, increased bone marrow mast cell and eosinophil content, elevated serum alkaline phosphatase, anemia, and hepatosplenomegaly have been associated with poor prognosis (Tefferi and Pardanani 2004). Complete histologic and clinical remission has been achieved in patients with SM associated with the FIP1L1-PDGFRα gene fusion when treated with Gleevec® (Pardanani 2003a, Pardanani 2003b).

SUMMARY OF THE INVENTION

Several emerging treatment concepts for myeloid neoplasms are based on novel drugs targeting critical tyrosine kinases (TK) or downstream signaling molecules.[1-5] Systemic mastocytosis (SM) is a hematopoietic neoplasm that behaves as an indolent myeloproliferative disease in most patients, but can also present as an aggressive disease (aggressive SM is denoted herein as "ASM") or even as a leukemia, e.g., mast cell leukemia (denoted herein as "MCL").[6-11] In patients with ASM and MCL, the response to conventional therapy is poor in most cases, and the prognosis is grave.[6-12] Therefore, a number of attempts have been made to identify novel targets of therapy in neoplastic mast cells (MC) and to define new treatment strategies for these patients.[9-12]

In a majority of all patients with SM including those who are diagnosed to have ASM or MCL, the somatic c-KIT point mutation D816V (Asp816Val) is detectable in neoplastic (mast) cells.[13-17] This point mutation is associated with ligand-independent phosphorylation and activation of KIT, and autonomous differentiation and growth of affected cells.[17,18] Based on this association with constitutive tyrosine kinase (TK) activity, the D816V-mutated variant of KIT is an attractive target of therapy.[9-12,19]

A number of efforts have been made in recent years to identify suitable drugs that would inhibit the TK-activity of KIT D816V.[9-12,19-24] The TK inhibitor imatinib (STI571) that is widely used in clinical hematology, has recently been found to counteract growth of neoplastic MC exhibiting wild type (wt) KIT or the rarely occurring F522C-mutated variant of KIT.[20-23] In addition, this drug is found to block the growth of neoplastic cells in patients who have SM associated with clonal eosinophilia and a FIP1L1/PDGFRA fusion gene (SM with associated chronic eosinophilic leukemia, denoted herein as "SM-CEL").[24-26] However, imatinib failed to inhibit growth of neoplastic MC harbouring the c-KIT mutation D816V[20-22] which points to the clear need to further search for novel TK inhibitors that block KIT D816V and thus growth of neoplastic MC in SM.

The novel TK-targeting drugs PKC412 and AMN107 counteract TK-activity of D816V-KIT and inhibit growth of neoplastic human MC and Ba/F3 cells with doxycycline-inducible expression of KIT-D816V, growth of primary neoplastic mast cells, and growth of the human MCL line HMC-1, which harbours this c-KIT mutation. PKC412 is found to be a superior drug with $IC_{50}$ values of 50-250 nM and without differences seen between HMC-1 cells exhibiting or lacking KIT-D816V. By contrast, AMN107 exhibits more potent effects in KIT-D816V-negative HMC-1 cells. Corresponding results are obtained with Ba/F3 cells exhibiting wild-type or D816V-mutated KIT. The growth-inhibitory effects of PKC412 and AMN107 on HMC-1 are associated with induction of apoptosis and downregulation of CD2 and CD63. PKC412 is found to cooperate with AMN107, imatinib, and cladribine (i.e., 2CdA) in producing growth-inhibition in HMC-1. We also show that PKC412 synergizes with AMN107 and cladribine (2CdA) in producing growth inhibition in HMC-1 cells. Together, PKC412 and AMN107 represent promising novel agents for targeted therapy of SM.

This invention is drawn to a combination treatment of PKC412 and AMN107 that is effective against SM, especially SM associated with the oncogenic c-KIT mutation D816V. This invention is also drawn to a combination treatment of PKC412 and a TK-inhibitor that is effective against SM, especially systemic mastocytosis (SM) including aggressive SM (ASM) and mast cell leukemia (MCL). In a preferred embodiment, SM, ASM and MCL are associated with the oncogenic c-KIT mutation, including especially D816V.

BRIEF DESCRIPTION OF THE DRAWINGS

FIG. 1A,B: KIT phosphorylation in HMC-1.1 cells (FIG. 1A) and HMC-1.2 cells (exhibiting KIT D816V; FIG. 1B) after incubation in control medium (Control), imatinib STI571 (1 μM), PKC412 (1 μM), or AMN107 (1 μM) for 4 hours. FIG. 1C,D: KIT phosphorylation in Ton.Kit.wt cells (FIG. 1C) and Ton.Kit.D816V.27 cells (FIG. 1D) after incubation in control medium (Control), imatinib (i.e., STI571) (1 μM), PKC412 (1 μM), or AMN107 (1 μM) for 4 hours. Prior to drug exposure, Ton.Kit.wt cells and Ton.Kit.D816V.27 cells are kept in doxycycline, 1 μg/ml for 24 hours to induce expression of KIT. In case of the Ton.Kit.wt clone, cells are also exposed to SCF (100 ng/ml, 4 hours) to induce KIT phosphorylation (p-KIT). In all cells, immunoprecipitation is conducted using the anti-KIT mAb SR-1. Western blotting is performed using anti-phospho-mAb 4G10 for p-KIT detection and the anti-KIT mAb 1C1 for detection of total KIT protein.

FIG. 2A: Time-dependent effects of PKC412 on $^3$H-thymidine uptake in HMC-1.2 cells. HMC-1.2 cells are incubated with control medium or PKC412 (300 nM) at 37° C. and 5% $CO_2$ for various time periods as indicated. After incubation, $^3$H-thymidine uptake is analyzed. Results are expressed as percent of control (i.e., $^3$H-thymidine uptake in control medium at each time point) and represent the mean±S.D. of triplicates. FIG. 2B-D: Dose-dependent effects of TK inhibitors on $^3$H-thymidine uptake in HMC-1 cells. HMC-1.1 cells (●-●) and HMC-1.2 cells (■-■) are incubated in control medium in the absence (0) or presence of various concentrations of either PKC412 (FIG. 2B), AMN107 (FIG. 2C), or imatinib (FIG. 2D) at 37° C. for 48 hours. After incubation, $^3$H-thymidine uptake is measured. Results are expressed as percent of control (0, 100%) and represent the mean±S.D. from at least 3 independent experiments.

FIG. 3A: Ton.Kit.wt cells are kept in control medium (open bars) or are induced to express activated wt KIT by adding doxycycline (1 μg/ml) and SCF (black bars). In both conditions, cells are exposed to either control medium (Co) or various concentrations of PKC412, AMN107, or imatinib (STI571), as indicated, for 48 hours (37° C., 5% $CO_2$). Thereafter, $^3$-thymidine uptake is assessed as described in the text. Results are expressed as percent of control (Co) and represent the mean±S.D. from three independent experiments. FIG. 3B: Ton.Kit.D816V.27 cells are kept in control medium (open bars) or are induced to express KIT D816V by adding doxycycline (1 μg/ml) (black bars), and then are exposed to either control medium (Co) or various concentrations of PKC412, AMN107, or imatinib (STI571), as indicated, for 48 hours (37° C., 5% $CO_2$). Thereafter, $^3$H-thymidine uptake is determined. Results are expressed as percent of control (cells exposed to control medium, denoted herein as "Co") and represent the mean±S.D. from three independent experiments.

FIG. 5A-F is a graphic representation of the effects of TK inhibitors on apoptosis of HMC-1 cells. HMC-1.1 cells (FIG. 5A,C,E) and HMC-1.2 cells (FIG. 5B,D,F) are cultured in the absence (Co) or presence of various concentrations of PKC412 (FIG. 5A,B), AMN107 (FIG. 5C,D), or imatinib (FIG. 5E,F) as indicated at 37° C. for 24 hours. Thereafter, the percentages of apoptotic cells are quantified by light microscopy. Results represent the mean±S.D. of three independent experiments.

FIG. 9A: HMC-1.2 cells are exposed to control medium (Co, open bars), PKC412, 1 μM (black bars), AMN107, 1 μM (hatched bars), or imatinib (i.e., STI157), 1 μM (grey bars) at 37° C. for 24 hours. Results show the percent of control and represent the mean±S.D. of 3 independent experiments. FIG. 9B: Dose-dependent effect of PKC412 on expression of CD63 on HMC-1.2 cells. Cells are incubated with various concentrations of PKC412 as indicated at 37° C. for 24 hours. Thereafter, cells are harvested and examined for expression of CD63 by flow cytometry. The figure shows a typical result from one experiment. As visible, PKC412 dose-dependently decreased expression of CD63.

FIG. 10A-J is a graphic representation of the synergistic drug effects on growth of HMC-1 cells. HMC-1.1 cells lacking KIT D816V (FIG. 10A-F) and HMC-1.2 cells exhibiting KIT D816V (FIG. 10G-J) are incubated with control medium (0) or various combinations of drugs (in fixed ratio) as indicated, at 37° C. for 48 hours to determine cooperative antiproliferative effects. FIG. 10A,C,E,G,I: After incubation with single drugs (FIG. 10A: PKC412, ■-■; AMN107, ●-●; FIG. 10C: STI571, ■-■; AMN107, ●-●; FIG. 10E: STI571, ■-■; PKC412, ●-●; FIG. 10G: PKC412, ■-■; AMN107, ●-●; FIG. 10I: PKC412, ■-■; 2CdA, ●-●) or drug combinations (▲-▲), cells are analyzed for uptake of $^3$H-thymidine. Results show $^3$H-thymidine uptake as percentage of control (medium control, denoted as "0" or as "100%") and represent the mean±S.D. of triplicates from one typical experiment (corresponding results are obtained in at least 2 other experiments for each drug combination). Images in the right (FIG. 10B,D,F,H,J) show combination index values determined for each fraction affected according to the method of Chou and Talalay[39] using calcusyn software. A combination index (CI) value of 1.0 indicates an additive effect, a CI greater than 1.0 indicates antagonism, and a CI of less than 1.0 indicates synergism.

FIGS. 11A,B represent tyrosine phosphorylation of KIT in HMC-1.1 cells (FIG. 11A) and HMC-1.2 cells (exhibiting KIT D816V) (FIG. 11B) after incubation in control medium or various concentrations of dasatinib for 4 hours. FIGS. 11C,D represent KIT-phosphorylation in doxycycline-exposed Ton. Kit.wt cells (FIG. 11C) and Ton.Kit.D816V.27 cells (FIG. 11D) after incubation in control medium (0) or dasatinib ($10^{-3}$-$10^3$ nM) for 4 hours. Prior to drug exposure, Ton.Kit.wt cells and Ton.Kit.D816V.27 cells were kept in control medium (control), or in doxycycline for 24 hours to induce expression of KIT. In case of Ton.Kit.wt, cells were also exposed to SCF (100 ng/ml, 4 hours) to induce KIT phosphorylation (p-KIT). In all cells, immunoprecipitation was conducted using the anti-KIT mAb 1C1. Western blotting was performed using the anti-phospho-tyr-mAb 4G10 for p-KIT detection and the anti-KIT mAb 1C1 for detection of total KIT protein (KIT).

FIG. 12A represents time-dependent effects of dasatinib on $^3$H-thymidine uptake in HMC-1.1 cells (■-■) and HMC-1.2 cells (●-●). HMC-1.1 cells were incubated with dasatinib at 10 nM, and HMC-1.2 cells with dasatinib at 1 μM, at 37° C. and 5% $CO_2$ for various time periods as indicated. After incubation, $^3$H-thymidine uptake was measured. Results are expressed as percent of control (=$^3$H-thymidine uptake in cells kept in control medium) and represent the mean±S.D. of 3 independent experiments. FIG. 12B represents dose-dependent effects of dasatinib on $^3$H-thymidine uptake in HMC-1.1 cells (■-■) and HMC-1.2 cells (●-●). Cells were incubated in control medium in the absence or presence of various concentrations of dasatinib at 37° C. for 48 hours. After incubation, $^3$H-thymidine uptake was measured. Results are expressed as percent of control and represent the mean±S.D. from 3 independent experiments. (FIG. 12C) Effects of dasatinib on growth of Ton.Kit.wt cells. Cells were either maintained in IL-3-containing medium before and during incubation with dasatinib (●-●) or were preincubated with doxycycline (1 μg/ml) in the presence of IL-3 for 24 hours, and then were incubated with various concentrations of dasatinib in medium containing doxycycline and SCF (100 ng/ml) without IL-3 for 48 hours at 37° C. (■-■). After incubation, cells were harvested and subjected to $^3$H-thymidine uptake experiments. Results are expressed as percent of control and represent the mean±S.D. of 3 independent experiments. (FIG. 12D) Effects of dasatinib on growth of Ton.Kit.D816V cells. Cells were incubated in control medium (+IL-3) and various concentrations of dasatinib (as indicated) in the absence (●-●) or presence (■-■) of doxycycline (1 μg/ml) for 48 hours (37° C.). Thereafter, cell viability was determined by the trypan blue exclusion test. Results are expressed as percent of viable cells (calculated from the percentage of trypan blue positive cells) compared to control (without dasatinib=100%) and represent the mean±S.D. of 3 independent experiments. (FIG. 12E,F) Effects of dasatinib (FIG. 12E) and AMN107 (FIG. 12F) on KIT-D816V-induced cluster formation in Ton.Kit.D816V.27 cells. Cells were incubated without doxycycline (Co) or in doxycycline (1 μg/ml) in the absence or presence of various concentrations of dasatinib or AMN107 as indicated for 24 hours. After incubation, the numbers of clusters were counted under an inverted microscope. Results are expressed as percentage of cluster formation compared to cells kept in control medium (Co) and doxycycline (=100%) and represent the mean±S.D. of 3 independent experiments.

(FIG. 14A,B) HMC-1.1 cells (FIG. 14A) and HMC-1.2 cells (FIG. 14B) were cultured in the absence (Co) or presence of various concentrations of dasatinib as indicated for 24 hours. Thereafter, the percentages of apoptotic cells were quantified by light microscopy. Results represent the mean±S.D. of three independent experiments. Asterisk indicates p<0.05. (FIG. 14C) Electron microscopic examination of dasatinib-induced apoptosis in HMC-1.1 cells and HMC-1.2 cells. HMC-1 cells were incubated with control medium or dasatinib (1 μM) at 37° C. for 24 hours. Then, cells were harvested and analyzed for ultrastructural signs of apoptosis. Whereas apoptotic cells were rarely seen in cultures kept in control medium, most HMC-1 cells cultured in dasatinib displayed signs of apoptosis including cell shrinkage, membrane ruffling, vacuolization, and condensation of the nuclear chromatin. (FIG. 14D,E) Dasatinib-induced apoptosis in HMC-1 cells assessed by Tunel assay. HMC-1.1 cells (FIG. 14D) and HMC-1.2 cells (FIG. 14E) were incubated in control medium, various concentrations of dasatinib (as indicated), or PKC412 (100 nM and 1 μM) as indicated at 37° C. for 24 hours. Thereafter, cells were harvested and subjected to Tunel assay. As visible, dasatinib produced dose-dependent apoptosis in HMC-1.1 and HMC-1.2 cells.

(FIG. 15A) HMC-1.1 cells and HMC-1.2 cells (FIG. 15B) were exposed to control medium or various concentrations of dasatinib (as indicated) or PKC412 (1 μM) at 37° C. for 24 hours. After incubation, cells were examined for expression of various CD antigens by flow cytometry using CD-specific mAbs. FIGS. 15C-D shows the mean fluorescence intensity (MFI) levels as percent of control (=100%). Results represent the mean±S.D. of 3 independent experiments. Asterisk: p<0.05. (FIG. 15E,F) Expression of CD63 on HMC-1.1 cells (FIG. 15E) and HMC-1.2 cells (FIG. 15F) after incubation in control medium, various concentrations of dasatinib, or PKC412 (1 μM) at 37° C. for 24 hours. Flow cytometry was performed with the CD63 mAb CLB-gran12 (black line). The dashed line represents the isotype-matched control antibody. (FIG. 16A) HMC-1.1 were incubated with various concentrations of dasatinib (■-■) or PKC412 (●-●), or combinations of both drugs (▼-▼). (FIG. 16B) HMC-1.1 were incubated with various concentrations of dasatinib (●-●) or imatinib (■-■), or combinations of both drugs (▲-▲). (FIG. 16C) HMC-1.2 cells were incubated with various concentrations of dasatinib (■-■) or PKC412 (●-●), or with combinations of both drugs (▲-▲). (FIG. 16D) HMC-1.2 cells were incubated with various concentrations of dasatinib (■-■) or 2CdA (●-●), or with combinations of both drugs (▲-▲). Results represent the mean±S.D. of triplicates from one typical experiment. As assessed by the calcusyn program, drug interactions (FIG. 16A-D) were found to be synergistic in nature.

DETAILED DESCRIPTION

Figure 1A:
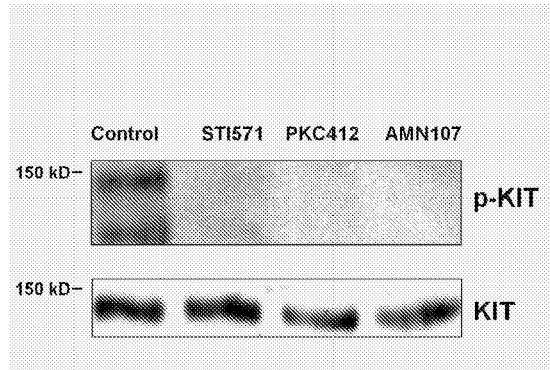
FIG. 1A-D is a representation of the effects of TK inhibitors on KIT phosphorylation in neoplastic cells.

The problem to be solved by the present invention is the use of a combination of PKC412 and AMN107 in the treatment of systemic mastocytosis, especially SM associated with the oncogenic c-KIT mutation D816V.

In a majority of all patients with systemic mastocytosis (SM), including aggressive SM and mast cell leukemia (MCL), neoplastic cells express the oncogenic c-KIT mutation D816V. This mutation activates the tyrosine kinase (TK) of the KIT receptor, which thus represents an attractive target of therapy. However, most of the available TK-inhibitors including STI571 (imatinib; Novartis Pharma AG), fail to block TK-activity of KIT D816V at pharmacologic concentrations. We provide evidence that the novel TK-targeting drugs PKC412 and AMN107 (Novartis) block TK-activity of D816V-mutated KIT and counteract growth of Ba/F3 cells with doxycycline-induced expression of KIT D816V as well as growth of the human mast cell leukemia cell line HMC-1 expressing this c-KIT mutation. PKC412 is found to be the more potent agent with IC50 values of 50-200 nM and without differences seen between HMC-1 cells exhibiting or lacking KIT D816V. By contrast, AMN107 exhibited potent effects only in the absence of KIT D816V in HMC-1 cells (IC$_{50}$ 5-10 nM compared to KIT D816V-expressing HMC-1: IC$_{50}$ 1-5 µM). Corresponding results are obtained with Ba/F3 cells exhibiting wild-type or the D816V-mutated variant of KIT.

Subsequently, the effect of PKC412 on primary neoplastic MC obtained from the bone marrow of a patient with SM exhibiting KIT D816V are examined. In line with our cell line data, PKC412 dose-dependently inhibited $^3$H-thymidine uptake in neoplastic MC (IC$_{50}$: 50 nM) in this patient, whereas no significant effects are found with AMN107 (0.1-3 µM) and imatinib (1 µM). The growth-inhibitory effects of PKC412 and AMN107 on HMC-1 cells are associated with TK-inhibition of KIT in phosphoblot experiments, and with induction of apoptosis as assessed by conventional morphology and by electron microscopy. In addition, PKC412 is found to down-regulate expression of CD2 and CD63 (two cell surface antigens up-regulated in SM) on HMC-1 cells. In co-incubation experiments, PKC412 is found to synergize with AMN107, imatinib, and cladribine (2CdA) in producing growth inhibition in HMC-1 cells harbouring KIT D816V as well as in HMC-1 cells lacking KIT D816V. In summary, our data show that PKC412 and AMN107 alone and in combination counteract growth of neoplastic mast cells expressing the D816V-mutated variant of KIT. Both drugs may therefore be considered as novel promising agents for targeted therapy in patients with aggressive SM and MCL.

Therefore, the present invention relates to the use of N-[(9S,10R,11R,13R)-2,3,10,11,12,13-hexahydro-10-methoxy-9-methyl-1-oxo-9,13-epoxy-1H,9H-diindolo[1,2,3-gh: 3',2',1'-1m]pyrrolo[3,4-j][1,7]benzodiazonin-11-yl]-N-methylbenzamide of formula (I) (hereinafter: "PKC412"):

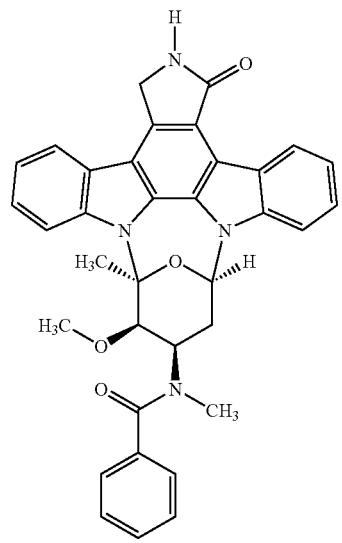

(I)

in combination with 4-Methyl-3-[[4-(3-pyridinyl)-2-pyrimidinyl]amino]-N-[5-(4-methyl-1H-imidazol-1-yl)-3-(trifluoromethyl)phenyl]benzamide of formula (II) (hereinafter: "AMN107"):

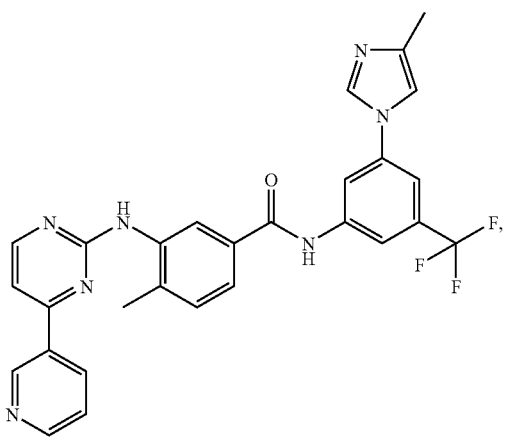

(II)

or a pharmaceutically acceptable salt of either or both, for treatment of systemic mastocytosis.

Abbreviations used herein preferably have within the context of this disclosure the following meanings, unless otherwise indicated:

| | |
|---|---|
| ASM | aggressive systemic mastocytosis |
| bm | bone marrow |
| cladribine | 2-chlorodeoxyadenosine |
| FCS | fetal calf serum |
| IFNα | interferon-alpha |
| IP | immunoprecipitation |
| MCL | mast cell leukemia |
| PBS | phosphate-buffered saline |
| PE | phycoerythrin |
| rh | recombinant human |
| RT | room temperature |
| SCF | stem cell factor |
| SM | systemic mastocytosis |

| | |
|---|---|
| SSM | smouldering systemic mastocytosis |
| TK | tyrosine kinase |
| wt | wild type |

The general terms used herein preferably have within the context of this disclosure the following meanings, unless otherwise indicated:

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula I and formula II.

Salts are especially the pharmaceutically acceptable salts of compounds of formula I and formula II. Compounds of formula I and formula II may be administered sequentially or concurrently. Compounds of formula I and formula II may be combined in a single formulation or be in separate formulations.

Such salts are formed, for example, as acid addition salts, preferably with organic or inorganic acids, from compounds of formula I and/or formula II with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, dodecylsulfuric acid, 2-, 3- or 4-methylbenzenesulfonic acid, methylsulfuric acid, ethylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I and/or formula II may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

In each case where citations of patent applications or scientific publications are given, the subject-matter of the final products, the pharmaceutical preparations and the claims are hereby incorporated into the present application by reference to these publications. If any discrepancy appears between statements in an incorporated reference and the present disclosure, then statements in the present disclosure shall govern.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

It has now surprisingly been found that the combination of AMN107 and PKC412 possesses therapeutic properties, which render it particularly useful as an inhibitor of tyrosine kinase activity and especially for the treatment and prophylaxis of oncogenic KIT-D816V-induced diseases such as systemic mastocytosis.

KIT-D816V, as used hereinbefore and hereinafter, is the designation of the mutation product of the c-Kit gene wherein the nucleic acid encoding the aspartic acid at residue 816 of the KIT polypeptide is mutated to encode a valine. KIT-D816V also refers to the polypeptide product of the mutated oncogenic c-KIT gene.

The present invention thus concerns the use of the combination of AMN107 and PKC412 for the preparation of a drug for the treatment of oncogenic c-KIT mutation D816V induced systemic mastocytosis, or other diseases associated with the oncogenic c-KIT mutation D816V or similar mutations that activate tyrosine kinase.

Systemic Mastocytosis (SM) includes indolent SM, aggressive SM, and SM associated hematologic non-mast cell disease and mast cell leukemia.

The term "mastocytosis" as used herein, relates to systemic mastocytosis, for example mastocytoma, and also to canine mast cell neoplasms. Mastocytosis is a myelo-proliferative disorder with limited treatment options and generally a poor prognosis. The pathogenesis of mastocytosis has been attributed to constitutive activation of the receptor tyrosine kinase KIT. In a large majority of mastocytosis patients, the deregulated tyrosine kinase activity of KIT is due to a mutation within the codon 816 of the protein (D816V) which also confers resistance to imatinib or imatinib mesylate, the latter being marketed as Gleevec® in the United States or Glivec® elsewhere, in vitro and in vivo.

Mast cells play an important role as the primary effector cells in the allergic disorders mentioned herein. Antigen-specific IgE-mediated degranulation of mast cells leads to the subsequent release of chemical mediators and multiple cytokines and to leukotriene synthesis. Furthermore, mast cells are involved in the pathogenesis of multiple sclerosis.

Mast cell neoplasms occur in both humans and animals. In dogs, mast cell neoplasms are called mastocytomas, and the disease is common, representing 7%-21% of canine tumors. A distinction must be drawn between human mastocytosis, which is usually transient or indolent, and canine mast cell neoplasia, which behaves unpredictably and is often aggressive and metastatic. For instance, human solitary mastocytomas do not often metastasize; in contrast, 50% of canine mastocytomas behave in a malignant fashion, as estimated by Hottendorf & Nielsen (1969) after review of 46 published reports of tumors in 938 dogs.

The KIT receptor's involvement in the pathogenesis of mastocytosis is suggested by the observation that several mutations resulting in constitutive activation of KIT have been detected in a number of mast cell lines. For instance, a point mutation in human c-KIT, causing substitution of Val for Asp816 in the phosphotransferase domain and receptor autoactivation, occurs in a long-term human mast cell leukemia line (HMC-1) and in the corresponding codon in two rodent mast cell lines. Moreover, this activating mutation has been identified in situ in some cases of human mastocytosis. Two other activating mutations have been found in the intracellular juxtamembrane region of KIT, i.e., the Val560Gly substitution in the human HMC-1 mast cell line, and a seven amino acid deletion (Thr573-His579) in a rodent mast cell line called FMA3.

The present invention more particularly concerns the use of the combination of AMN107 and PKC412 for the preparation of a drug for the treatment of systemic mastocytosis.

In another embodiment, the instant invention provides a method for treating systemic mastocytosis comprising administering to a mammal in need of such treatment a therapeutically effective amount of the combination of AMN107 and PKC412, or pharmaceutically acceptable salts or pro-drugs thereof.

Preferably the instant invention provides a method for treating mammals, especially humans, suffering from systemic mastocytosis comprising administering to a mammal in need of such treatment a KIT-D816V inhibiting amount of the combination of AMN107 and PKC412 or pharmaceutically acceptable salts thereof.

In the present description, the term "treatment" includes both prophylactic or preventative treatment as well as curative or disease suppressive treatment, including treatment of patients at risk of contracting the disease or suspected to have contracted the disease as well as ill patients. This term further includes the treatment for the delay of progression of the disease.

The term "curative" as used herein means efficacy in treating ongoing episodes involving systemic mastocytosis.

The term "prophylactic" means the prevention of the onset or recurrence of diseases involving systemic mastocytosis.

The term "delay of progression" as used herein means administration of the active compound to patients being in a pre-stage or in an early phase of the disease to be treated, in which patients for example a pre-form of the corresponding disease is diagnosed or which patients are in a condition, e.g. during a medical treatment or a condition resulting from an accident, under which it is likely that a corresponding disease will develop.

This unforeseeable range of properties means that the use of the combination of AMN107 and PKC412 are of particular interest for the manufacture of a medicament for the treatment of systemic mastocytosis.

This effect can especially be clinically relevant for patients with systemic mastocytosis.

To demonstrate that the combination of AMN107 and PKC412 is particularly suitable for the treatment of systemic mastocytosis with good therapeutic margin and other advantages, clinical trials can be carried out in a manner known to the skilled person.

The precise dosage of the combination of AMN107 and PKC412 to be employed for inhibiting systemic mastocytosis depends upon several factors including the host, the nature and the severity of the condition being treated, the mode of administration. The combination of AMN107 and PKC412 can be administered either together or independently by any route, including orally, parenterally, e.g., intraperitoneally, intravenously, intramuscularly, subcutaneously, intratumorally, or rectally, or enterally. Preferably the combination of AMN107 and PKC412 is administered orally, preferably at a daily dosage of 1-300 mg/kg body weight or, for most larger primates, a daily dosage of 50-5000, preferably 500-3000 mg. A preferred oral daily dosage is 1-75 mg/kg body weight or, for most larger primates, a daily dosage of 10-2000 mg, administered as a single dose or divided into multiple doses, such as twice daily dosing.

The precise dosage of PKC412 administered in combination with AMN107 depends upon several factors including the host, the nature and the severity of the condition being treated, the mode of administration. However, in general, satisfactory results are achieved when PKC412 is administered parenterally, e.g., intraperitoneally, intravenously, intramuscularly, subcutaneously, intratumorally, or rectally, or enterally, e.g., orally, preferably intravenously or, preferably orally, intravenously at a daily dosage of 0.1 to 10 mg/kg body weight, preferably 1 to 5 mg/kg body weight. In human trials a total dose of 225 mg/day is most presumably the Maximum Tolerated Dose (MTD). A preferred intravenous daily dosage is 0.1 to 10 mg/kg body weight or, for most larger primates, a daily dosage of 200-300 mg. A typical intravenous dosage is 3 to 5 mg/kg, three to five times a week.

Most preferably, PKC412 is administered orally, by dosage forms such as microemulsions, soft gels or solid dispersions in dosages up to about 250 mg/day, in particular 225 mg/day, administered once, twice or three times daily.

Usually, a small dose is administered initially and the dosage is gradually increased until the optimal dosage for the host under treatment is determined. The upper limit of dosage is that imposed by side effects and can be determined by trial for the host being treated.

Combinations of AMN107 and PKC412 may be combined, independently or together, with one or more pharmaceutically acceptable carriers and, optionally, one or more other conventional pharmaceutical adjuvants and administered enterally, e.g. orally, in the form of tablets, capsules, caplets, etc. or parenterally, e.g., intraperitoneally or intravenously, in the form of sterile injectable solutions or suspensions. The enteral and parenteral compositions may be prepared by conventional means.

The combination of AMN107 and PKC412 can be used alone or combined with at least one other pharmaceutically active compound for use in these pathologies. These active compounds can be combined in the same pharmaceutical preparation or in the form of combined preparations "kit of parts" in the sense that the combination partners can be dosed independently or by use of different fixed combinations with distinguished amounts of the combination partners, i.e., simultaneously or at different time points. The parts of the kit of parts can then, e.g., be administered simultaneously or chronologically staggered, that is at different time points and with equal or different time intervals for any part of the kit of parts. Non-limiting examples of compounds which can be cited for use in combination with the combination of AMN107 and PKC412 are cytotoxic chemotherapy drugs, such as cytosine arabinoside, daunorubicin, doxorubicin, cyclophosphamide, VP-16, or imatinib etc. Further, the combination of AMN107 and PKC412 could be combined with other inhibitors of signal transduction or other oncogene-targeted drugs with the expectation that significant synergy would result.

The invention further pertains to the combination of AMN107 and PKC412 as described herein with imatinib for the treatment of the diseases and conditions described herein. The administration of such a combination may be affected at the same time, for instance in the form of a fixed, combined pharmaceutical composition or preparation, or sequentially or timely staggered. The administration of the combination of AMN107 and PKC412 in a dosage form as described herein and of imatinib in its marketed form of GLEEVEC® in the US (GLIVEC® in Europe) and with the dosages envisaged for these dosage forms is currently preferred.

The treatment of systemic mastocytosis with the above combination may be a so-called first line treatment, i.e., the treatment of a freshly diagnosed disease without any preceding chemotherapy or the like, or it may also be a so-called second line treatment, i.e., the treatment of the disease after a preceding treatment with imatinib or the combination of AMN107 and PKC412, depending on the severity or stage of the disease as well as the over all condition of the patient etc.

The efficacy of the combination of AMN107 and PKC412 for the treatment of systemic mastocytosis is illustrated by the results of the following examples. These examples illustrate the invention without in any way limiting its scope.

EXAMPLES

Example 1

Clinical Study

The effect of Compound (II) on c-KIT transcript levels and mutation status of c-kit in malignant cells taken from the blood and/or bone marrow is assessed. SM may result from altered kinase activity. SM associated with c-Kit D816V may also result from an activating mutation in the KIT gene. Q-RT-PCR for c-KIT D816V transcript at Baseline, cycle 1 day 15, cycle 1, 2, 3 day 28 and every 3rd subsequent cycle, end of study. Mutation analysis of c-kit: Three separate groups, each with the following patient populations: SM Endpoints: response rates after 3 months of therapy.

Example 2

Combination of AMN107 and PKC412

In the current study, we show that the novel TK inhibitors PKC412[5] and AMN107[27] counteract growth of neoplastic human MC and Ba/F3 cells expressing KIT D816V quite effectively. PKC412 appears to be the more potent compound in this regard. We also show that PKC412 and AMN107 synergize in producing growth inhibition in HMC-1 cells expressing or lacking KIT D816V. These data show that PKC412 and AMN107 may be novel promising targeted drugs for the treatment of mastocytosis.

Materials and Methods
Reagents

The TK inhibitors imatinib (STI571), AMN107[27], and PKC412[5] are obtained from Novartis Pharma AG (Basel, Switzerland). Stock solutions of AMN107 and PKC412 are prepared by dissolving in dimethyl sulfoxide (DMSO) (Merck, Darmstadt, Germany). Recombinant human (rh) stem cell factor (SCF) is purchased from Strathmann Biotech (Hannover, Germany), RPMI 1640 medium and fetal calf serum (FCS) from PAA laboratories (Pasching, Austria), L-glutamine and Iscove's modified Dulbecco's medium (IMDM) from Gibco Life Technologies (Gaithersburg, Md.), $^3$H-thymidine from Amersham (Buckinghamshire, UK), and propidium iodide from Sigma (St. Louis, Mo.). Interferon alpha (IFNα) is obtained from Roche (Basel, Switzerland), 2-chlorodeoxyadenosine (cladribine, denoted herein as "2CdA") from Janssen Cilag (Titusville, N.J.), and rh interleukin-4 (IL-4) from Peprotech (Rocky Hill, N.J.). The phycoerythrin (PE)-labeled monoclonal antibodies (mabs) IVTO85 (CD2), WM15 (CD13), YB5.B8 (CD117), N6B6.2 (CD164), and 97A6 (CD203c) are purchased from Becton Dickinson (San Jose, Calif.), and the PE-conjugated mAb CLB-gran12 (CD63) from Immunotech (Marseille, France).

HMC-1 Cells Expressing or Lacking c-KITD816V

The human mast cell line HMC-1[28] generated from a patient with mast cell leukemia, was kindly provided by Dr. J. H. Butterfield (Mayo Clinic, Rochester, Minn.). Two subclones of HMC-1 are used, namely HMC-1.1 harbouring the c-KIT mutation V560G but not the c-KIT mutation D816V[20], and a second subclone, HMC-1.2, harbouring both c-KIT mutations, i.e. V560G and D816V.[20] HMC-1 cells are grown in IMDM supplemented with 10% FCS, L-glutamine, and antibiotics at 37° C. and 5% $CO_2$. HMC-1 cells are re-thawed from an original stock every 4 to 8 weeks and are passaged weekly. As control of 'phenotypic stability', HMC-1 cells are periodically checked for i) the presence of metachromatic granules, ii) expression of surface KIT, and iii) the down-modulating effect of IL-4 (100 U/ml, 48 hours) on KIT expression.[29] These control experiments are done prior to each set of experiments, and only HMC-1 cells exhibiting all features of the original clone[29] are used.

BA/F3 Cells with Inducible Expression of WT c-KIT or c-KITD816V

The generation of Ba/F3 cells with doxycycline-inducible expression of wt c-KIT (Ton.Kit.wt) or c-KIT D816V is described in detail elsewhere.[30] In brief, Ba/F3 cells expressing the reverse tet-transactivator[31,32] are co-transfected with pTRE2 vector (Clontech, Palo Alto, Calif.) containing c-KIT D816V cDNA (or wt c-KIT cDNA, both kindly provided by Dr. J. B. Longley, Columbia University, New York, USA) and pTK-Hyg (Clontech) by electroporation. After electroporation, stably transfected cells are selected by growing in hygromycin, and cloned by limiting dilution. In the present study, the subclone Ton.Kit.D816V.27 is used in all experiments. These Ton.Kit.D816V cells exhibit a low growth rate upon exposure to doxycycline.[30] As assessed by Western blotting, immunocytochemistry, PCR, and restriction fragment length polymorphism (RFLP) analysis[16], expression of KIT D816V can be induced in Ton.Kit.D816V.27 cells within 12 hours by exposure to doxycycline (1 μg/ml).[30]

Isolation Of Primary Neoplastic Mast Cells

Primary bone marrow (bm) MC are obtained from a female patient (aged 54) with smouldering systemic mastocytosis (SSM), a distinct subvariant of SM characterized by involvement of multiple hematopoietic lineages and detection of c-KIT D816V in MC- and non-MC-lineage myeloid cells.[34-36] For control purpose, bm obtained from a patient suffering from malignant lymphoma (without bm involvement) who underwent staging, is analyzed. Both patients gave informed consent before bm puncture. The bm aspirate is obtained from the posterior iliac crest and collected in syringes containing preservative-free heparin. Cells are layered over Ficoll to isolate mononuclear cells (MNC). The MNC fractions are found to contain 5% MC in the patient with SSM, and less than 1% MC in the control sample (normal bm). Cell viability is >90%. The presence of the c-KIT mutation D816V in bm MNC in the patient with SSM is confirmed by RT-PCR and RFLP analysis performed as described previously.[16]

Analysis of Kit Phosphorylation by Western Blotting

HMC-1 cells ($10^6$/ml) and Ba/F3 cells ($10^6$/ml) containing either wt KIT (Ton.Kit.wt) or KIT D816V (Ton.Kit.D816V.27) are incubated with PKC412 (1 µM), AMN107 (1 µM), imatinib (1 µM), or control medium at 37° C. for 4 hours. Prior to exposure to inhibitory drugs, Ton.Kit.wt cells and Ton.Kit.D816V.27 cells are incubated with doxycycline (1 µg/ml) at 37° C. for 24 hours to induce expression of KIT. In case of Ton.Kit.wt cells, KIT phosphorylation is induced by adding rhSCF (100 ng/ml). Immunoprecipitation (IP) and Western blotting are performed as described previously.[32] In brief, cells are washed at 4° C. and resuspended in RIPA buffer (1 ml buffer per $10^8$ cells) consisting of 50 mM Tris, 150 mM sodium chloride (NaCl), 1% nonidet P40 (NP-40), 0.25% deoxycholic acid, 0.1% sodium dodecyl sulfate (SDS), 1 mM ethylene-diamine-tetraacetic acid (EDTA), 1 mM sodium fluoride (NaF), 1 mM phenylmethylsulfonyl fluoride (PMSF) and 1 mM sodium orthovanadate ($Na_3VO_4$). After incubation in RIPA buffer supplemented with proteinase inhibitor cocktail (Roche) for 30 minutes at 4° C. (vortexed vigorously every 5 minutes), lysates are centrifuged to remove insoluble particles. For IP, lysates from $1 \times 10^7$ cells are incubated with anti-KIT antibody SR1[37] (kindly provided by Dr. V. Broudy, University of Washington, Seattle, Wash.) or with the anti-KIT antibody 1C1[38] (kindly provided by Dr. H.-J. Bühring, University of Tübingen, Germany) and protein G Sepharose beads (Amersham) in IP-buffer (50 mM Tris-Cl, pH 7.4, 150 mM NaCl, 100 mM NaF, and 1% NP40) at 4° C. overnight. Then, beads are washed 3 times in IP buffer. Lysates and immunoprecipitates are then separated under reducing conditions by 7.5% SDS-polyacrylamide gel electrophoresis and transferred to a nitrocellulose membrane (Protran, Schleicher & Schuell, Keene, N.H.) in buffer containing 25 mM Tris, 192 mM glycine, and 20% methanol at 4° C. Membranes are blocked for 1 hour in 5% blocking reagent (Roche) and are then incubated with anti-KIT antibody 1C1 or with the monoclonal antibody 4G10 (Upstate Biotechnology, Lake Placid, N.Y.) directed against tyrosine-phosphorylated proteins, at 4° C. overnight. Antibody reactivity is made visible by sheep anti-mouse IgG antibody and Lumingen PS-3 detection reagent (both from Amersham), and a CL-Xposure film (Pierce Biotechnology, Rockford, Ill.).

Measurement of $^3$H-thymidine Uptake

To determine growth-inhibitory drug effects, HMC-1 cells and Ba/F3 cells containing either SCF-activated wt KIT (Ton.Kit.wt) or KIT D816V (Ton.Kit.D816V.27) are incubated with various concentrations of PKC412 (100 pM-10 µM), AMN107 (1 nM-100 µM), or imatinib (3 nM-300 µM) in 96 well culture plates (PTT, Trasadingen, Switzerland) at 37° C. in 5% $CO_2$ for 48 hours. In time course experiments, HMC-1 cells are exposed to PKC412 (300 nM) for various time periods (1, 12, 24, 36, and 48 hours). In select experiments, HMC-1 cells (both subclones) are incubated with various concentrations of IFNα (0.1-500,000 U/ml) or 2CdA (0.005-10 µg/ml). Primary cells (bm cells from a patient with SSM and control bm cells) are cultured in the presence or absence of inhibitors (PKC412, 50-500 nM; AMN107, 100 nM-30 µM; imatinib, 1 µM) for 48 hours.

After incubation, 1 µCi of $^3$H-thymidine is added to each well and kept for 12 hours (37° C.). Then, cells are harvested on filter membranes (Packard Bioscience, Meriden, Conn.) in a Filtermate 196 harvester (Packard Bioscience). Filters are air-dried and the bound radioactivity counted in a β-counter (Top-Count NXT, Packard Bioscience).

In a separate set of experiments, we determined effects of drug combinations (additive versus synergistic) on growth of neoplastic MC. For this purpose, HMC-1 cells (both subclones) are exposed to various combinations of drugs (PKC412, AMN107, imatinib, IFNα, 2CdA) at a fixed ratio of drug concentrations. Drug interaction (additive versus synergistic) are determined by calculating combination index values using a commercially available software (Calcusyn; Biosoft, Ferguson, Mo.).[39] All experiments are performed in triplicates.

Evaluation of Apoptosis by Conventional Morphology and Electron Microscopy

The effects of TK-inhibitors on apoptosis in HMC-1 cells are analysed by morphologic examination, flow cytometry, and electron microscopy. In typical experiments, HMC-1 cells are incubated with various concentrations of PKC412 (500 nM-1 µM), AMN107 (50 nM-10 µM), imatinib (50 nM-10 µM) or control medium in 6 well culture plates (PTT) in IMDM medium containing 10% FCS at 37° C. for 24 hours. The percentage of apoptotic cells is quantified on Wright-Giemsa-stained cytospin preparations. Apoptosis is defined according to conventional cytomorphological criteria (cell shrinkage, condensation of chromatin structure).[40]

To confirm apoptosis in HMC-1 cells, electron microscopy is performed as described[41,42] using HMC-1 cells (both subclones) exposed to PKC412 (500 nM, 900 nM, or 1 µM), AMN107 (1 µM), imatinib (1 µM), or control medium in 25 ml plastic culture flasks (PTT) for 24 hours. After incubation, cells are washed and fixed in 2% paraformaldehyde, 2.5% glutaraldehyde, and 0.025% $CaCl_2$ buffered in 0.1 mol/L sodium cacodylate buffer (pH 7.4) at room temperature (RT) for 60 minutes. Then, cells are washed three times in 0.1 mol/L sodium cacodylate buffer, suspended in 2% agar, and centrifuged. The pellets are post-fixed with 1.3% $OsO_4$ (buffered in 0.66 mol/L collidine) and stained 'en bloc' in 2% uranyl acetate and sodium maleate buffer (pH 4.4) for 2 hours at RT. Then, pellets are rinsed, dehydrated in alcohol series, and embedded in EPON 812. Ultrathin sections (85 nM) are cut and placed on gold grids. Sections are contrasted in uranyl acetate and lead citrate, and viewed in a JEOL 1200 EX II transmission electron microscope (JEOL, Tokyo, Japan). The presence of apoptotic cells are determined using conventional morphologic criteria (see above).

Evaluation of Apoptosis by Tunnel Assay and Flow Cytometry

To confirm apoptosis in HMC-1 cells exposed to PKC412 (1 µM), AMN107 (1 µM), or imatinib (1 µM) for 24 hours, a Tunnel (in situ Terminal transferase-mediated dUTP-fluorescene Nick End-Labeling) assay is applied as described previously.[43,44] In brief, cells are first washed in phosphate buffered saline (PBS) and fixed in 1% formaldehyde at pH 7.4 at 0° C. for 15 minutes. Then, cells are treated with 70% ethanol (ice cold) for 1 hour, washed in PBS, and incubated in terminal transferase reaction solution containing $CoCl_2$, DNA deoxy-nucleotidyl-exotransferase, and biotin-16-2'-deoxy-uridin-5'-triphosphate (prepared according to the instructions of the manufacturer Boehringer Mannheim, Germany) at 37° C. for 10 minutes. After incubation, cells are washed and then incubated with Streptavidin Fluorescein (Boehringer Mannheim) (10 µg/ml) at 37° C. for 20 minutes. HMC-1 cells are then washed and analyzed with a Nikon Microphot-FXA fluorescence microscope (Tokyo, Japan).

For flow cytometric determination of apoptosis and cell viability, combined annexin V/propidium iodide staining is performed. For this purpose, HMC-1 cells are exposed to PKC412 (0.5, 1, and 2.5 µM), AMN107 (0.5, 1, and 2.5 µM), imatinib (0.5, 1, and 2.5 µM), or control medium at 37° C. for 24 hours. Thereafter, cells are washed in PBS and then are incubated with annexinV-APC (Alexis Biochemicals, Lausen, Switzerland) in binding buffer containing HEPES (10 mM, pH 7.4), NaCl (140 mM), and $CaCl_2$ (2.5 mM). Thereafter, propidium iodide (1 µg/ml) is added. Cells are then washed and analyzed by flow cytometry on a FACSCalibur (Becton Dickinson).

Evaluation of Expression of Activation-Linked Surface Antigens on HMC-1 Cells

Expression of cell surface antigens on HMC-1 cells carrying KIT D816V (HMC-1.2 cells) is determined by flow cytometry after short term culture (for 24 hours) in control medium or medium supplemented with TK inhibitors (PKC412, 1 µM; AMN107, 1 µM; imatinib, 1 µM). In select experiments, various concentrations of PKC412 (50, 100, 250, 500, and 1000 nM) are applied. After incubation with drugs, HMC-1 cells are washed and subjected to single color flow cytometry using PE-conjugated antibodies against MC antigens known to be overexpressed on neoplastic MC in SM (compared to normal MC) and/or are expressed at an early stage of mastopoiesis (CD2, CD13, CD63, CD117, CD164, CD203c).[45-47] Flow cytometry is performed on a FACSan (Becton Dickinson) as described previously.[29]

Statistical Analysis

To determine the significance in differences between proliferation rates, apoptosis, and surface expression levels after exposure of HMC-1 cells to inhibitors, the student's t test for dependent samples is applied. Results are considered statistically significant when p is <0.05.

Results

Effects of PKC412 and AMN107 on Tk Activity of D816V-Mutated Kit

Figure 1B:
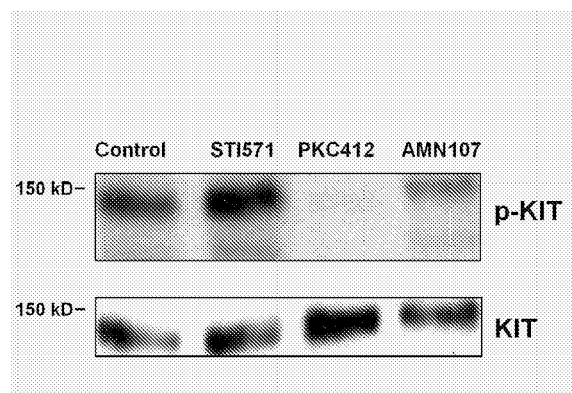
Figure 1C:
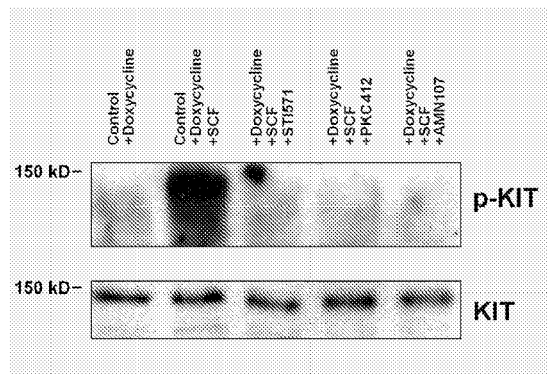
Figure 1D:
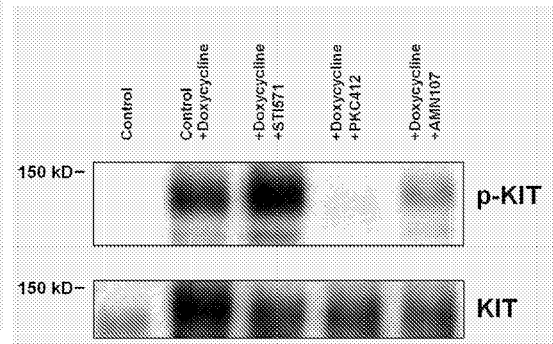

As assessed by EP and Western blotting, PKC412 (1 µM) decreased phosphorylation of KIT in HMC-1.1 cells (exhibiting the c-KIT mutation V560G but not the c-KIT mutation D816V) as well as in HMC-1.2 cells harbouring the V560G-mutated as well as the D816V-mutated variant of KIT (FIGS. 1A and 1B). The novel TK inhibitor AMN107 (1 µM) strongly reduced KIT phosphorylation in HMC-1.1 cells, but showed only a weak effect on KIT phosphorylation in HMC-1.2 cells at 1 µM. Similarly, imatinib (1 µM) reduced KIT phosphorylation in HMC-1.1 cells, but did not inhibit KIT phosphorylation in HMC-1.2 cells (FIGS. 1A and 1B). In a next step, we examined the effects of the TK inhibitors on Ba/F3 cells exhibiting wt KIT (Ton.Kit.wt) or KIT D816V (Ton.Kit.D816V.27) after exposure to doxycycline. In Ton.Kit.wt cells, KIT appeared to be phosphorylated in the presence (but not in the absence) of SCF, whereas KIT is found to be constitutively phosphorylated in Ton.Kit.D816V.27 cells (FIG. 1C). As visible in FIG. 1C, all 3 TK inhibitors (PKC412, AMN107, imatinib, each 1 µM) decreased the SCF-induced phosphorylation of KIT in Ton.Kit.wt cells. By contrast, only PKC412, and to a lesser degree AMN107, decreased the SCF-independent phosphorylation of KIT in Ton.Kit.D816V-27 cells. Imatinib (1 µM) showed no detectable effect on the phosphorylation of KIT in these cells (FIG. 1D). These data show that PKC412 is a novel potent inhibitor of the TK activity of wt KIT, KIT V560G, and KIT D816V, and that AMN107 is a novel potent inhibitor of wt KIT and KIT V560G, and a weaker inhibitor of (auto)phosphorylation of KIT D816V.

Effects of TK-Inhibitors on $^3$H-thymidine Uptake in HMC-1 Cells

Figure 2A:
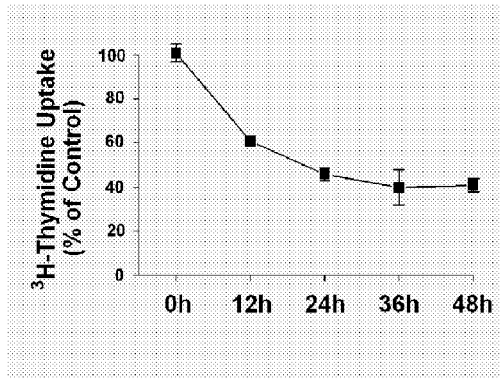
FIG. 2A-D is a graphic representation of the effects of PKC412, AMN107, and imatinib on proliferation of HMC-1 cells.
Figure 2B:
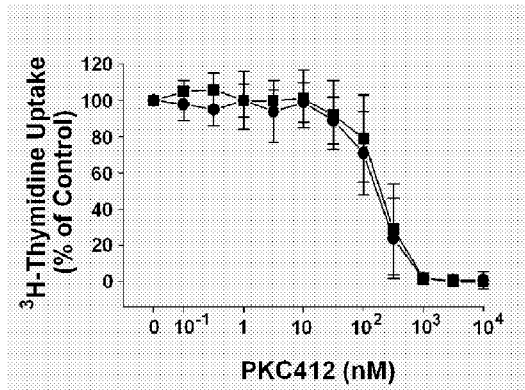
Figure 2C:
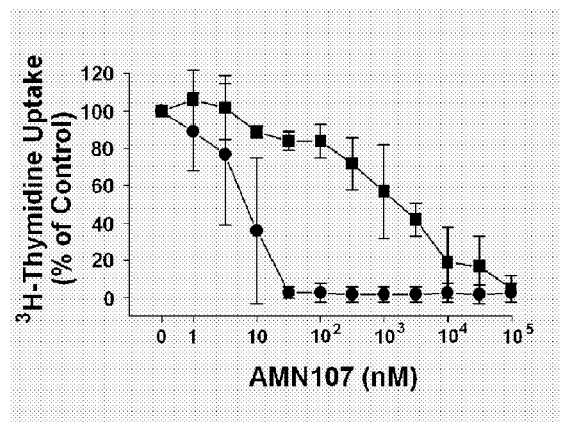
Figure 2D:
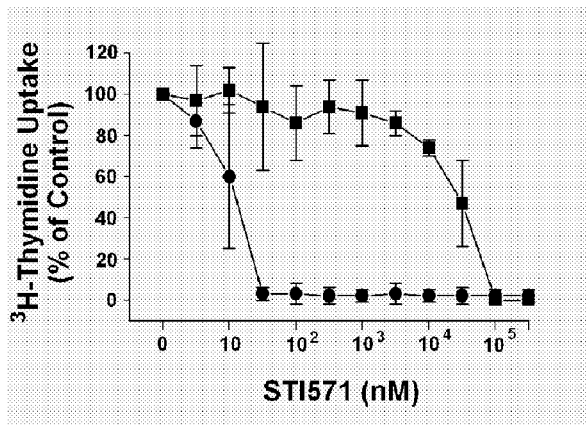

In time course experiments, maximum inhibitory effects of PKC412, AMN107, and imatinib on growth of HMC-1.1 cells and HMC-1.2 cells are seen after 36-48 hours. FIG. 2A shows the time-dependent effect of PKC412 (300 nM) on growth of HMC-1.2 cells. As shown in FIGS. 2B and 2C, PKC412 and AMN107 are found to counteract $^3$H-thymidine uptake in HMC-1.1 cells and HMC-1.2 cells in a dose-dependent manner. Interestingly, the $IC_{50}$ for the effects of PKC412 in these two subclones appeared to be in the same range (50-250 nM) (FIG. 2B). In contrast, the $IC_{50}$ values for the effects of AMN107 on proliferation are significantly higher in HMC-1.2 cells (1-5 µM) compared to that found in HMC-1.1 cells (3-10 nM) (FIG. 2C). As expected, imatinib is only effective at pharmacologically relevant concentrations in HMC-1.1 cells ($IC_{50}$: 10-30 nM), whereas no significant anti-proliferative effects of imatinib on HMC-1.2 cells are seen (FIG. 2D) confirming previous data.[20-22] An interesting observation is that AMN107 is the most potent compound (on a molar basis) when comparing growth-inhibitory effects of the three drugs on HMC-1.1 cells exhibiting the c-KIT mutation V560G (but not the c-KIT mutation D816V) (FIG. 2B-D).

Figure 3A:
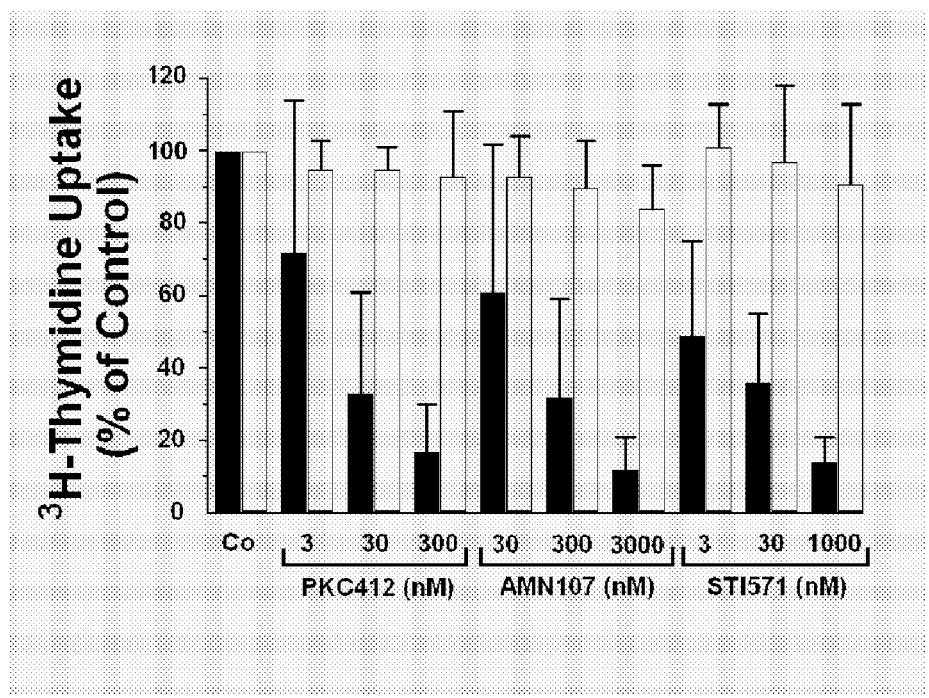
FIG. 3A-B is a graphic representation of the effects of PKC412, AMN107, and imatinib on $^3$H-thymidine uptake in Ton.Kit cells.
Figure 3B:
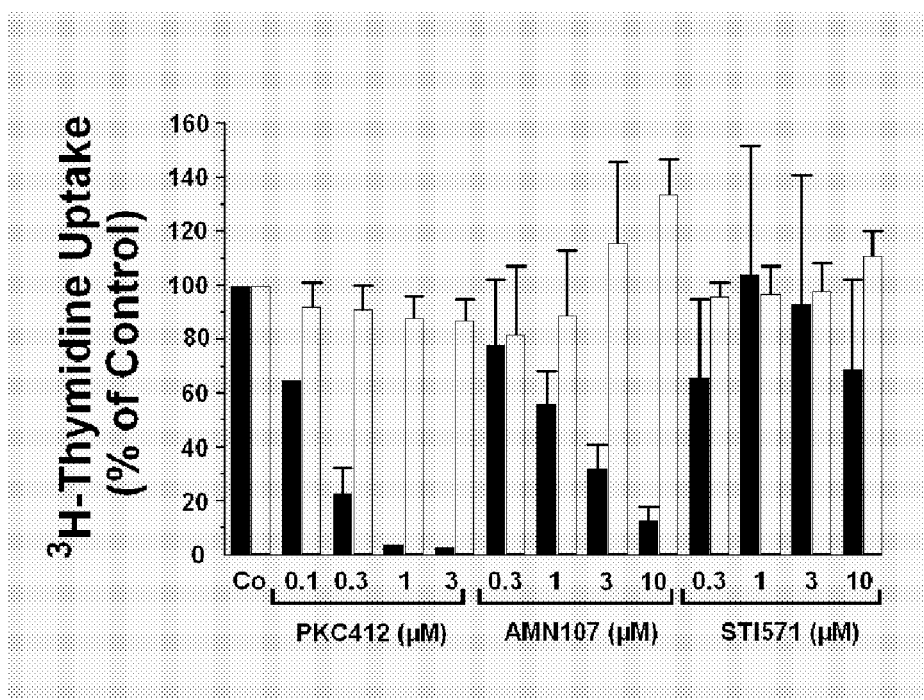

Effects of Tk-Inhibitors on Growth of Ba/F3 Cells Expressing wt Kit or KIT D816V As shown in FIG. 3A, all 3 TK inhibitors are found to counteract SCF-dependent growth of doxycycline-exposed (KIT-expressing) Ton.Kit.wt cells in a dose-dependent manner with $IC_{50}$ values of 3-30 nM for PKC412, 30-300 nM for AMN107, and 3-30 nM for imatinib. By contrast, in Ton.Kit.D816V cells, only PKC412 ($IC_{50}$: 100-300 nM), and to lesser degree AMN107 ($IC_{50}$: 1-3 µM) are found to inhibit $^3$H-thymidine incorporation, whereas no significant effect is obtained with imatinib over the dose range tested (FIG. 3B). None of the three inhibitors used are found to counteract growth of Ton.Kit.wt cells or Ton.Kit.D816V.27 cells in the absence of doxycycline, i.e. in the absence of KIT (FIGS. 3A and 3B). In further control experiments, neither doxycycline (1 µg/ml), nor the TK inhibitors (imatinib, PKC412, AMN107), showed growth-inhibitory effects on control (non-transfected) Ba/F3 cells (not shown).

Figure 4:
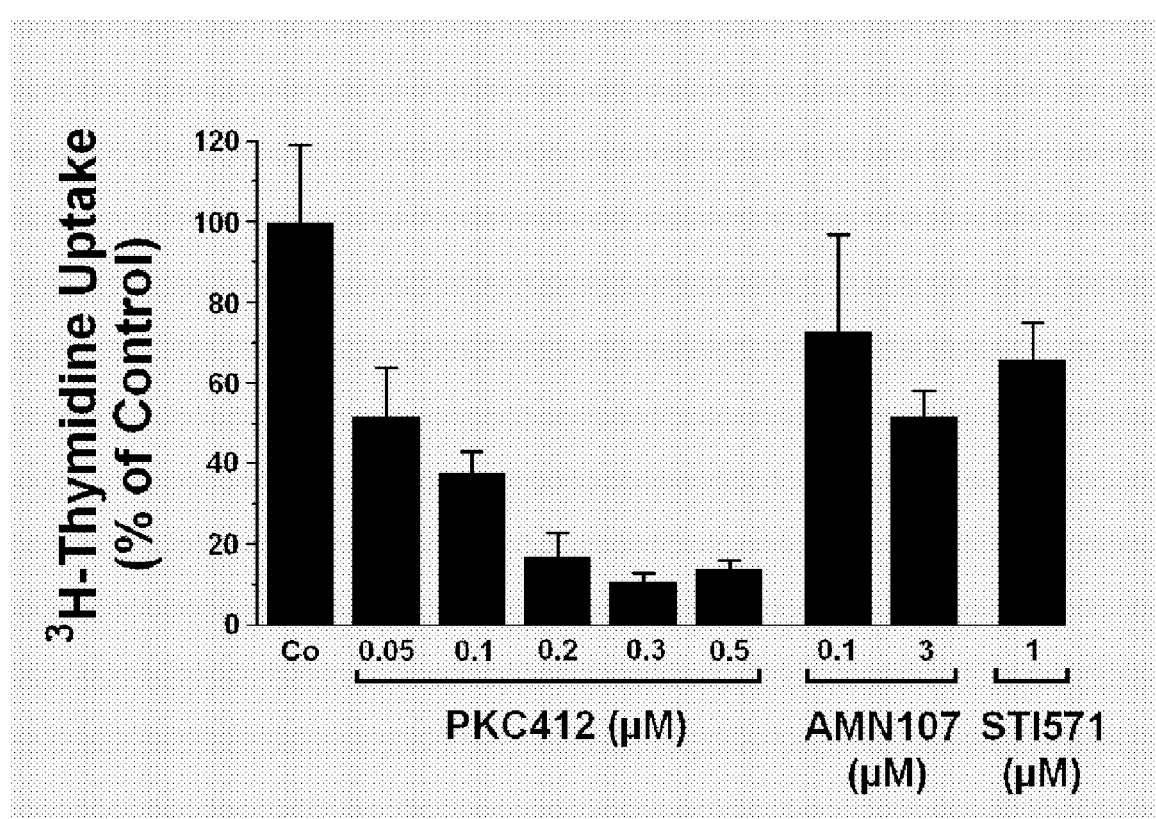
FIG. 4 is a graphic representation of PKC412 downregulation of growth of primary neoplastic (mast) cells exhibiting D816V. Primary neoplastic bone marrow cells expressing KIT D816V are isolated from a patients with smouldering systemic mastocytosis. Isolated cells are incubated in control medium (Co) or with various concentrations of PKC412, AMN107, and imatinib as indicated. Cell growth is quantified by measuring $^3$H-thymidine uptake. Results are expressed as percent of control (wherein Co equals 100%) and represent the mean±S.D. of triplicates. In normal bm cells, no effects of PKC412 are seen (not shown).

PKC412 and AMN107 Counteract Growth of Primary Neoplastic (MAST) Cells Expressing KIT D816V To reconfirm anti-proliferative effects of PKC412 and AMN107 in systemic mastocytosis, we examined the response of primary neoplastic bone marrow (bm)-derived MC in a patient with smouldering SM, a special subvariant of SM in which most myeloid cells (MC as well as non MC-lineage cells) exhibit KIT D816V. In fact, although the purity of MC is only 4%, most of the myeloid cells in this sample exhibited KIT D816V. In these neoplastic bm cells, PKC412 and AMN107 are found to inhibit the spontaneous uptake of $^3$H-thymidine in a dose-dependent manner, whereas no significant effect is seen with imatinib (1 µM) (FIG. 4). In the control sample (normal bm, no hematologic disease), PKC412 showed no effect on $^3$H-thymidine uptake (not shown).

PKC412 and AMN107 Induce Apoptosis IN HMC-1 Cells

Figure 6:
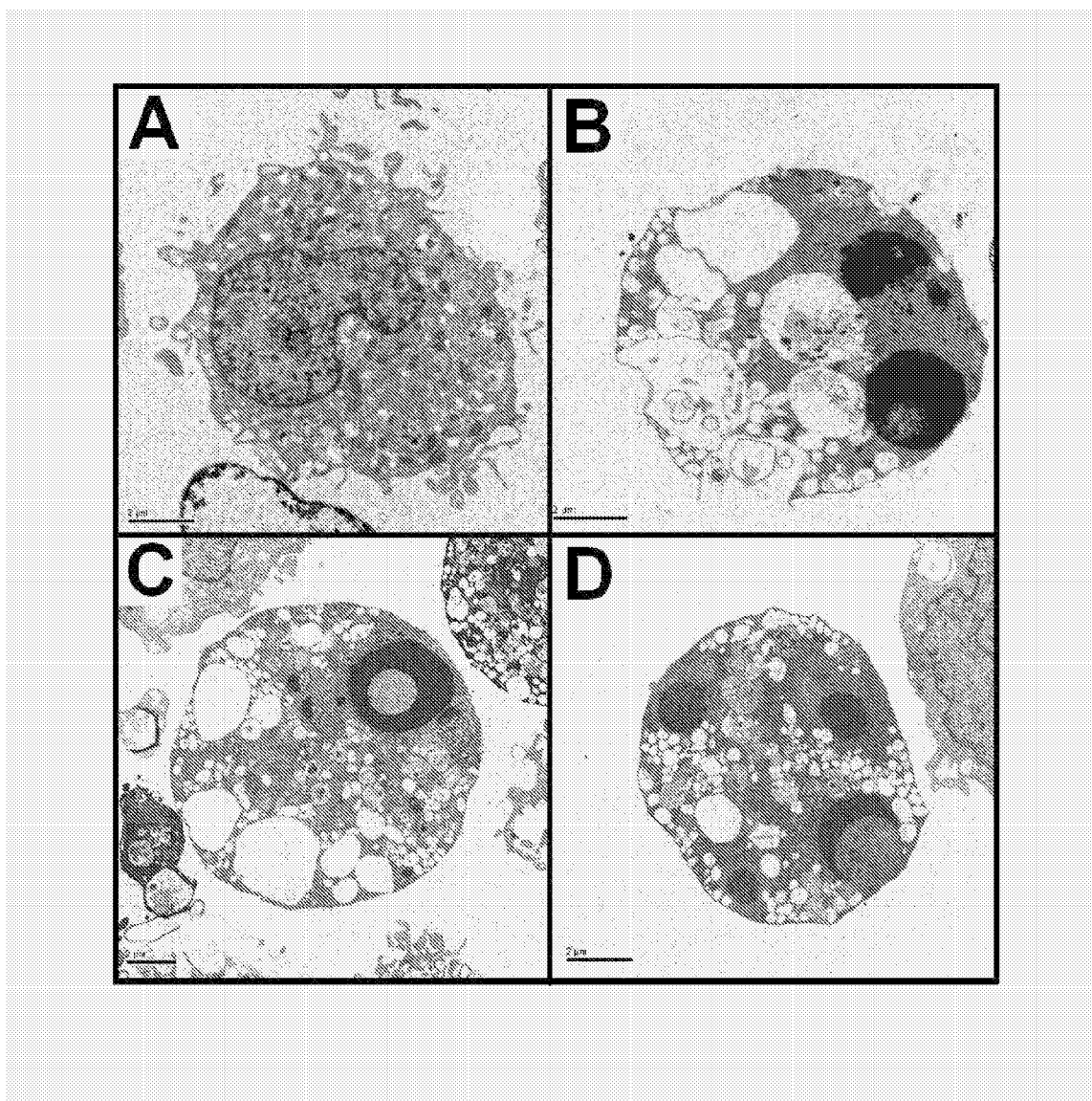
FIG. 6A-D is a representation of electron microscopic examination of PKC412-induced apoptosis in HMC-1 cells. HMC-1.2 cells are incubated with control medium (FIG. 6A), PKC412, 500 nM (FIG. 6B), or PKC412, 900 nM (FIG. 6C,D) at 37° C. for 24 hours. Then, cells are harvested and analyzed for ultrastructural signs of apoptosis. Whereas apoptotic cells are rarely seen in cultures kept with control medium (FIG. 6A), HMC-1.2 cells cultured in PKC412 (FIG. 6B-D) frequently displayed signs of apoptosis including cell shrinkage, membrane ruffling, vacuolization, and condensation of the nuclear chromatin.
Figure 7:
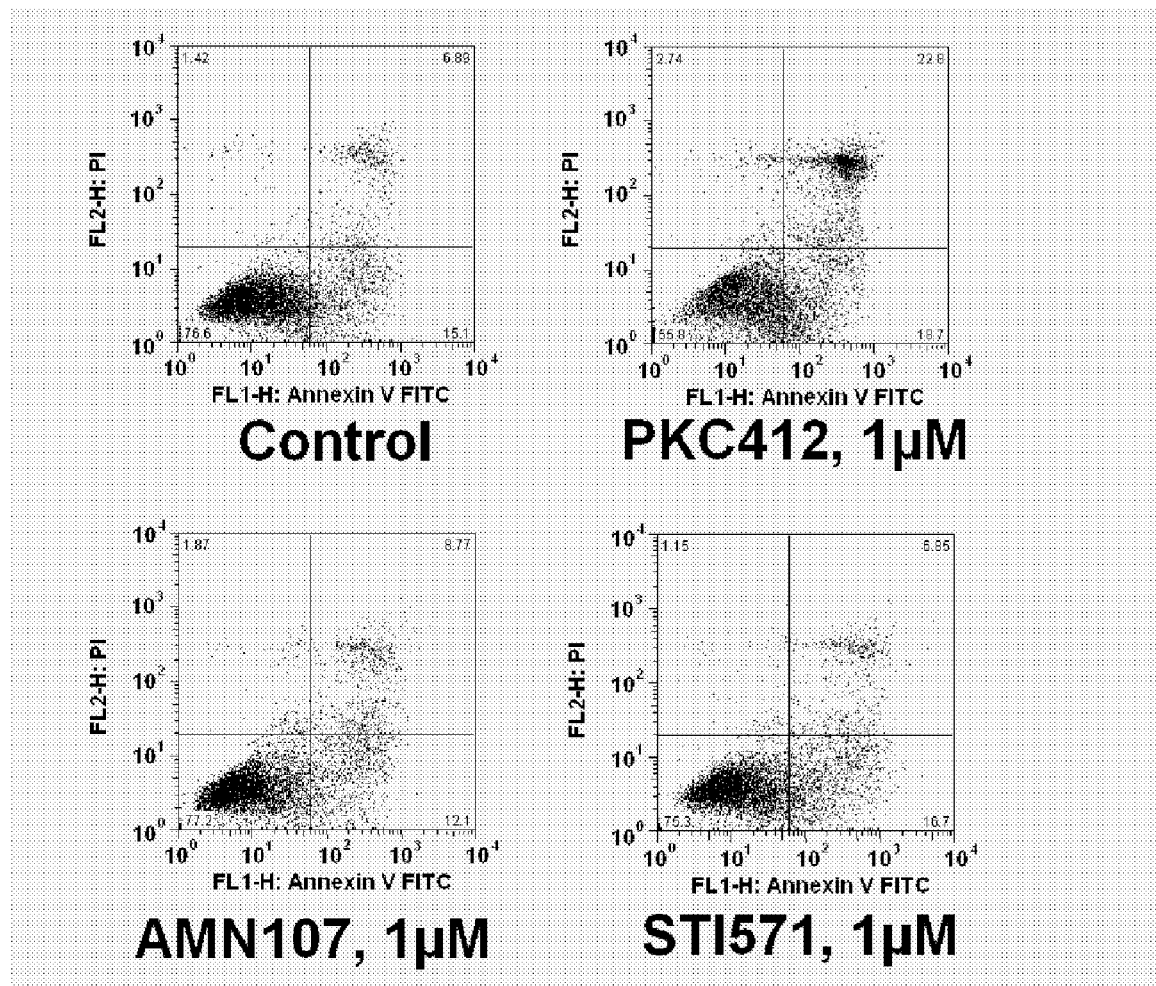
FIG. 7 is a representation of HMC-1.2 cells exposed to control medium (Control), PKC412 (1 μM), AMN107 (1 μM), or imatinib (1 μM) at 37° C. for 24 hours. Then, cells are examined for viability and apoptosis by combined propidium iodide (PI)/Annexin V-FITC staining.
Figure 8:
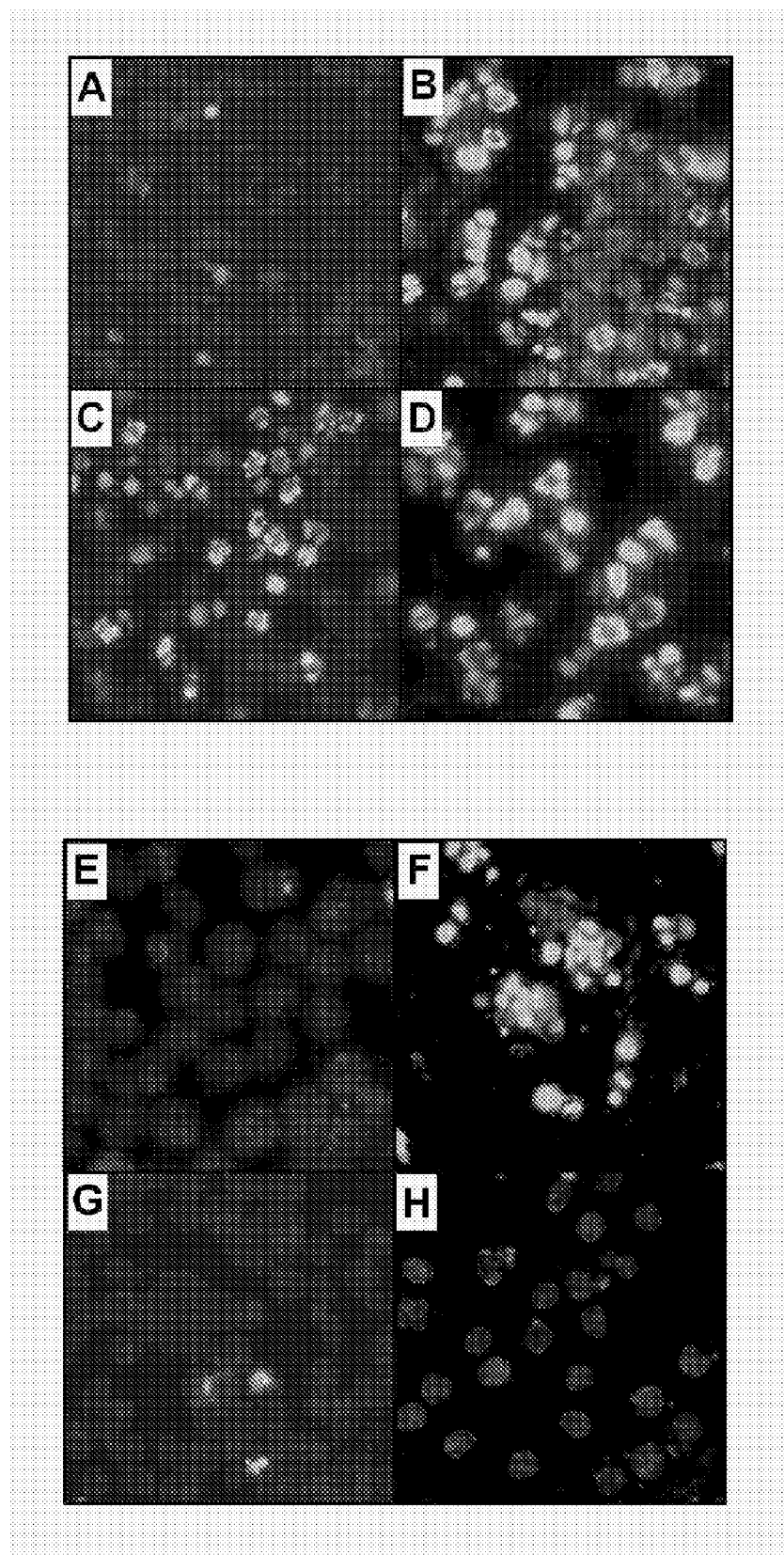
FIG. 8A-H*is* a representation of apoptosis in HMC-1 cells assessed by Tunel assay. HMC-1.1 cells (FIG. 8A-D) and HCM-1.2 cells (FIG. 8E-H) are incubated in control medium (FIG. 8A,E), PKC412, 1 μM (FIG. 8B,F), AMN107, 1 μM (FIG. 8C,G), or imatinib, 1 μM (FIG. 8D,H) at 37° C. for 24 hours. Thereafter, cells are harvested and subjected to Tunel assay. As visible, PKC412 produced apoptosis in most HMC-1.1 and HMC-1.2 cells, whereas AMN107 and imatinib showed potent apoptosis-inducing effects only in HMC-1.1 cells (FIG. 8C,D), but not in HMC-1.2 cells exhibiting KIT D816V (FIG. 8G,H).

To explore the mechanisms underlying the growth-inhibitory effects of PKC412 and AMN107 on neoplastic human MC exhibiting or lacking KIT D816V, we analyzed morphological and biochemical signs of apoptosis in HMC-1.1 cells and HMC-1.2 cells after drug exposure. In these experiments, PKC412 is found to induce apoptosis in both HMC-1 subclones in a dose-dependent manner (FIGS. 5A and 5B). AMN107 is also found to induce apoptosis in both HMC-1 subclones in a dose-dependent manner, but the effect of this compound is much more pronounced in HMC-1.1 cells (FIG. 5C) compared to that found in HMC-1.2 cells (FIG. 5D). Similarly, imatinib is found to produce apoptosis in HMC-1.1 cells (FIG. 5E), but showed no effect on HMC-1.2 cells (FIG. 5F). The apoptosis-inducing effects of the drugs on HMC-1 cells could be confirmed by electron microscopy. Again, all three drugs (each 1 µM) are found to induce apoptosis in HMC-1.1 cells, whereas in HMC-1.2 cells, only PKC412 and to a lesser degree AMN107, are found to produce apoptosis in HMC-1.2 cells. FIG. 6 shows the apoptosis-inducing effect of PKC412 (1 µM, 24 hours) on HMC-1.2 cells. As visible, many of the HMC-1 cells exposed to PKC412 (FIG. 6B-D) exhibited typical ultrastructural signs of apoptosis compared to cells kept in control medium (FIG. 6A). Finally, we are able to demonstrate the apoptosis-inducing effects of PKC412 and AMN107 in HMC-1 cells by combined annexinV/propidium iodide staining and flow cytometry (FIG. 7) as well as in a Tunel assay (FIG. 8). In both assays, PKC412 (1 µM) and to a lesser degree AMN107 (1 µM) are found to induce apoptosis in HMC-1.2, whereas imatinib showed no effects (FIGS. 7 and 8E-H). By contrast, in HMC-1.1 cells, all 3 compounds are found to induce apoptosis as assessed by Tunel assay (FIG. 8A-D).

These data provide evidence that the growth-inhibitory effects of PKC412 and AMN107 on HMC-1 cells are associated with induction of apoptosis.

Figure 9A:
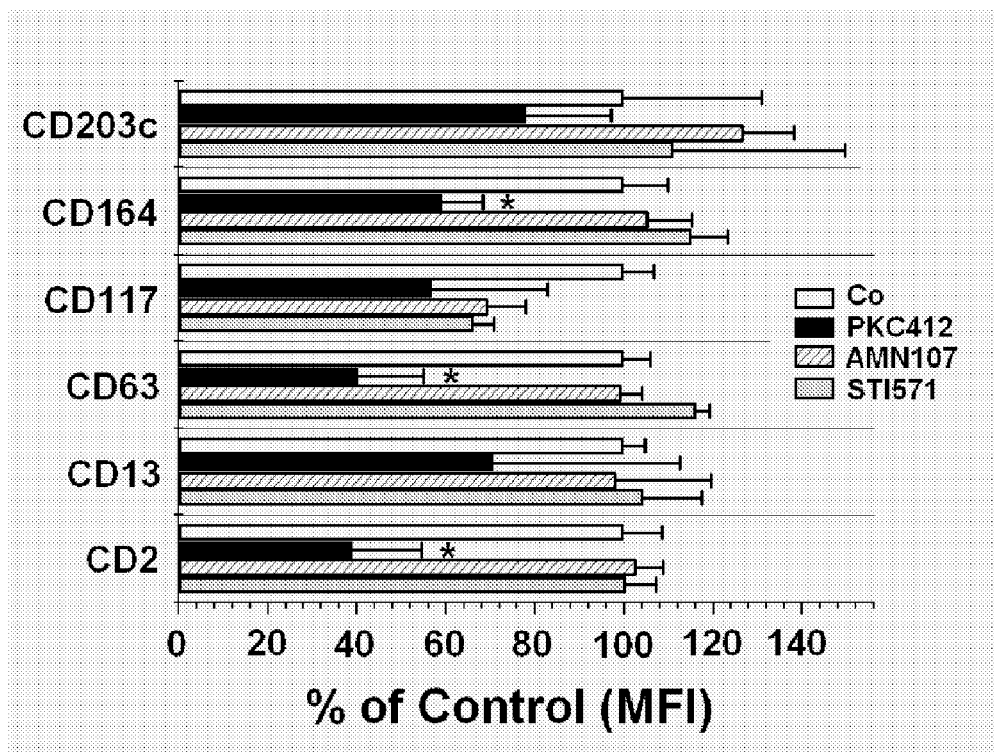
FIG. 9A-B is a graphic representation of the effects of TK inhibitors on expression of cell surface antigens on HMC-1.2 cells.
Figure 9B:
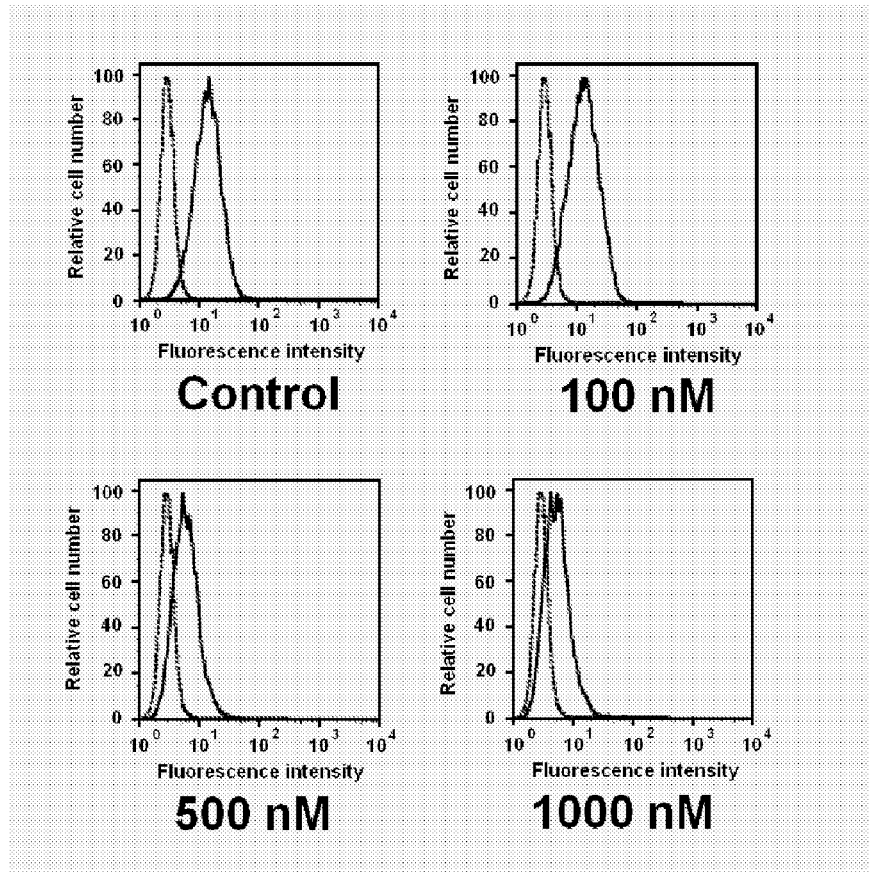
Figure 10G:
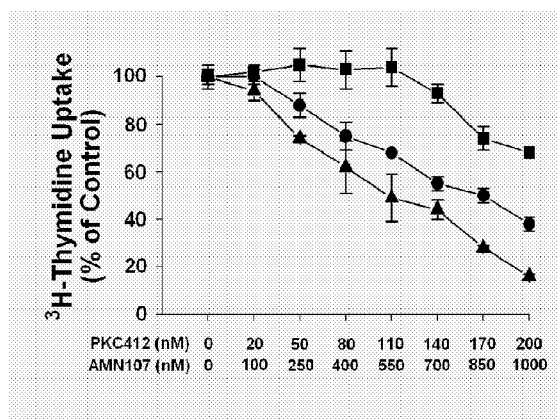
Figure 10H:
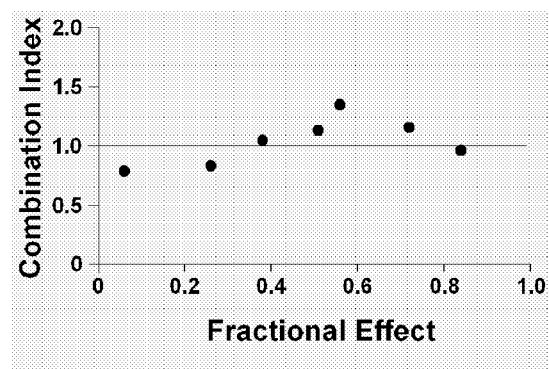
Figure 10I:
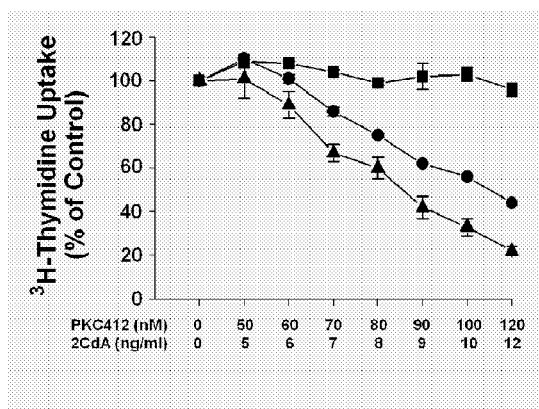
Figure 10J:
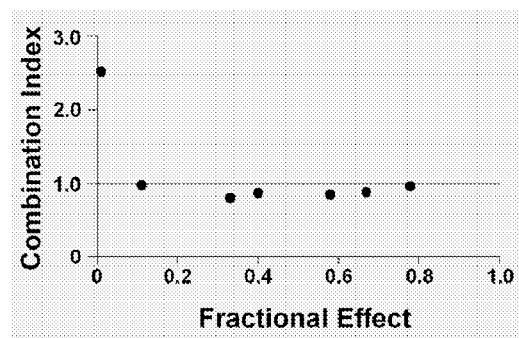

PKC412 Downregulates Expression of Activation-Linked and SM-Related Cell Surface Antigens on HMC-1 Cells Several cell surface antigens that are typically (over)expressed on neoplastic MC in SM may play a role in the growth, activation, or distribution of neoplastic cells.[45,46] Some of these molecules may be upregulated directly by the D816V-mutated variant of KIT.[30] We therefore asked whether PKC412, AMN107, or imatinib, would influence expression of cell surface antigens on HMC-1.2 cells. Unstimulated HMC-1.2 cells are found to express LFA-2 (CD2), aminopeptidase-N (CD13), CD63, KIT (CD117), CD164, and E-NPP3 (CD203c) confirming previous data.[45-47] Incubation of HMC-1.2 cells with PKC412 resulted in a significant decrease in expression of CD2, CD63, and CD164 (p<0.05) (FIG. 9A). In contrast, no significant effects of PKC412 on expression of CD13 or CD203c are seen (FIG. 9A). In case of KIT, a slight decrease of expression on HMC-1.2 cells is found upon exposure to PKC412 (as well as on exposure to AMN107 or imatinib), but the effect is not significant (p>0.05) (FIG. 9A). The effects of PKC412 on expression of CD2 and CD63 are found to be dose-dependent. FIG. 9B shows the effects of various concentrations of PKC412 on expression of CD63 on HMC-1.2 cells. In contrast to PKC412, no significant effects of AMN107 or imatinib on expression of CD antigens on HMC-1.2 cells are seen (FIG. 9A).

PKC412 Cooperate with Other Targeted- and Conventional Drugs in Producing Growth Inhibition IN HMC-1 Cells As assessed by $^3$H-thymidine incorporation, PKC412 is found to cooperate with AMN107 in producing growth inhibition in HMC-1.1 cells and HMC-1.2 cells (FIG. 10; Table 1). In case of HMC-1.1 cells, the drug interaction is found to be clearly synergistic, whereas in HMC-1.2 cells, interactions are additive rather than synergistic (FIG. 10; Table 1). In addition, PKC412 and 2CdA, a drug successfully used to treat aggressive mastocytosis, are found to inhibit growth of HMC-1.1 cells in a synergistic manner, and the same synergistic effect is seen with PKC412 and imatinib (Table 1). Again, however, no clear synergistic effect of PKC412 and 2CdA on growth of HMC-1.2 cells is seen. Also, AMN107 and imatinib produced synergistic inhibitory effects only in HMC-1.1 cells (FIG. 10), but not in HMC-1.2 cells carrying KIT D816V (Table 1). No synergistic or additive effects on growth of HMC-1 cells are seen when combining PKC412 and interferon-alpha (IFNα) or AMN107 and IFNα (Table 1). A summary of drug interactions is shown in Table 1.

TABLE 1

Drug interactions on HMC-1.1 cells and HMC-1.2 cells

|        | PKC412 | AMN107 | STI571 | 2CdA | IFNα |
|--------|--------|--------|--------|------|------|
| PKC412 |        | +      | +      | +    | −    |
| AMN107 | ±      |        | +      | +    | −    |
| STI571 | n.t.   | ±      |        | n.t. | n.t. |
| 2CdA   | ±      | ±      | n.t.   |      | n.t. |
| IFNα   | −      | −      | n.t.   | n.t. |      |

As shown in Table 1, the effects of various drug combinations on growth of HMC-1.1 cells (upper right, white squares) and HMC-1.2 cells (lower left, grey squares) are determined by $^3$H-thymidine incorporation assay. Each drug combination is tested in at least three independent experiments. Drugs are applied at fixed ratio and resulting effects (and the type of drug interaction) determined by calcusyn software. Score: +, synergistic growth-inhibitory effect; +/−, additive effect; −, less then additive (antagonistic) effect. n.t., not tested.

Discussion

The somatic c-KIT mutation D816V is a gene defect that leads to constitutive activation of the TK domain of the KIT receptor which is critically involved in growth of (neoplastic) MC and thus in the pathogenesis of SM.[13-17] Therefore, recent attempts have focused on the identification and development of pharmacologic compounds that can inhibit the TK activity of the D816V-mutated variant of KIT and thereby can inhibit growth of neoplastic MC in patients with SM.[9-12] We here describe that the TK inhibitor PKC412, and to a lesser degree AMN107, inhibit TK activity of KIT-D816V as well as growth of neoplastic human MC carrying this particular c-KIT mutation. In addition, we show that both drugs cooperate with each other as well as with other targeted and conventional drugs in producing growth inhibition in neoplastic MC.

PKC412 is a novel staurosporine-related inhibitor of PKC and of several TKs including KDR, PDGFRA, FLT3, and KIT.[5] In the current study, we show that PKC412 counteracts growth of neoplastic human MC and Ba/F3 cells expressing the D816V-mutated variant of KIT. With regard to Ba/F3 cells, our data are in line with the results of Growney et al.[48] Interestingly, the effective dose-range for Ba/F3 cells is found to be the same as that found in HMC-1.2 cells carrying KIT D816V. Another interesting observation is that the $IC_{50}$ for the effects of PKC412 on the two subclones of HMC-1 (expressing or lacking KIT D816V) appeared to be in the same range. Finally, we are able to confirm growth inhibitory effects of PKC412 for primary neoplastic human (mast) cells expressing KIT D816V. Since the c-KIT mutation D816V is detectable in a majority of all patients with SM independent of the subtype of disease,[13-17] these data are of considerable importance. In fact, PKC412 seems to be the first TK-inhibitor that reportedly counteracts growth of KIT D816V-bearing human MC in the same way as KIT wt-expressing MC. It is also noteworthy in this regard, that the inhibitory effects of PKC412 on KIT D816V-positive cells clearly exceed the antiproliferative activities of AMN107 and imatinib. Based on these observations, PKC412 seems to be a novel attractive targeted drug to be considered for use in clinical trials in patients with (aggressive) SM or MCL.

Recent data suggest that AMN107 is a most potent inhibitor of the BCR/ABL TK activity.[27] It has also been described that AMN107 inhibits the TK activity of wild type KIT.[27] In the present study, we found that AMN107 exerts potent effects on HMC-1 cells carrying the c-KIT mutation V560G, but exhibits only weak effects on HMC-1 cells harbouring both KIT V560G and KIT D816V. Similarly, AMN107 showed only weak effects on growth of Ba/F3 cells expressing the D816V-mutated variant of KIT. These data suggest that the c-KIT mutation D816V but not the c-KIT mutation V560G, confers relative resistance against AMN107, although AMN107 still retains inhibitory effects on KIT D816V-positive HMC-1 cells compared to imatinib. The impressive antiproliferative effects of AMN107 on V560G-positive cells also suggest that this compound may be an attractive lead candidate-drug for gastrointestinal stroma cell tumors (GISTs), in which mutations at codon 560 of c-KIT have recently been reported.[49]

A number of pharmacologic inhibitors targeting the TK activity of pro-oncogenic molecules have recently been developed in clinical hematology.[5,12,19,27] The growth-inhibitory effects of these TK inhibitors on neoplastic cells (expressing the appropriate target) are usually associated with loss of TK activity and with consecutive apoptosis. In the present study, we are able to demonstrate that the growth-inhibitory effects of PKC412 on neoplastic human MC(HMC-1) is associated with TK inhibition of (mutated) KIT as well as with apoptosis. In fact, we are able to show that PKC412 induces apoptosis in HMC-1.1 cells (expressing KIT V560G but not KIT D816V) as well as in HMC-1.1 cells (expressing KIT V560G and KIT D816V). The apoptosis-inducing effect of PKC412 is demonstrable by light- and electron microscopy as well as by flow cytometry and in a Tunel assay. As expected, AMN107 and imatinib showed significant apoptosis-inducing effects on HMC-1.1 cells, but did not exhibit significant effects on HMC-1.2 cells.

A number of cell surface antigens are typically (over)expressed on neoplastic human MC. Likewise, in contrast to normal MC, neoplastic MC in patients with SM express CD2 and CD25.[45-46] In addition, the levels of CD63 and CD203c expressed on neoplastic MC in SM are higher compared to normal MC. In several cases such as CD63, the D816V-mutated variant of KIT may directly lead to enhanced surface expression.[30] We are therefore interested to know whether targeting of D816V-mutated KIT in HMC-1 cells by PKC412 is associated with a decrease in expression of 'SM-related' surface CD antigens. The results of our experiments show that PKC412 downregulates expression of CD2, CD63, and CD 164 in HMC-1.2 cells exhibiting KIT D816V. A slight albeit insignificant effect of PKC412 (as well as of AMN107) on KIT expression is also seen. An interesting observation is that AMN107 failed to suppress the expression of CD2 and CD63 on HMC-1.2 cells. This is probably due to the weaker effect of this compound on TK activity of KIT D816V when compared to the effect of PKC412.

A number of recent data suggest that treatment of myeloid neoplasms with TK inhibitors as single agents may be insufficient to control the disease for prolonged time periods. This has been documented for the use of imatinib in (advanced) CML[50,51], and may also apply for patients with ASM or MCL.[52] In the latter patients, this is a particular problem since the mutation D816V confers a primary (relative) resistance of KIT against imatinib and, to a lesser degree, relative resistance against AMN107. To overcome resistance, a number of different pharmacological strategies may be envisaged. One possibility is to apply drug-combinations. We therefore are interested to learn whether PKC412 and AMN107 would exhibit synergistic antiproliferative effects on HMC-1.1 and HMC-1.2 cells. Indeed, our data show that PKC412 cooperates with imatinib and AMN107 in producing growth inhibition in both HMC-1 clones. Furthermore, PKC412 and 2CdA, a drug that has been described to counteract growth of neoplastic MC in vivo in patients with (aggressive) SM, showed cooperative inhibitory effects on growth of HMC-1,1- and HMC-1.2 cells. However, interestingly, drug interactions are found to be synergistic only on HMC-1.1 cells, but not in HMC-1.2 cells. This may be explained by the relatively weak (AMN107) or absent (imatinib) effects of co-applied drugs on KIT TK activity and thus growth of HMC-1.2 cells carrying D816V as compared to the much more pronounced effects of the same drugs on HMC-1.1 cells. No cooperative drug effects are seen when combining IFNα with AMN107 or PKC412. Whether drug combinations consisting of PKC412 and other (targeted) drugs will be of clinical value in patients with ASM or MCL remains unknown.

Thus, so far, only a few agents with documented antiproliferative effects on neoplastic MC in vivo in patients with SM have been presented, and none of these drugs produce long lasting complete remissions in patients with ASM or MCL. The notion that PKC412 is a most potent novel inhibitor of growth of neoplastic human MC carrying the D816V-mutated variant of KIT is of particular interest in this regard.

In summary, we show that PKC412 and AMN107 are novel promising drugs targeting wild type KIT and mutated variants of KIT in SM. Whereas each of the two drugs may exhibit a distinct pharmacological profile with unique effects on mutated variants of KIT, a most effective and promising approach may be to combine both drugs with each other or with the clinically established drug 2CdA to treat patients with ASM or MCL in the future.

Example 1 References

1. Reilly J T. Class III receptor tyrosine kinases: role in leukaemogenesis. Br J. Haematol. 2002; 116:744-757.
2. Deininger M W, Druker B J. Specific targeted therapy of chronic myelogenous leukemia with imatinib. Pharmacol Rev. 2003; 55:401-423.
3. Pardanani A, Tefferi A. Imatinib targets other than bcr/abl and their clinical relevance in myeloid disorders. Blood. 2004; 104:1931-1939.
4. Shah N P, Tran C, Lee F Y, Chen P, Norris D, Sawyers C L. Overriding imatinib resistance with a novel ABL kinase inhibitor. Science. 2004; 305:399-401.
5. Fabbro D, Ruetz S, Bodis S, et al. PKC412-a protein kinase inhibitor with a broad therapeutic potential. Anticancer Drug Des. 2000; 15:17-28.
6. Lennert K, Parwaresch M R. Mast cells and mast cell neoplasia: a review. Histopathology 1979; 3:349-365.
7. Metcalfe D D. Classification and diagnosis of mastocytosis: current status. J Invest Dermatol 1991; 96:2 S-4S.
8. Valent P. Biology, classification and treatment of human mastocytosis. Wien Klin Wschr. 1996; 108:385-397.
9. Valent P, Akin C, Sperr W R, et al. Diagnosis and treatment of systemic mastocytosis: state of the art. Br J Haematol 2003; 122:695-717.
10. Akin C, Metcalfe D D. Systemic mastocytosis. Annu Rev Med. 2004; 55:419-32.
11. Tefferi A, Pardanani A. Clinical, genetic, and therapeutic insights into systemic mast cell disease. Curr Opin Hematol. 2004; 11:58-64.
12. Valent P, Ghannadan M, Akin C, et al. On the way to targeted therapy of mast cell neoplasms: identification of molecular targets in neoplastic mast cells and evaluation of arising treatment concepts. Eur J Clin Invest. 2004; 34:41-52.
13. Nagata H, Worobec A S, Oh C K, et al. Identification of a point mutation in the catalytic domain of the protooncogene c-kit in peripheral blood mononuclear cells of patients who have mastocytosis with an associated hematologic disorder. Proc Natl Acad Sci (USA). 1995; 92:10560-10564.
14. Longley B J, Tyrrell L, Lu S Z, et al. Somatic c-kit activating mutation in urticaria pigmentosa and aggressive mastocytosis: establishment of clonality in a human mast cell neoplasm. Nat. Genet. 1996; 12:312-314.
15. Longley B J, Metcalfe D D, Tharp M, Wang X, Tyrrell L, Lu S-Z, et al. Activating and dominant inactivating c-kit catalytic domain mutations in distinct forms of human mastocytosis. Proc Natl Acad Sci (USA). 1999; 96:1609-1614.
16. Fritsche-Polanz R, Jordan J H, Feix A, et al. Mutation analysis of C-KIT in patients with myelodysplastic syndromes without mastocytosis and cases of systemic mastocytosis. Br J. Haematol. 2001; 113:357-364.
17. Feger F, Ribadeau Dumas A, Leriche L, Valent P, Arock M: Kit and c-kit mutations in mastocytosis: a short overview with special reference to novel molecular and diagnostic concepts. Int Arch Allergy Immunol. 2002; 127: 110-114.
18. Furitsu T, Tsujimura T, Tono T, et al. Identification of mutations in the coding sequence of the proto-oncogene c-kit in a human mast cell leukemia cell line causing ligand-independent activation of the c-kit product. J Clin Invest. 1993; 92:1736-1744.
19. Tefferi A, Pardanani A. Systemic mastocytosis: current concepts and treatment advances. Curr Hematol Rep. 2004; 3:197-202.
20. Akin C, Brockow K, D'Ambrosio C, et al. Effects of tyrosine kinase inhibitor STI571 on human mast cells bearing wild-type or mutated forms of c-kit. Exp Hematol 2003; 31:686-692.
21. Ma Y, Zeng S, Metcalfe D D, et al. The c-KIT mutation causing human mastocytosis is resistant to STI571 and other KIT kinase inhibitors; kinases with enzymatic site mutations show different inhibitor sensitivity profiles than wild-type kinases and those with regulatory type mutations. Blood 2002; 99:1741-1744.
22. Frost M J, Ferrao P T, Hughes T P, Ashman L K. Juxtamembrane mutant V560GKit is more sensitive to Imatinib (STI571) compared with wild-type c-kit whereas the kinase domain mutant D816VKit is resistant. Mol Cancer Ther. 2002; 1:1115-1124.
23. Akin C, Fumo G, Yavuz A S, Lipsky P E, Neckers L, Metcalfe D D. A novel form of mastocytosis associated with a transmembrane c-kit mutation and response to imatinib. Blood. 2004; 103:3222-3225.
24. Pardanani A, Ketterling R P, Brockman S R, Flynn H C, Paternoster S F, Shearer B M, Reeder T L, Li C Y, Cross N C, Cools J, Gilliland D G, Dewald G W, Tefferi A. CHIC2 deletion, a surrogate for FIP1L1-PDGFRA fusion, occurs in systemic mastocytosis associated with eosinophilia and predicts response to imatinib mesylate therapy. Blood. 2003; 102:3093-3096.
25. Pardanani A, Elliott M, Reeder T, Li C Y, Baxter E J, Cross N C, Tefferi A. Imatinib for systemic mast-cell disease. Lancet. 2003; 362:535-536.
26. Pardanani A, Tefferi A. Imatinib targets other than bcr/abl and their clinical relevance in myeloid disorders. Blood. 2004; 104:1931-1939.
27. Weisberg E, Manley P W, Breitenstein W, et al. Characterization of AMN107, a selective inhibitor of native and mutant Bcr-Abl. Cancer Cell. 2005; 7:129-141.
28. Butterfield J H, Weiler D, Dewald G, Gleich G J. Establishment of an immature mast cell line from a patient with mast cell leukemia. Leuk Res. 1988; 12:345-355.
29. Sillaber C, Strobl H, Bevec D, et al. IL-4 regulates c-kit proto-oncogene product expression in human mast and myeloid progenitor cells. J. Immunol. 1991; 147:4224-4228.
30. Mayerhofer M, Gleixner K, Aichberger K, et al. c-kit gene mutation D816V as a single hit explains numerous features and the pathology of indolent systemic mastocytosis. manuscript submitted.
31. Daley G Q, Baltimore D. Transformation of an interleukin 3-dependent hematopoietic cell line by the chronic myelogenous leukemia-specific P210bcr/abl protein. Proc Natl Acad Sci (USA). 1988; 85:9312-9316.
32. Sillaber C, Gesbert F, Frank D A, Sattler M, Griffin J D. STAT5 activation contributes to growth and viability in Bcr/Abl-transformed cells. Blood. 2000; 95:2118-2125.
33. Valent P, Horny H-P, Escribano L, et al. Diagnostic criteria and classification of mastocytosis: a consensus proposal. Conference Report of "Year 2000 Working Conference on Mastocytosis". Leuk Res. 2001; 25:603-625.
34. Valent P, Horny H-P, Li C Y, et al. Mastocytosis (Mast cell disease). World Health Organization (WHO) Classification of Tumours. Pathology & Genetics. Tumours of Haematopoietic and Lymphoid Tissues. eds: Jaffe E S, Harris N L, Stein H, Vardiman J W. 2001; 1:291-302.
35. Yavuz A S, Lipsky P E, Yavuz S, Metcalfe D D, Akin C. Evidence for the involvement of a hematopoietic progenitor cell in systemic mastocytosis from single-cell analysis of mutations in the c-kit gene. Blood. 2002; 100:661-665.
36. Valent P, Akin C, Sperr W R, Horny H P, Metcalfe D D. Smouldering mastocytosis: a novel subtype of systemic mastocytosis with slow progression. Int Arch Allergy Immunol. 2002; 127:137-139.
37. Broudy V C, Lin N, Zsebo K M, et al. Isolation and characterization of a monoclonal antibody that recognizes the human c-kit receptor. Blood. 1992; 79:338-346.
38. Bühring H J, Ashman L K, Gattei V, Kniep B, Larregina A, Pinto A, Valent P, van den Oord J. Stem-cell factor receptor (p145(c-kit)) summary report (CD117). in Leucocyte Typing V. White Cell Differentiation Antigens. eds: Schlossmann S F, Boumsell L, Gilks W, et al. Vol 2. pp 1882-1888. Oxford University Press. 1995.
39. Chou T C, Talalay P. Quantitative analysis of dose-effect relationships: the combined effects of multiple drugs or enzyme inhibitors. Adv Enzyme Regul 1984; 22:27-55.
40. Van Cruchten S, Van Den Broeck W. Morphological and biochemical aspects of apoptosis, oncosis and necrosis. Anat Histol Embryol 2002; 31:214-223.
41. Schedle A, Samorapoompichit P, Fjireder W, et al. Metal ion-induced toxic histamine release from human basophils and mast cells. J Biomed Mater Res. 1998; 39:560-567.
42. Samorapoompichit P, Kiener H P, Schemthaner G H, et al. Detection of tryptase in cytoplasmic granules of basophils in patients with chronic myeloid leukemia and other myeloid neoplasms. Blood. 2001; 98:2580-2583.
43. Gorczyca W, Gong J, Darzynkiewicz Z. Detection of strand breaks in individual apoptotic cells by the in situ terminal deoxynucleotidal transferase and nick translation assays. Cancer Res. 1993; 53:1945-1951.
44. Walker P R, Carson C, Leblanc J, Sikorska M. Labeling DNA damage with terminal transferase. Applicability, specificity, and limitations. Methods Mol. Biol. 2002; 203: 3-19.

45. Escribano L, Diaz-Agustin B, Bellas C, et al. Utility of flow cytometric analysis of mast cells in the diagnosis and classification of adult mastocytosis. Leuk Res. 2001; 25:563-570.
46. Valent P, Schernthaner G H, Sperr W R, et al. Variable expression of activation-linked surface antigens on human mast cells in health and disease. Immunol Rev. 2001; 179: 74-81.
47. Ghannadan M, Hauswirth A W, Schemthaner G H, et al. Detection of novel CD antigens on the surface of human mast cells and basophils. Int Arch Allergy Immunol. 2002; 127:299-307.
48. Growney J D, Clark J J, Adelsperger J, et al. Activation mutations of human c-KIT resistant to imatinib are sensitive to the tyrosine kinase inhibitor PKC412. Blood. 2005, in press.
49. Corless C L, Fletcher J A, Heinrich M C. Biology of gastrointestinal stromal tumors. J Clin Oncol. 2004; 22:3813-3825.
50. Cowan-Jacob S W, Guez V, Fendrich G, et al. Imatinib (STI571) resistance in chronic myelogenous leukemia: molecular basis of the underlying mechanisms and potential strategies for treatment. Mini Rev Med. Chem. 2004; 4:285-299.
51. Weisberg E, Griffin J D. Resistance to imatinib (Glivec): update on clinical mechanisms. Drug Resist Updat. 2003; 6:231-238.
52. Gotlib J, Berube C, Ruan J, et al. PKC412, inhibitor of the KIT tyrosine kinase, demonstrates efficacy in mast cell leukemia with the D816V KIT mutation. Blood. 2003; 102:919a (abst).

Example 2

Combination of Dasatinib and PKC412

In a majority of all patients with systemic mastocytosis (SM) including aggressive SM and mast cell leukemia (MCL), neoplastic cells display the D816V-mutated variant of KIT. KIT-D816V exhibits constitutive tyrosine kinase (TK) activity and has been implicated in malignant cell-growth. Therefore, several attempts have been made to identify KIT-D816V-targeting drugs. We find that the TK-inhibitor dasatinib (BMS-354825) counteracts TK-activity of wild type (wt) KIT and KIT-D816V in Ba/F3 cells with doxycycline-inducible KIT-expression. In addition, dasatinib is shown to inhibit KIT D816V-induced cluster formation and viability in Ba/F3 cells as well as growth of HMC-1.1 cells (KIT-D816V-negative) and HMC-1.2 cells (KIT-D816V-positive). The effects of dasatinib are dose-dependent, with 100-1.000-fold higher IC50-values in those harbouring KIT-D816V compared to cells lacking KIT-D816V. Inhibitory effects of dasatinib in HMC-1 cells are found to be associated with apoptosis and a decrease in CD2- and CD63-expression. In addition, dasatinib is found to cooperate with PKC412, AMN107, imatinib, and 2CdA in producing growth-inhibition. In HMC-1.1 cells, all drug-interactions applied are found to be synergistic. By contrast, in HMC-1.2, only the combinations "dasatinib+PKC412" and "dasatinib+2CdA" produce synergistic effects. These drug-combinations may thus represent an interesting pharmacologic approach for the treatment of aggressive SM or MCL.

Introduction

Receptor tyrosine kinases such as the platelet derived growth factor receptor (PDGFR) or stem cell factor receptor (SCFR, KIT), are often deregulated and show constitutive tyrosine kinase (TK) activity in patients with hematopoietic neoplasms.[1-5] These molecules thus represent attractive targets for drug therapy. In fact, during the past few years, several emerging treatment concepts have been based on novel drugs targeting critical TK in neoplastic myeloid cells.[1-5]

Systemic mastocytosis (SM) is a myeloid neoplasm characterized by abnormal growth and accumulation of neoplastic mast cells (MC) in one or more organs. Indolent as well as aggressive variants of SM have been described.[6-9] In patients with aggressive SM (ASM) and those who are suffering from the leukemic variant of SM, i.e. mast cell leukemia (MCL), the response to conventional drugs is poor and the prognosis is grave.[6-12] Therefore, a number of attempts have been made to identify new therapeutic targets in neoplastic MC and to develop respective treatment concepts.[9-12]

In most patients suffering from SM including those with ASM or MCL, the KIT mutation D816V is detectable.[13-17] This mutation is associated with ligand-independent phosphorylation of KIT as well as autonomous growth of cells.[17,18] Based on this notion, the D816V-mutated variant of KIT has been recognized as a major target of therapy.[9-12,19] Thus, a number of efforts have been made to identify TK-inhibitors that counteract phosphorylation of KIT-D816V and growth of neoplastic MC.[9-12,19-24] Imatinib (STI571), a potent inhibitor of BCR/ABL, has recently been described to counteract growth of neoplastic MC exhibiting wild-type (wt) KIT or the rarely occurring F522C-mutated variant of KIT.[20-23] In addition, this drug was found to block growth of neoplastic cells in patients who have chronic eosinophilic leukemia with FIP1L1/PDGFRA fusion gene with or without co-existing SM.[24-26] However, imatinib failed to inhibit the growth of neoplastic MC harbouring KIT D816V.[20-22] More recently, we and others have shown that PKC412[27] counteracts the TK activity of KIT-D816V, and thereby downregulates growth of neoplastic MC.[28-30] It has also been described that the novel TK inhibitor AMN10731 counteracts the growth of neoplastic cells exhibiting KIT-D816V at relatively high drug concentrations.[30-32] However, most of these compounds may not produce long lasting complete remission in patients with ASM or MCL, at least as single agents. Moreover, as mentioned above, several of these drugs act only on MC exhibiting wt KIT, but do not inhibit growth of MC harbouring KIT-D816V. Therefore, it is of importance to further search for novel KIT-targeting TK inhibitors and to examine cooperative drug-effects. With regard to drug-combinations, we have recently shown that PKC412 and AMN107 produce cooperative growth-inhibitory effects in HMC-1 cells.[30] However, whereas this drug combination produced synergistic inhibitory effects in HMC-1 cells lacking KIT-D816V, no synergistic effect was observed in HMC-1.2 cells expressing KIT-D816V.[30] Other drug combinations also failed to exert synergistic inhibitory effects in mast cells exhibiting KIT-D816V.[30]

Dasatinib (BMS-354825) is a novel inhibitor of src kinases and of several TK inhibitors including KIT.[33,34] It has also been described that dasatinib inhibits phosphorylation of KIT-D816V and the growth of neoplastic MC.[34,35] In the current study, we show that dasatinib blocks several of the KIT-D816V-dependent disease-related functions in neoplastic cells including survival and cluster formation as well as expression of CD2 and CD63. In addition, our data show that dasatinib synergizes with PKC412 as well as with 2CdA in producing growth inhibition in HMC-1.2 cells. To the best of our knowledge this is the first combination of TK inhibitors described to act synergistic on MC harbouring KIT-D816V. Our data also suggest that dasatinib alone or in combination with other drugs, may be a promising agent for the treatment of patients with ASM or MCL.

Materials and Methods

Reagents

Dasatinib (BMS-354825)33 was provided by Bristol-Myers Squibb (New Brunswick, N.J.), and imatinib (STI571), AMN107,[31] and PKC412[27] by Novartis Pharma AG (Basel, Switzerland). Stock solutions of dasatinib, AMN107, and PKC412 were prepared by dissolving in dimethyl-sulfoxide (DMSO) (Merck, Darmstadt, Germany). Recombinant human (rh) stem cell factor (SCF) was purchased from Strathmann Biotech (Hannover, Germany), RPMI 1640 medium and fetal calf serum (FCS) from PAA laboratories (Pasching, Austria), L-glutamine and Iscove's modified Dulbecco's medium (IMDM) from Gibco Life Technologies (Gaithersburg, Md.), 3H-thymidine from Amersham (Buckinghamshire, UK), 2-chloro-deoxyadenosine (cladribine=2CdA) from Sigma (St. Louis, Mo.), and rh interleukin-4 (IL-4) from Peprotech (Rocky Hill, N.J.). The PE-labeled monoclonal antibodies (mAbs) RPA-2.10 (CD2), WM15 (CD13), YB5.B8 (CD117), and N6B6.2 (CD164) as well as MOPC-21 (mIgG1) and G155-178 (mIgG2a) were purchased from Becton Dickinson (San Jose, Calif.), and the PE-conjugated mAb CLB-gran12 (CD63) from Immunotech (Marseille, France). The PE-labeled mAb VIM5 (CD87) was kindly provided by Dr. Otto Majdic (Institute of Immunology, Medical University of Vienna, Austria).

HMC-1 Cells Expressing or Lacking KIT D816V

The human mast cell line HMC-1[36] generated from a patient with MCL, was kindly provided by Dr. J. H. Butterfield (Mayo Clinic, Rochester, Minn.). Two subclones of HMC-1 were used, namely HMC-1.1 harbouring the KIT mutation V560G but not KIT D816V,20 and a second subclone, HMC-1.2, harbouring both KIT mutations, i.e. V560G and D816V.[20] HMC-1 cells were grown in IMDM supplemented with 10% FCS, L-glutamine, alpha-thioglycerol (Sigma) and antibiotics at 37° C. and 5% $CO_2$. Cells were re-thawed from an original stock every 4-8 weeks and passaged weekly. HMC-1 cells were periodically checked for i) the presence of metachromatic granules, ii) expression of KIT, and iii) the down-modulating effect of IL-4 (100 U/ml, 48 hours) on KIT-expression.[37]

BA/F3 Cells with Inducible Expression of wt KIT or KIT D816V

The generation of Ba/F3 cells with doxycycline-inducible expression of wt c-KIT (Ton.Kit.wt) or c-KIT D816V has been described previously.[30,38] In brief, Ba/F3 cells expressing the reverse tet-transactivator[39-40] were co-transfected with pTRE2 vector (Clontech, Palo Alto, Calif.) containing KIT D816V cDNA (or wt KIT cDNA, both kindly sent by Dr. J. B. Longley, Columbia University, New York, USA) and pTK-Hyg (Clontech) by electroporation. Stably transfected cells were selected by growing in hygromycin and cloned by limiting dilution. In this study, the subclone Ton.Kit.D816V.2738 was used in all experiments. Expression of KIT-D816V can be induced in these cells (within 12 hours) by exposure to doxycycline (1 μg/ml).[38]

Isolation of Primary Neoplastic Cells

Primary bone marrow (bm) cells were obtained from one patient with KIT D816V-positive ASM and associated AML and one patient with normal bm. The bm aspirate samples were collected in syringes containing preservative-free heparin. Cells were layered over Ficoll to isolate mononuclear cells (MNC). Cell viability was >90% in both cases. In the patient with ASM-AML, isolated MNC were found to contain >90% blast cells. Both patients gave written informed consent before bm puncture or blood donation. The study was approved by the local institutional review board and was conducted in accordance with the declaration of Helsinki.

Analysis of KIT Phosphorylation by Western Blotting

HMC-1 cells (10[6]/ml), and Ton.Kit.D816V.27 cells (10[6]/ml) containing either wt KIT (Ton.Kit.wt) or KIT D816V (Ton.Kit.D816V.27), were incubated with dasatinib (1 μM, 1 nM, 10 nM, 100 nM, 1 μM), PKC412 (1 μM), AMN107 (1 μM), imatinib (1 μM), or control medium at 37° C. for 4 hours. Prior to exposure to inhibitory drugs, Ton.Kit.wt cells and Ton.Kit.D816V.27 cells were incubated with doxycycline (1 μg/ml) at 37° C. for 24 hours to induce expression of KIT. In case of Ton.Kit.wt cells, KIT phosphorylation was induced by adding rhSCF (100 ng/ml). Immunoprecipitation (IP) and Western blotting were performed as described.[30,40] In brief, cells were washed at 4° C. and resuspended in RIPA buffer (1 ml buffer per 108 cells) containing 50 mM Tris, 150 mM NaCl, 1% nonidet P40 (NP-40), 0.25% deoxycholic acid, 0.1% sodium dodecyl sulfate (SDS), 1 mM ethylenediamine-tetraacetic acid (EDTA), 1 mM NaF, 1 mM phenylmethylsulfonyl fluoride and 1 mM Na3VO4. After incubation in RIPA buffer supplemented with proteinase inhibitor cocktail (Roche) for 30 minutes at 4° C., lysates were centrifuged. For IP, lysates from 10[7] cells were incubated with anti-KIT antibody 1C1 (kindly provided by Dr. H.-J. Bühring, University of Tübingen, Germany)43 and protein G Sepharose-beads (Amersham) in IP-buffer (50 mM Tris-Cl, pH 7.4, 150 mM NaCl, 100 mM NaF, and 1% NP-40) at 4° C. overnight. Beads were then washed 3 times in IP buffer. Lysates and immunoprecipitates were separated under reducing conditions by 7.5% SDS-polyacrylamide gel electrophoresis and transferred to a nitrocellulose membrane (Protran, Schleicher & Schuell, Keene, N.H.) in buffer containing 25 mM Tris, 192 mM glycine, and 20% methanol at 4° C. Membranes were blocked for 1 hour in 5% blocking reagent (Roche) and were then incubated with anti-KIT antibody 1C1 or with anti-phospho-protein mAb 4G10 (Upstate Biotechnology, Lake Placid, N.Y.) at 4° C. overnight. Antibody-reactivity was made visible by sheep anti-mouse IgG antibody and Lumingen PS-3 detection reagent (both from Amersham), with CL-Xposure film (Pierce Biotechnology, Rockford, Ill.).

Evaluation of Drug Effects on Growth and Function of Ton.Kit.D816V.27 Cells

Ton.Kit.D816V.27 cells were co-incubated with doxycycline (1 μg/ml) and various concentrations of dasatinib or AMN107 at 37° C. for 24-48 hours. Cell viability was determined by trypan blue exclusion. Cluster formation was analyzed by inverted microscope. Previous studies have shown that expression of KIT-D816V in Ton.Kit.D816V.27 is associated with significant cluster formation, and that PKC412, but not imatinib, downregulates cluster formation in Ton.Kit.D816V.27 cells.[38] In the present study the effects of dasatinib (1 μM-1 μM) and AMN107 on cluster formation of Ton.Kit.D816V.27 cells were analyzed. For control purpose, the effects of PKC412 and imatinib were also examined. Cluster formation was determined by light microscopy (counted as cluster per high power field=HPF) and expressed as percent of control (=doxycycline alone without drugs=100%). All experiments were performed in triplicates.

Measurement of 3H-thymidine Uptake

To determine growth-inhibitory drug effects, HMC-1 cells were incubated with various concentrations of dasatinib (100 fM-10 μM), PKC412 (100 pM-10 μM), AMN107 (1 nM-100 μM), or imatinib (3 nM-300 μM) in 96-well culture plates (TPP, Trasadingen, Switzerland) at 37° C. for 48 hours. In time course experiments, HMC-1 cells were exposed to dasatinib (HMC-1.1:10 nM; HMC-1.2:1 μM) for 12, 24, 36, or 48 hours. In select experiments, HMC-1 cells were incubated with various concentrations of 2CdA (0.005-10 µg/ml). Primary cells (bm cells from a patient with ASM-AML; control bm cells) were cultured in control medium, dasatinib (100 pM-10 µM), PKC412 (100 pM-10 µM), AMN107 (100 pM-10 µM), or imatinib (100 pM-10 µM) for 48 hours. After incubation, 1 µCi 3H-thymidine was added (37° C., 12 hours). Cells were then harvested on filter membranes (Packard Bioscience, Meriden, Conn.) in a Filtermate 196 harvester (Packard Bioscience). Filters were air-dried, and the bound radioactivity was counted in a β-counter (Top-Count NXT, Packard Bioscience). To determine potential additive or synergistic drug-effects on cell growth, HMC-1 cells (both subclones) were exposed to various combinations of drugs (dasatinib, PKC412, AMN107, imatinib, 2CdA) at fixed ratio of drug-concentrations. Drug-interactions (additive, synergistic) were determined by calculating combination index (CI) values using Calcusyn software (Calcusyn; Biosoft, Ferguson, Mo.).[44] A CI value of 1 indicates an additive effect, whereas CI values below 1 indicate synergism of drug effects. All experiments were performed in triplicates.

Evaluation of Apoptosis by Conventional Morphology and Electron Microscopy

The effects of TK-inhibitors on apoptosis were analyzed by morphologic examination, flow cytometry, and electron microscopy. In typical experiments, HMC-1 cells were incubated with various concentrations of dasatinib (1 pM-1 µM) or control medium in 6-well culture plates (TPP) in IMDM containing 10% FCS at 37° C. for 24 hours. The percentage of apoptotic cells was quantified on Wright-Giemsa-stained cytospin preparations. Apoptosis was defined according to conventional cytomorphological criteria.[45] To confirm apoptosis in HMC-1 cells, electron microscopy was performed as described[46,47] using HMC-1 cells (both subclones) exposed to dasatinib (1 pM, 1 nM, 10 nM, 100 nM, 1 µM), PKC412 (1 µM), or control medium for 24 hours. After incubation, cells were washed and fixed in 2% paraformaldehyde, 2.5% glutaraldehyde, and 0.025% CaCl2 buffered in 0.1 mol/L sodium cacodylate buffer (pH 7.4) for 1 hour. Cells were then washed, suspended in 2% agar, and centrifuged. Pellets were post-fixed with 1.3% OsO4 (buffered in 0.66 mol/L collidine) and stained 'en bloc' in 2% uranyl acetate and sodium maleate buffer (pH 4.4) for 2 hours. Pellets were then rinsed, dehydrated in alcohol series and embedded in EPON 812. Ultrathin sections were cut and placed on gold grids. Sections were contrasted in uranyl acetate and lead citrate, and viewed in a JEOL 1200 EX II transmission electron microscope (JEOL, Tokyo, Japan).

Evaluation of Apoptosis by Tunel Assay

To confirm apoptosis in HMC-1 cells after exposure to dasatinib (1 pM, 1 nM, 10 nM, 100 nM, 1 µM) or PKC412 (100 nM, 1 µM), a Tunel (in situ Terminal transferase-mediated dUTP-fluorescence Nick End-Labeling) assay was performed using "In Situ Cell Death Detection Kit Fluorescein" (Roche Diagnostics, Mannheim, Germany) according to the instructions of the manufacturer. In brief, cells were placed on cytospins, fixed in 4% paraformaldehyde in PBS at pH 7.4 at RT for 60 minutes, washed and then permeabilized in 0.1% Triton X-100 and 0.1% sodium citrate. Thereafter, the cells were washed and incubated in the terminal-transferase reaction-solution containing $CoCl_2$, terminal deoxy-nucleotidyl-transferase, and fluorescein labeled dUTP for 60 minutes at 37° C. Cells were then washed and analyzed with a Nikon Eclipse E 800 fluorescence microscope (Tokyo, Japan).

Evaluation of Expression of Activation-Linked Surface Antigens on HMC-1 Cells

Expression of cell surface antigens on HMC-1 cells (both subclones) was determined by flow cytometry after culture in control medium or medium supplemented with TK inhibitors (dasatinib, 1 pM-5 µM; PKC412, 1 µM) at 37° C. for 24 hours. After incubation with drugs, cells were washed and subjected to single-color flow cytometry using PE-conjugated antibodies against several MC differentiation antigens including determinants known to be aberrantly (selectively) expressed on neoplastic MC.[48-51] The markers analyzed were CD2, CD13, CD63, CD87, CD117, and CD164. Flow cytometry was performed on a FACScan (Becton Dickinson) as described.[30,37,51]

Statistical Analysis

To determine significance of differences between proliferation rates, apoptosis, and surface expression-levels after exposure of HMC-1 cells to inhibitors, the students t test for dependent samples was applied. Results were considered statistically significant when p was <0.05.

Results

Effects of Dasatinib on TK Activity of Kit-D816V

Figure 11A:
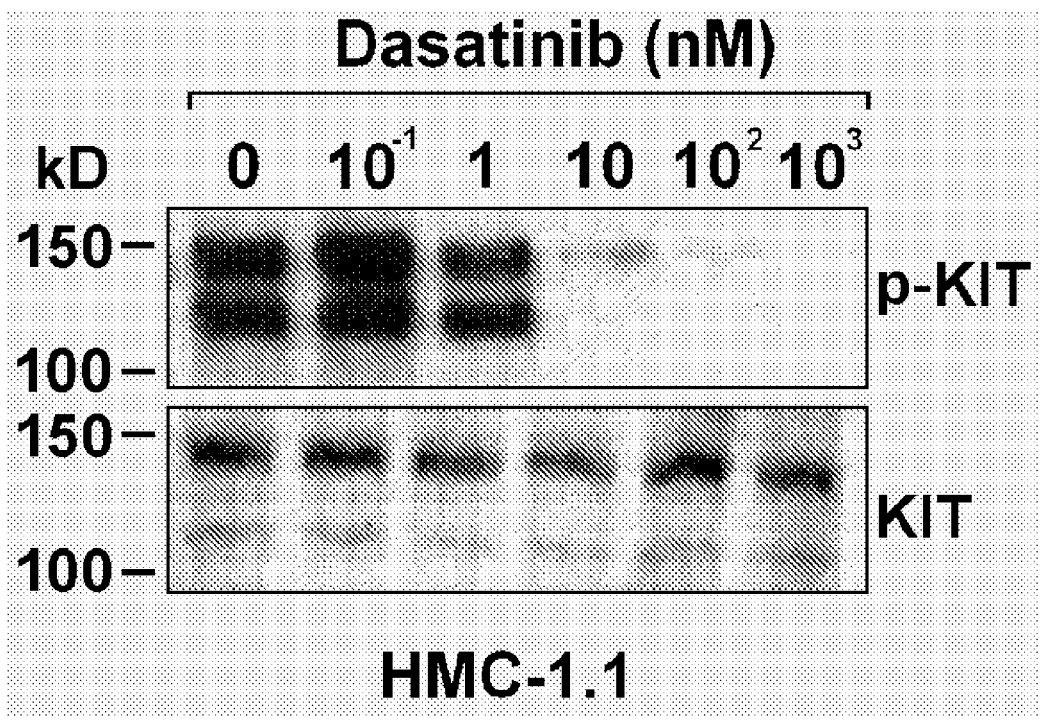
FIG. 11A-D is a representation of the effects of dasatinib on KIT phosphorylation in neoplastic cells.
Figure 11B:
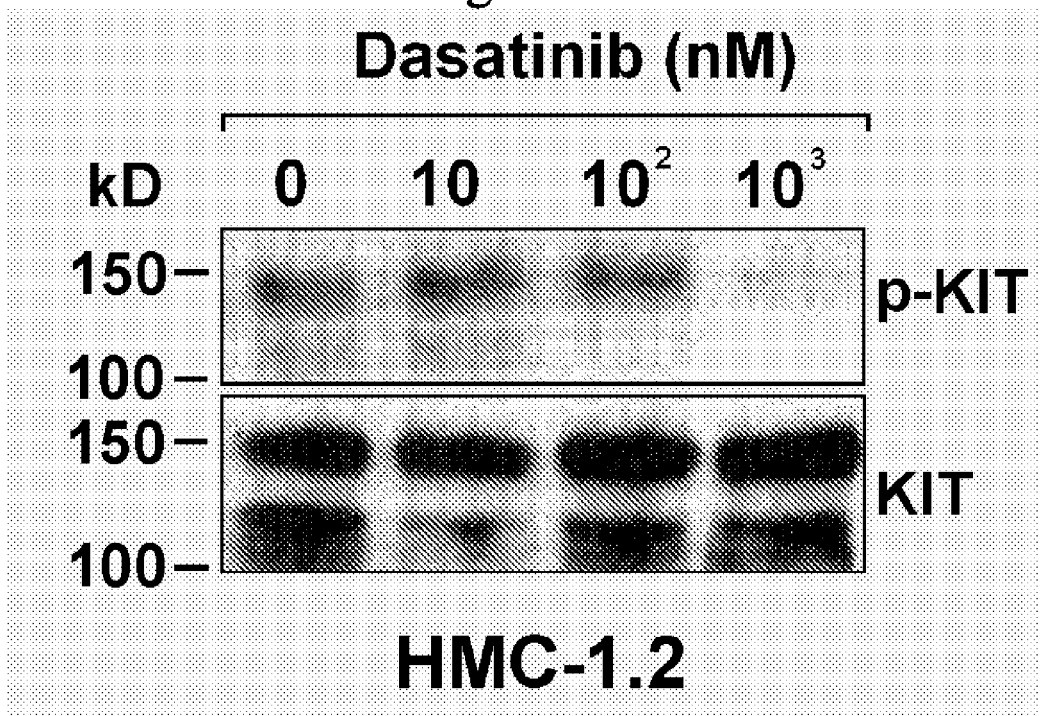
Figure 11C:
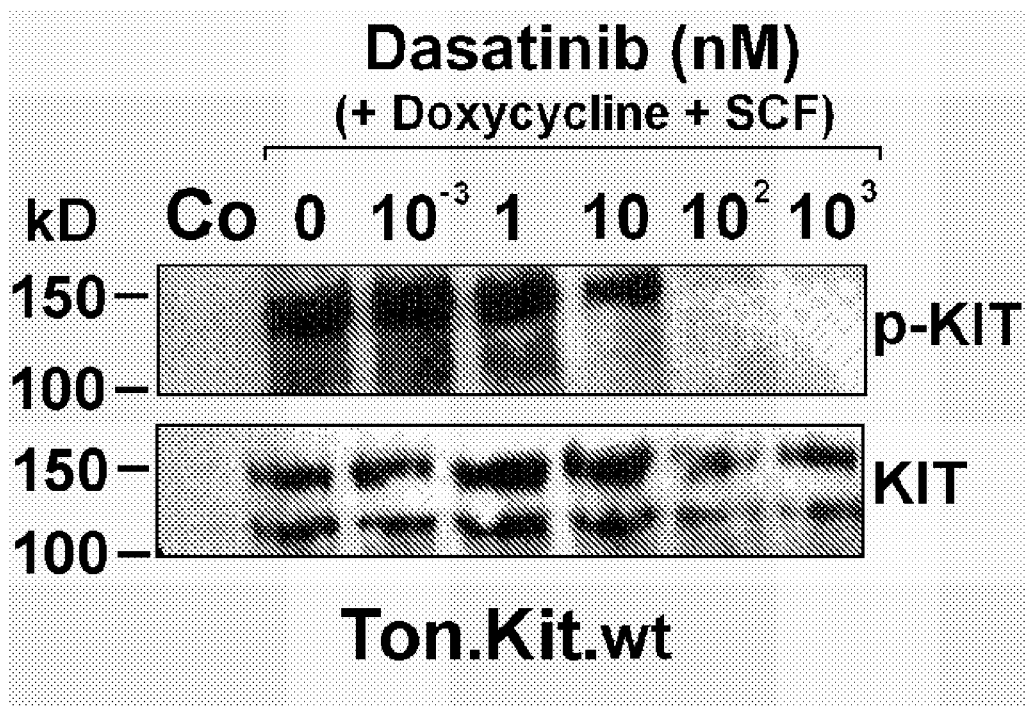
Figure 11D:
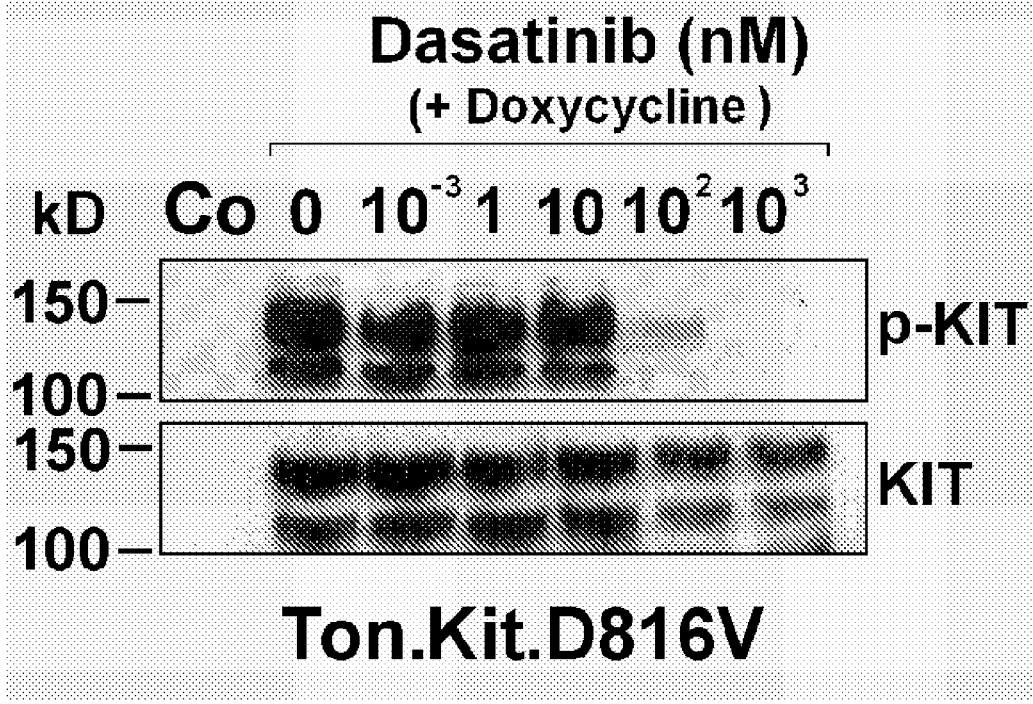

As assessed by IP and Western blotting, dasatinib (1 nM-1 µM) decreased the phosphorylation of KIT in HMC-1.1 cells (expressing KIT-V560G but not KIT D816V) (FIG. 11A). In HMC-1.2 cells harbouring both mutations (KIT-V560G and KIT-D816V), dasatinib decreased the phosphorylation of KIT at 1 µM, but did not counteract phosphorylation of KIT at lower concentrations (FIG. 11B). We next examined the effects of dasatinib on Ba/F3 cells expressing either wt KIT (Ton.Kit.wt) or KIT D816V (Ton.Kit.D816V.27) after exposure to doxycycline. In Ton.Kit.wt cells, KIT appeared to be phosphorylated in the presence of SCF, whereas KIT was found to be constitutively phosphorylated in Ton.Kit.D816V.27 cells. As visible in FIG. 11C, dasatinib (10 nM-1 µM) decreased the SCF-induced phosphorylation of KIT in Ton.Kit.wt cells. By contrast, in Ton.Kit.D816V.27 cells (expressing KIT-D816V after exposure to doxycycline), dasatinib decreased the phosphorylation of KIT at 0.1 and 1 µM, but failed to decrease KIT-phosphorylation at lower concentrations (FIG. 11D).

Effects of TK-Inhibitors on 3H-thymidine Uptake in HMC-1 Cells

Figure 12A:
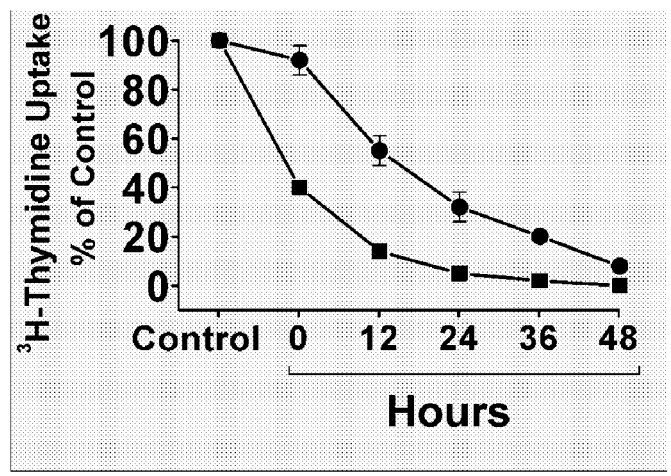
FIG. 12A-F is a representation of the effects of dasatinib on proliferation of HMC-1 cells and growth and cluster formation of BaF/3 cells.
Figure 12B:
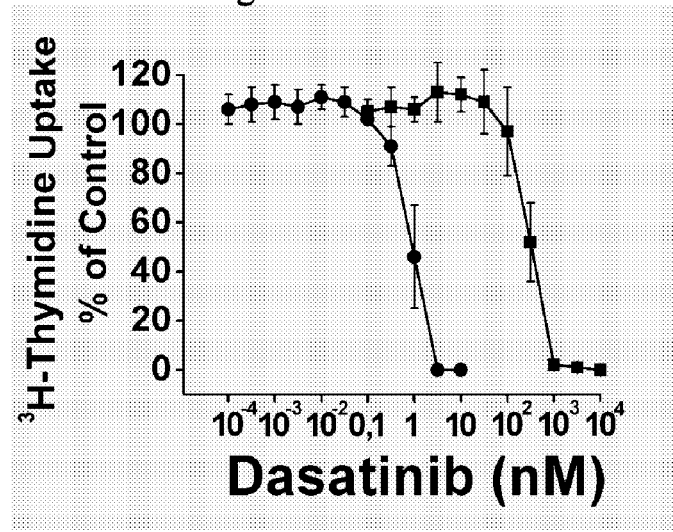
Figure 17:
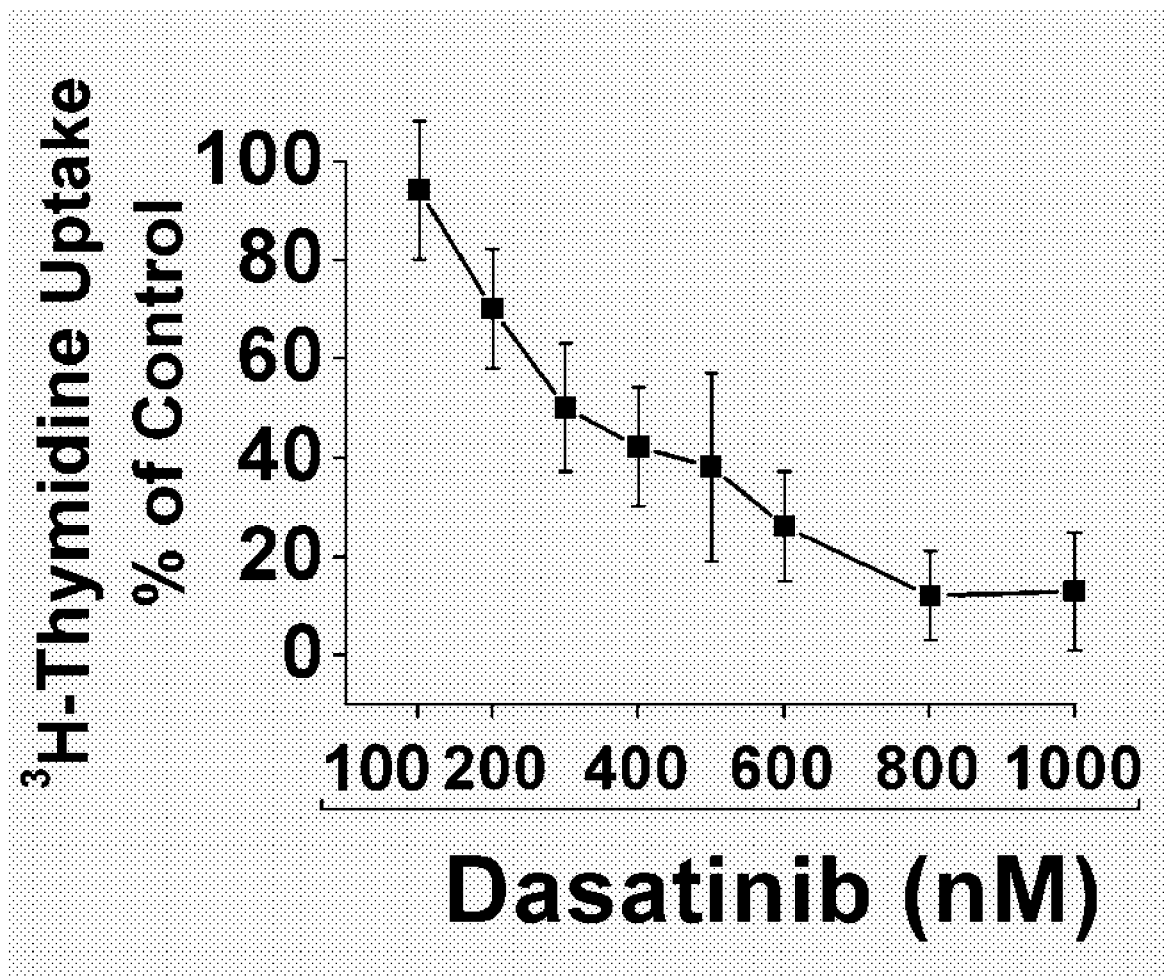
FIG. 17 represents HMC-1.2 cells that were incubated with control medium or various concentrations of dasatinib as indicated at 37° C. for 48 hours. Thereafter, uptake of $^3$H-thymidine was measured. Results are expressed as percent of control (cells kept in control medium=100%) and represent the mean±S.D. of three independent experiments.

In time-course experiments, maximum inhibitory effects of dasatinib on growth of HMC-1.1 cells and HMC-1.2 cells were seen after 36-48 hours. FIG. 12A shows the time-dependent effects of dasatinib (10 nM for HMC-1.1 cells; 1 µM for HMC-1.2 cells) on growth of these cells. As shown in FIG. 12B, dasatinib was found to counteract 3H-thymidine uptake in HMC-1.1 cells and HMC-1.2 cells in a dose-dependent manner. Interestingly, the IC50 for the effects of dasatinib in HMC-1.2 cells (200-500 nM) was considerably higher compared to the IC50 values obtained for HMC-1.1 cells (1 nM) (FIG. 12B; FIG. 17). Nevertheless, dasatinib was found to inhibit the growth of HMC-1.2 cells much more effectively on a molar basis compared to imatinib (tested in parallel). Table 2 shows a summary of the IC50 values obtained for the effects of TK inhibitors applied on HMC-1.1 cells and HMC-1.2 cells. With regard to effects of imatinib, AMN107, and PKC412, these data confirmed previous results.[30]

TABLE 2

Effects of targeted drugs ($IC_{50}$) on $^3$H-thymidine uptake in HMC-1 cells

|  | HMC-1.1 | HMC-1.2 |
| --- | --- | --- |
| Dasatinib | 0.1 nM-3 nM | 200 nM-500 nM |
| Imatinib | 10 nM-30 nM | 10 µM-30 µM |
| PKC412 | 50 nM-250 nM | 50 nM-250 nM |
| AMN107 | 3 nM-10 nM | 1 µM-5 µM |
| 2CdA | 100 ng/ml-300 ng/ml | 10 ng/ml-20 ng/ml |

Effects of TK-Inhibitors on Growth of Ba/F3 Cells Expressing wt Kit or KIT D816V (Ton.KIT.D816V.27)

Figure 12C:
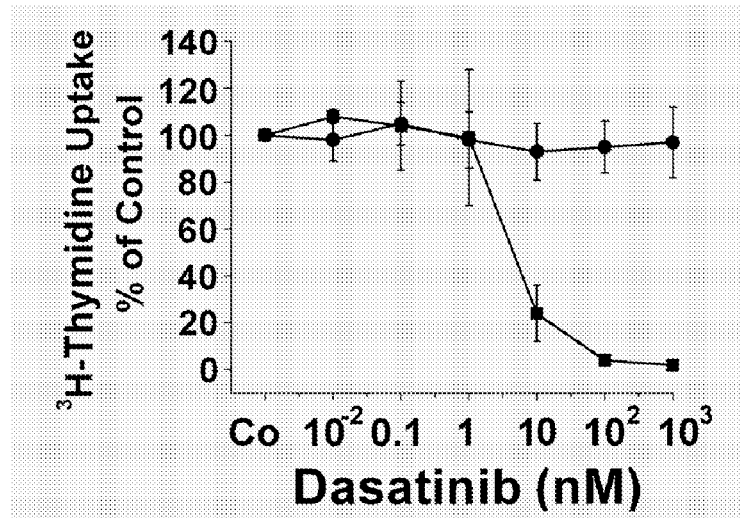
Figure 12D:
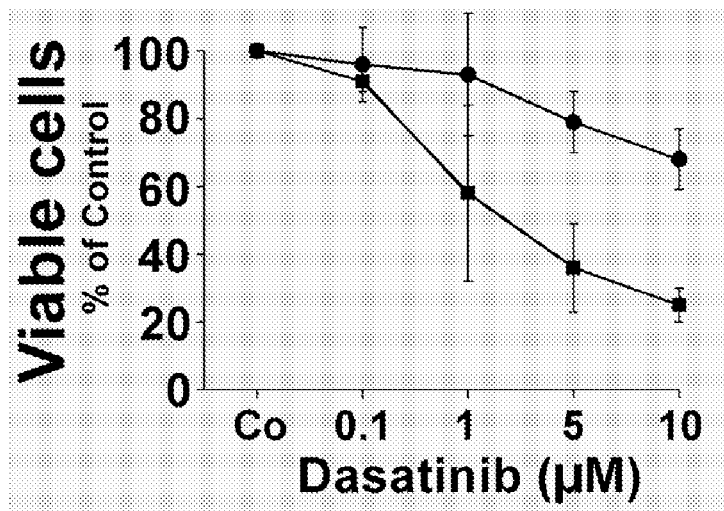

Dasatinib was found to counteract SCF-dependent growth of doxycycline-exposed (KIT-expressing) Ton.Kit.wt cells in a dose-dependent manner (IC50: 1 nM-10 nM) (FIG. 12C). In Ton.Kit.D816V.27 cells, dasatinib was also found to inhibit growth and cell viability (FIG. 12D). Dasatinib did not counteract growth of Ton.Kit.wt cells in the absence of doxycycline, i.e. in the absence of KIT (FIG. 12C). Similarly, dasatinib did not produce major growth inhibitory effects in Ton.Kit.D816V.27 cells in the absence of KIT D816V (-doxycycline) (FIG. 12D). In addition, in further control experiments, doxycycline (1 μg/ml) did not show growth-inhibitory effects on non-transfected Ba/F3 cells (not shown).

Figure 12E:
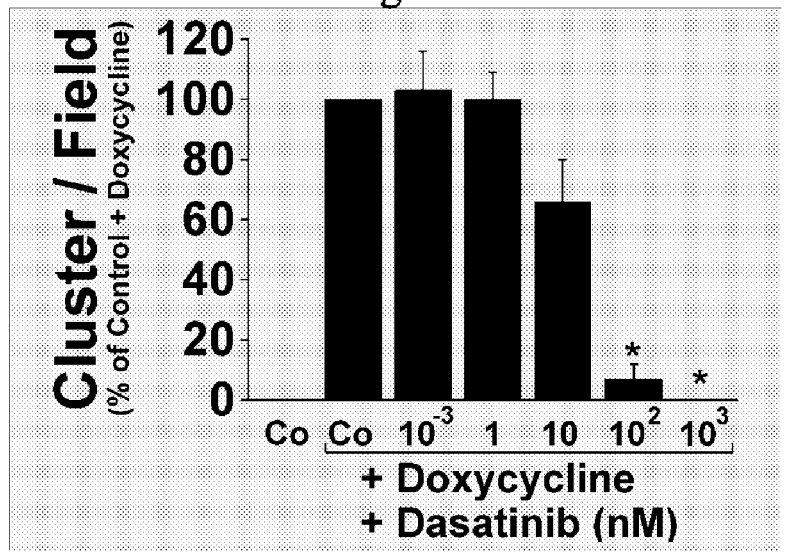
Figure 12F:
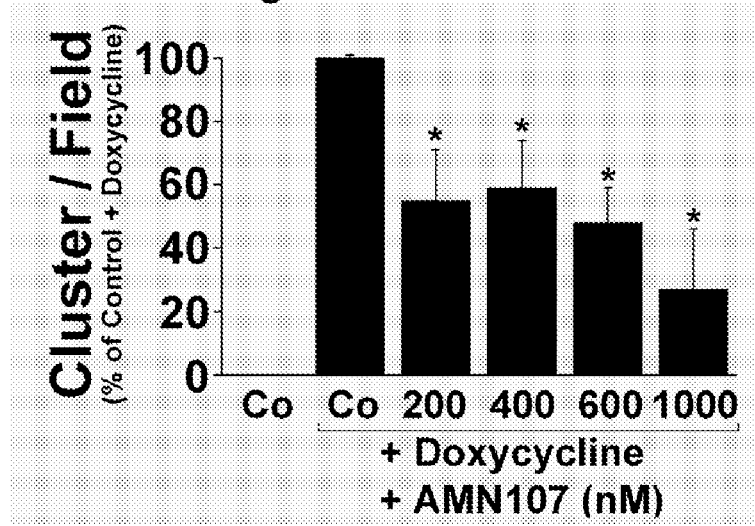

Effects of Dasatinib and AMN107 on Kit-D816V-Dependent Cluster Formation in Ton.Kit.D816V.27 cells We have previously shown that KIT-D186V induces not only mast cell differentiation but also cluster formation in Ba/F3 cells, which is of particular interest since cluster formation of mast cells is a primary finding and major disease-criterion in SM.[38] It has also been described, that PKC412 downregulates doxycycline/KIT-D816V-induced cluster formation in Ton.Kit.D816V.27 cells.[38] In the present study, we found that dasatinib (100 nM-1 μM) and to a lesser degree, AMN107 (200 nM-1 μM), counteract KIT-D816V-dependent cluster formation in Ba/F3 cells in a dose-dependent manner (FIGS. 12E and 12F).

Figure 13:
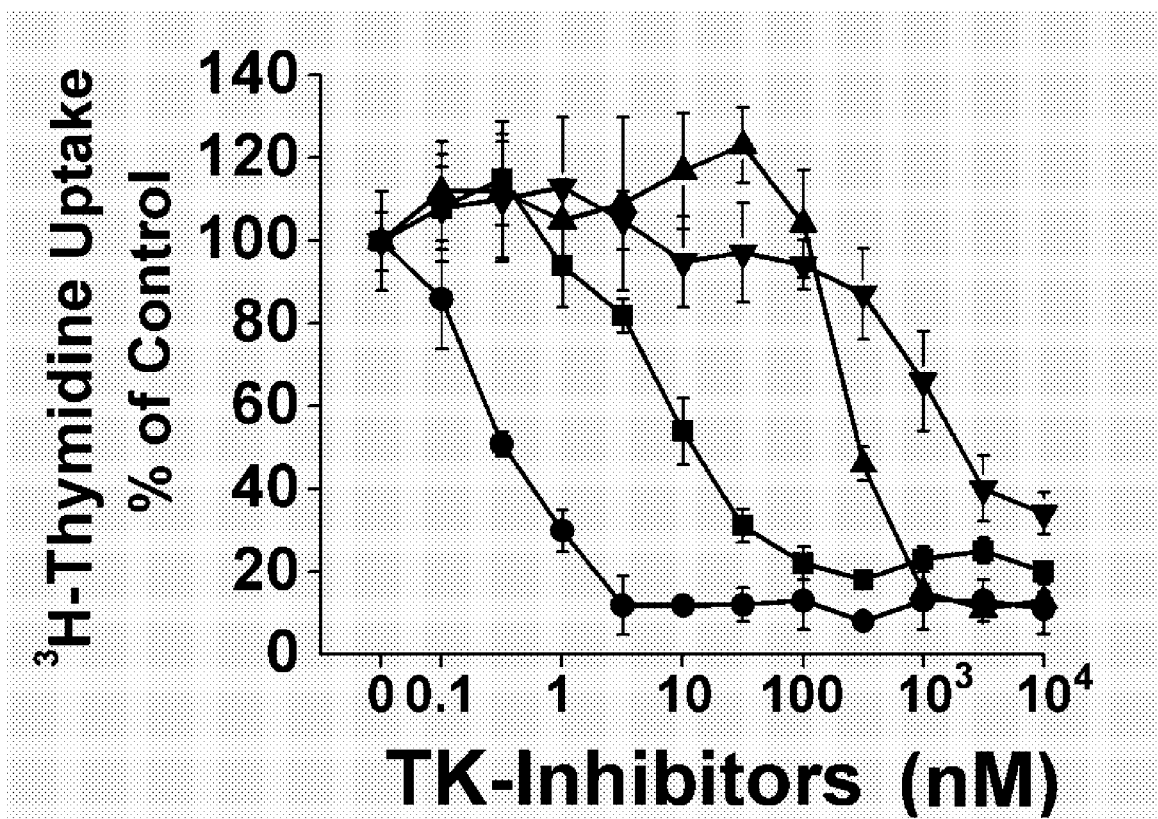
FIG. 13 is a representation that dasatinib downregulates growth of primary neoplastic cells in a patient with KIT D816V-positive SM with associated leukemia. Primary neoplastic bone marrow cells were isolated from a patient with KIT D816V-positive ASM associated with AML. Isolated cells were incubated in control medium or in various concentrations of dasatinib (●-●), PKC412 (■-■), AMN107 (▲-▲), or imatinib (▼-▼), as indicated. Cell growth was quantified by measuring 3H-thymidine uptake. Results are expressed as percent of control (cells kept in control medium=100%) and represent the mean±S.D. of triplicates. In normal bone marrow cells, no effects of the TK inhibitors applied were seen (not shown).

Dasatinib Counteracts Growth of Primary Neoplastic Cells in a Patient with KIT D816V-Positive SM with Associated AML To confirm anti-proliferative drug effects of dasatinib in SM, we examined primary neoplastic cells in a patient with KIT D816V-positive ASM associated with AML. In this patient, dasatinib (IC50: 0.3-1.0 nM) as well as PKC412 (IC50: 10-30 nM) were found to inhibit the spontaneous growth (uptake of 3H-thymidine) of leukemic cells in a dose-dependent manner. AMN107 also showed a growth-inhibitory effect (100-300 nM), whereas imatinib (IC50>1.0 μM) did not counteract growth of neoplastic cells in this patient (FIG. 13). In the control sample i.e. in normal bm cells, neither dasatinib nor the other inhibitors tested showed an effect on 3H-thymidine uptake (not shown).

Dasatinib Induces Apoptosis in HMC-1 Cells

Figure 14A:
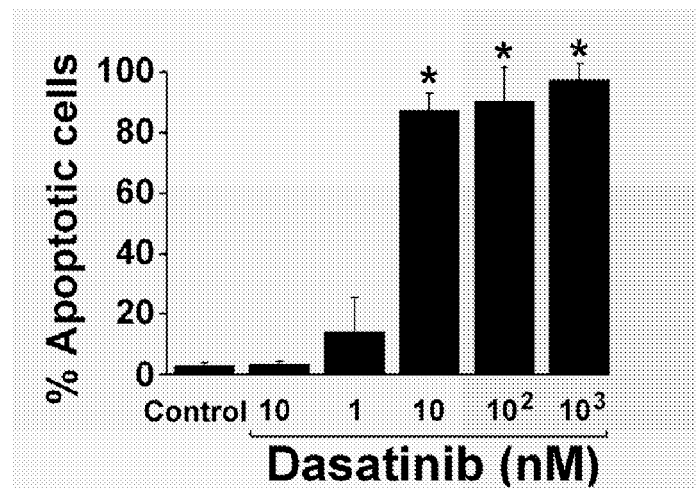
FIG. 14A-C represents that dasatinib induces apoptosis in HMC-1 cells.
Figure 14B:
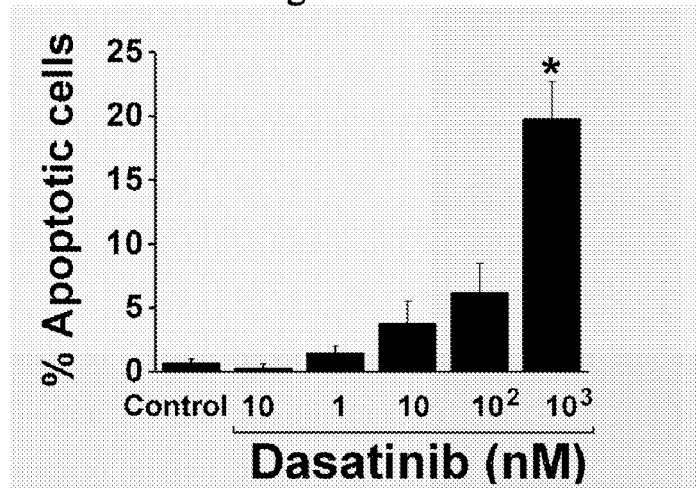
Figure 14C:
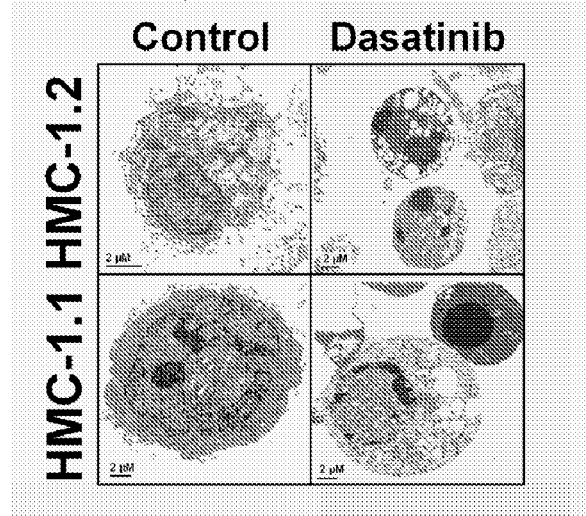

To explore the mechanism underlying the growth-inhibitory effect of dasatinib, we analyzed morphological and biochemical signs of apoptosis in HMC-1 cells after drug-exposure. As assessed by light microscopy, dasatinib was found to induce apoptosis (i.e. to increase the number of apoptotic cells) in both HMC-1 subclones (FIGS. 14A and 14B). PKC412 was applied as control and was also found to induce apoptosis in both HMC-1 subclones, whereas imatinib was found to produce apoptosis in HMC-1.1 cells, but showed no effects on HMC-1.2 cells (not shown). The apoptosis-inducing effect of dasatinib on HMC-1 cells was confirmed by electron microscopy. In fact, dasatinib induced apoptosis in both HMC-1.1 cells and HMC-1.2 at 1 μM (FIG. 14C). Finally, we were able to demonstrate the apoptosis-inducing effect of dasatinib in HMC-1 cells in a Tunel assay (FIGS. 14D and 14E). In this assay, dasatinib was found to induce apoptosis in HMC-1.1 cells between 1 and 1,000 nM, and to induce apoptosis in HMC-1.2 cells between 100 and 1,000 nM. PKC412 (1 μM) was run in parallel as a control, and also induced apoptosis in both cell lines (FIGS. 14D and 14E). By contrast, imatinib (1 μM) induced apoptosis only in HMC-1.1 cells but showed no effects on HMC-1.2 cells (not shown) confirming previous data.[30]

Figure 15A:
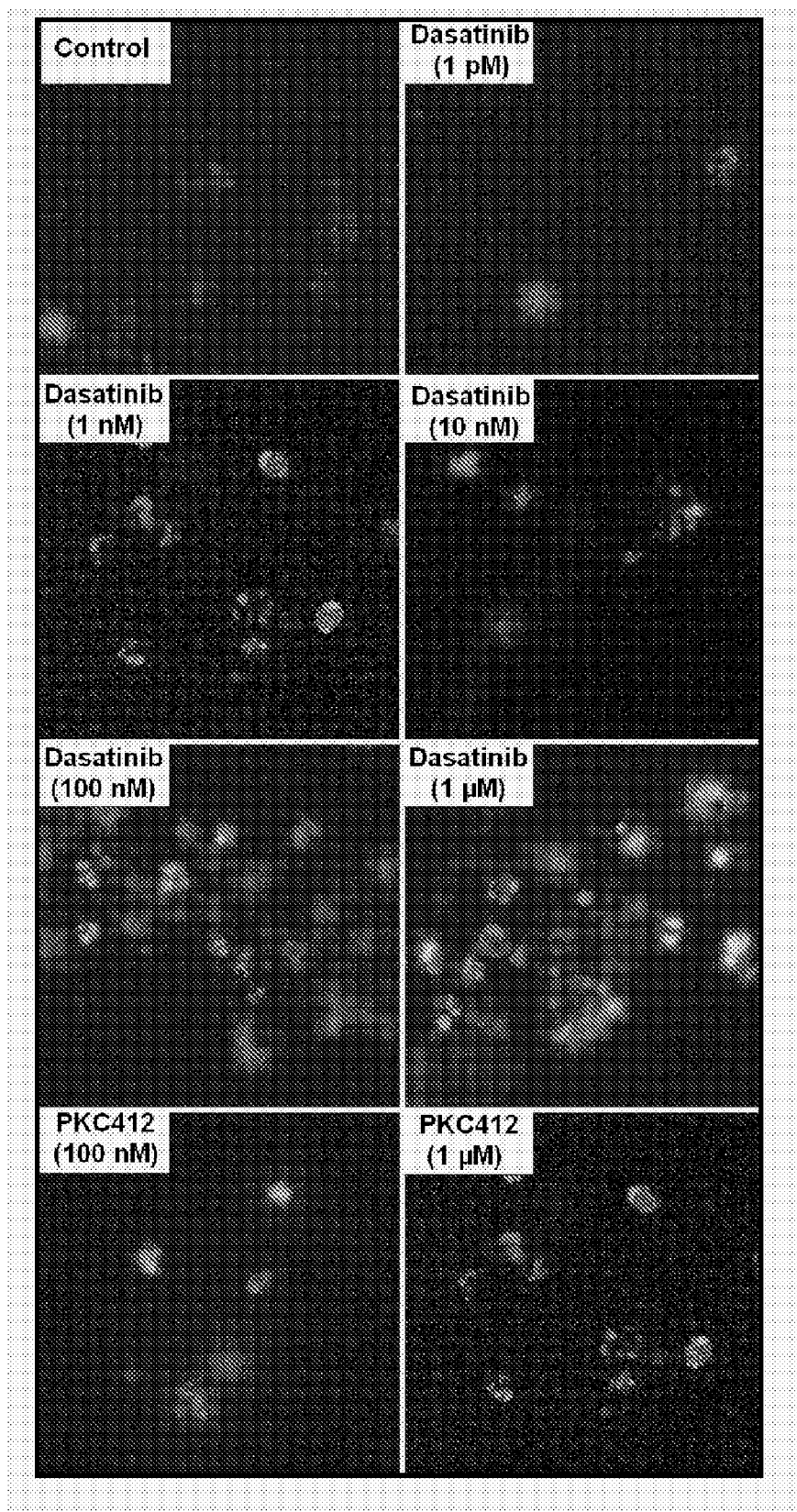
FIG. 15A-F represents the effects of dasatinib on expression of cell surface antigens on HMC-1 cells.
Figure 15B:
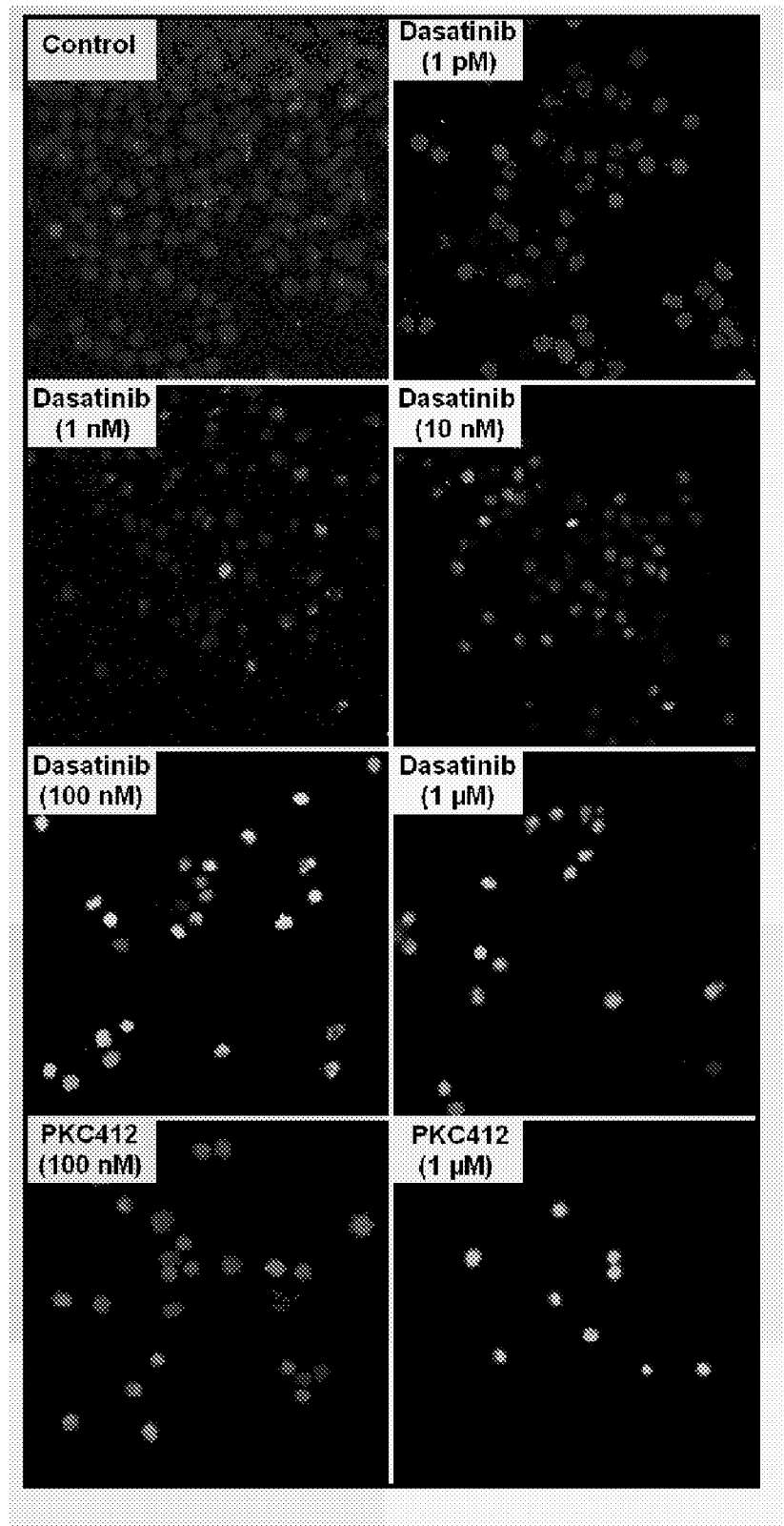
Figure 15C:
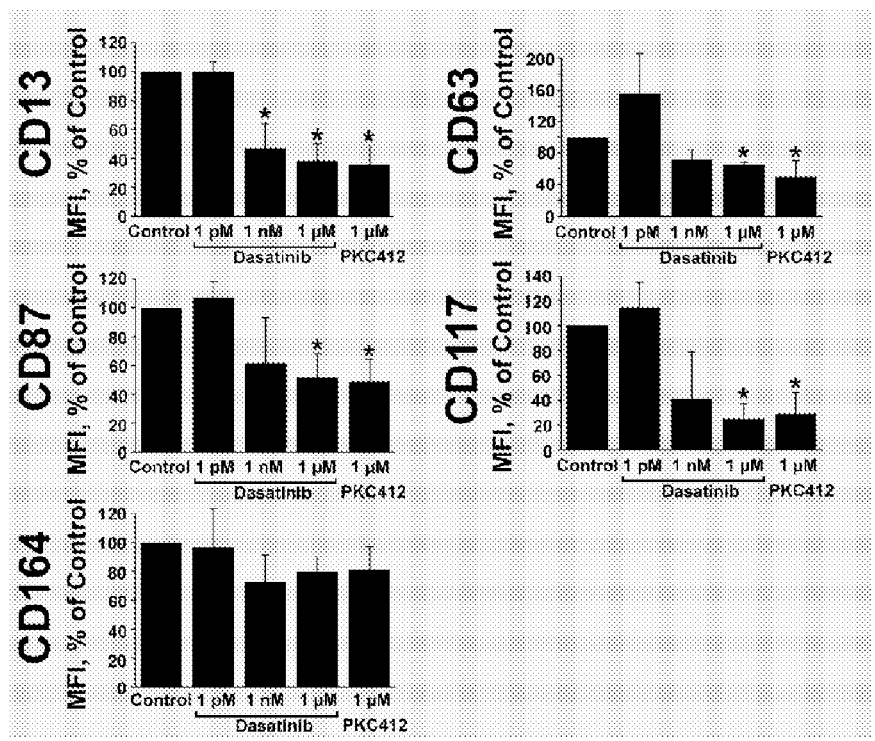
Figure 15D:
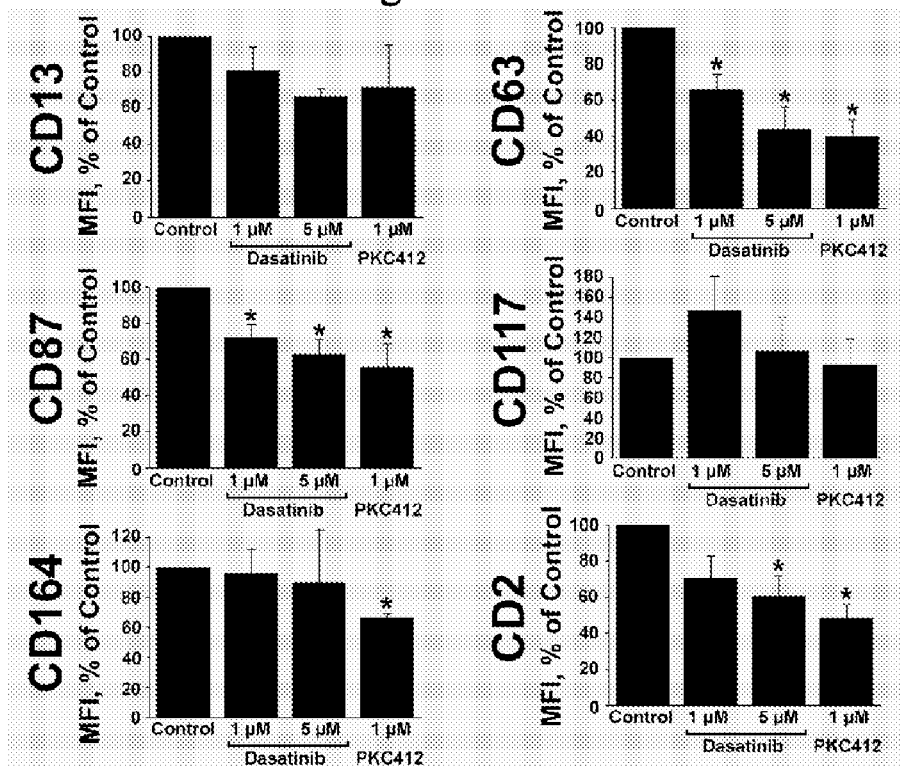
Figure 15E:
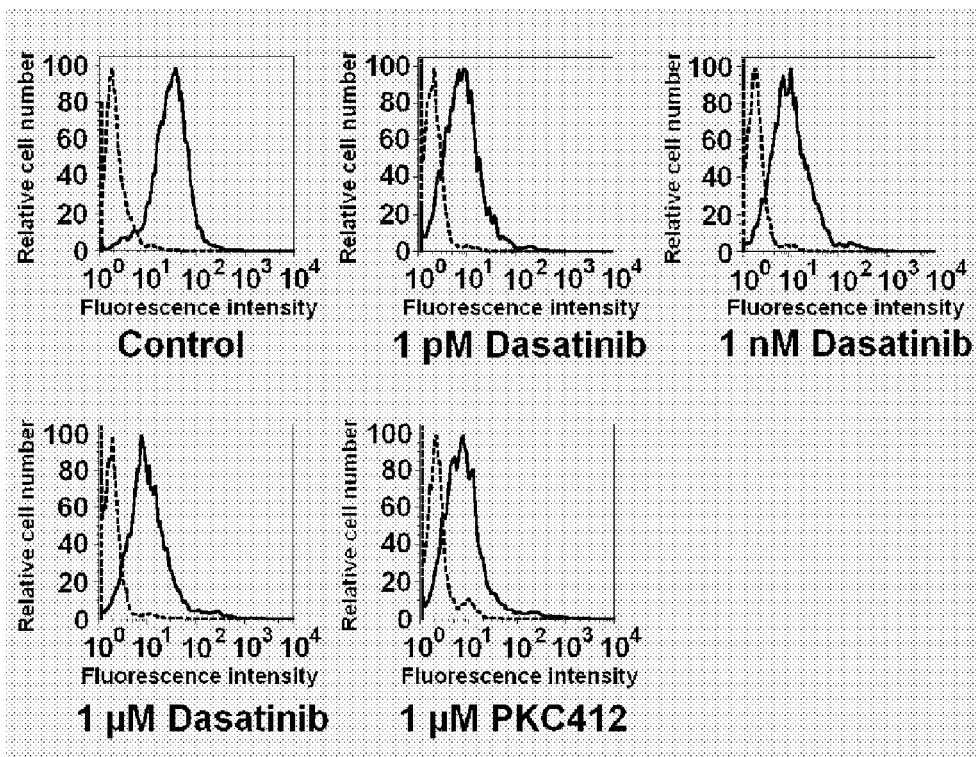
Figure 15F:
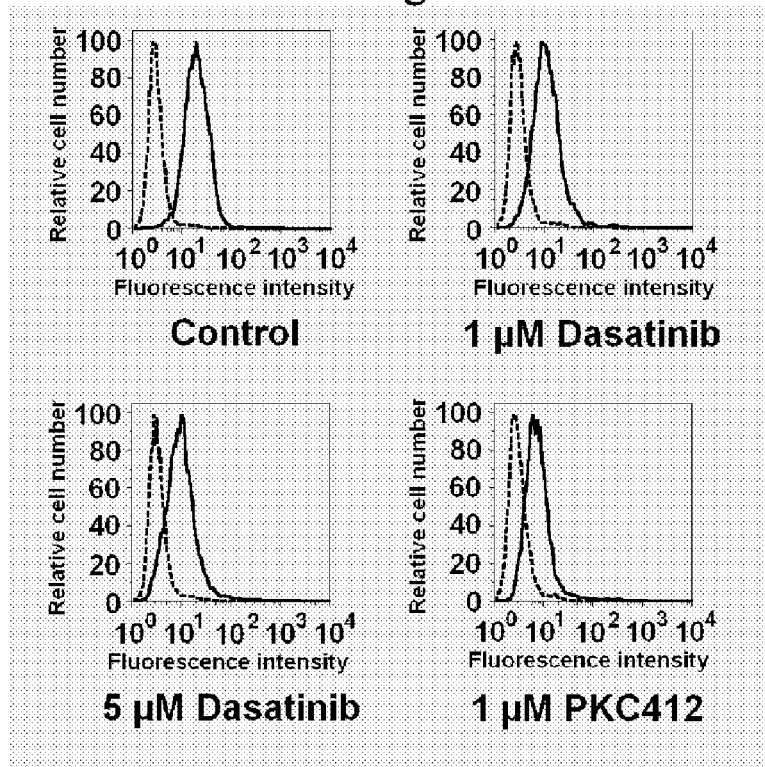
Figure 16A:
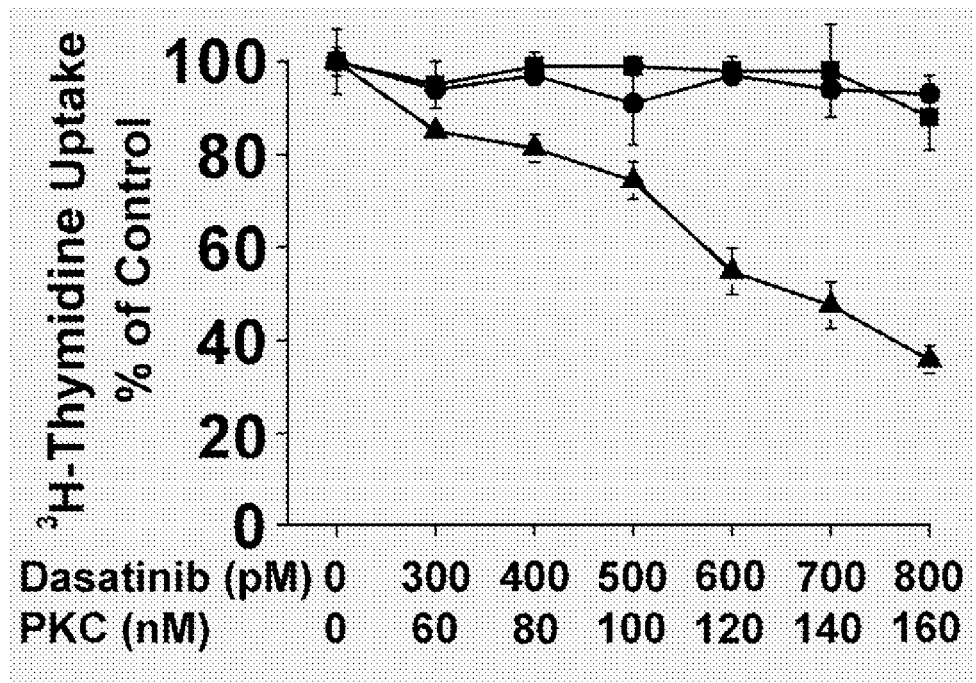
FIG. 16A-D represent synergistic drug effects on growth of HMC-1 cells. HMC-1.1 cells (FIG. 16A-B) and HMC-1.2 cells exhibiting KIT D816V (FIG. 16C-D) were incubated with single drugs or various drug combinations (at fixed ratio) at 37° C. for 48 hours before determining uptake of 3H-thymidine.
Figure 16B:
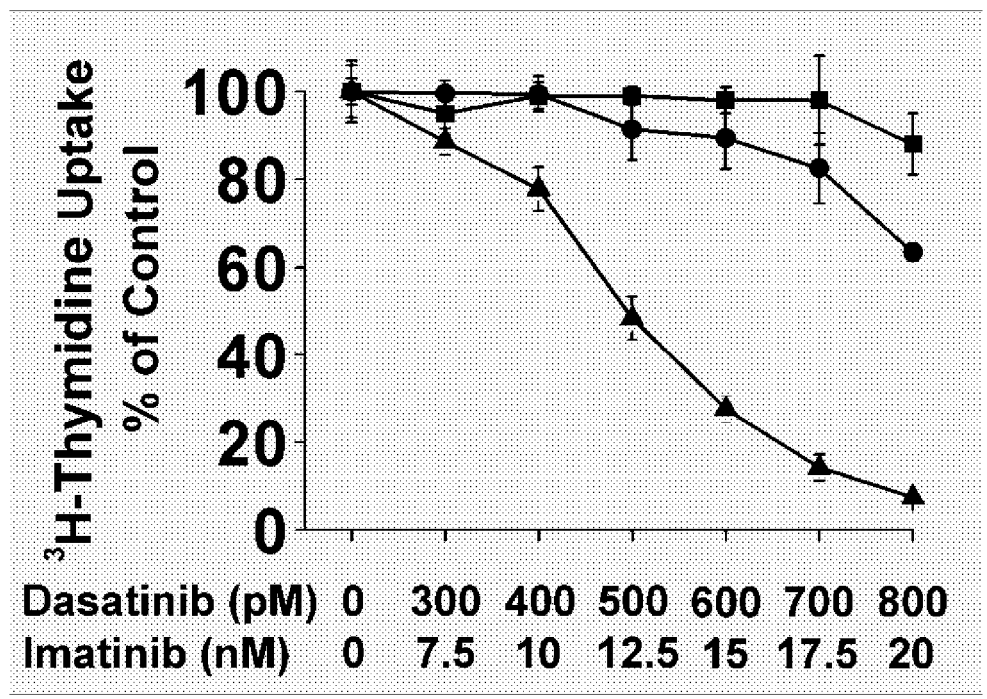
Figure 16C:
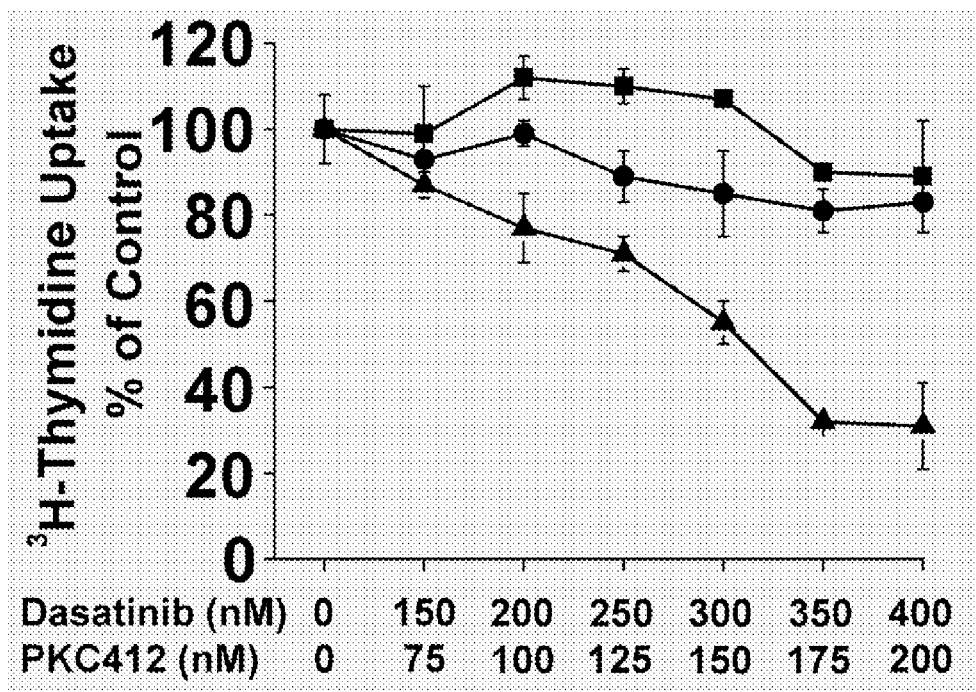
Figure 16D:
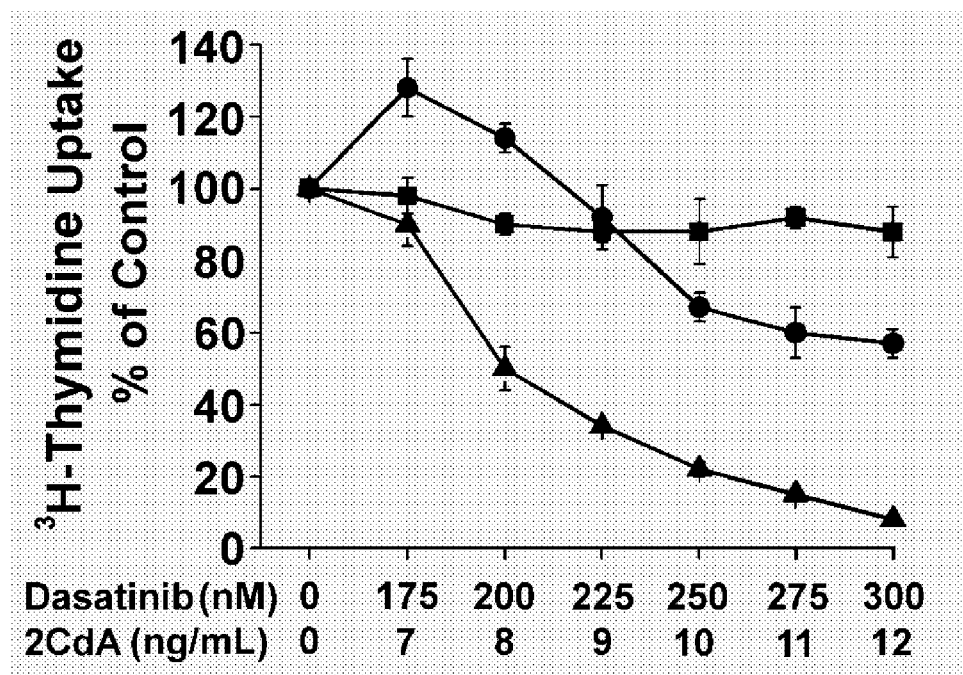

Dasatinib Downregulates Expression of Activation-Linked Cell Surface Antigens on HMC-1 Cells Several cell surface antigens such as CD2 or CD63 are typically (over)expressed on neoplastic MC in SM.[48-50] Interestingly, some of these molecules may be expressed in neoplastic MC in a KIT D816V-dependent manner[38] or/and are expressed at an early stage of human mast cell development.[51] We therefore investigated whether dasatinib would influence expression of these surface antigens on HMC-1 cells. Unstimulated HMC-1.1 cells were found to express CD13, CD63, CD87, CD117, and CD164, and HMC-1.2 cells expressed CD2, CD13, CD63, CD87, CD117, and CD164, confirming previous data.[30,38,50] Incubation of HMC-1.1 cells with dasatinib resulted in a significant decrease in expression of CD13, CD63, CD87, and CD117 (p<0.05) (FIG. 15C). In HMC-1.2 cells, dasatinib significantly decreased the expression of CD2, CD63, and CD87 (p<0.05), but did not lead to a significant decrease in expression of CD13, CD117, or CD164 (FIG. 15D). The downregulating effects of dasatinib in flow cytometry experiments are exemplified for CD63 in FIGS. 15E (HMC-1.1) and FIG. 15D (HMC-1.2).

Dasatinib Cooperates with Other TK Inhibitors and with 2CdA in Producing Growth Inhibition 1N HMC-1 Cells As assessed by 3H-thymidine incorporation, dasatinib was found to cooperate with PKC412, AMN107, imatinib, and 2CdA in causing growth inhibition in HMC-1 cells (Table 3, FIG. 16). In HMC-1.1 cells, all drug interactions tested were found to be synergistic in nature (FIGS. 16A and 16B). By contrast, in HMC-1.2 cells, only the combinations 'dasatinib and PKC412' and 'dasatinib and 2CdA' produced a clear synergism (FIGS. 16C and 16D), whereas the other drug combinations showed additive rather than synergistic growth-inhibitory effects on cell growth (Table 3). As shown in Table 3, cooperative drug effects on growth of HMC-1.2 cells (upper panels; grey) and HMC-1.1 cells (lower panels; dark grey) were determined by measuring uptake of $^3$H-thymidine. Cooperative drug effects were calculated by calcusyn software.

TABLE 3

Evaluation of synergistic drug effects on growth of HMC-1 cells

|  | Dasatinib | Imatinib | PKC412 | AMN107 | 2CdA |
|---|---|---|---|---|---|
| Dasatinib |  | ± | + | ± | + |
| Imatinib |  |  | n.t. | ± | n.t. |
| PKC412 |  |  |  | ± | ± |
| AMN107 |  |  |  |  | ± |
| 2CdA |  |  |  |  |  |

Drug interactions: +, synergistic effects; ±, additive effects; −, antagonistic effects.

Discussion

In patients with SM, factor-independent autonomous growth and accumulation of MC are characteristic features common to all disease-variants. The somatic KIT mutation D816V is an SM-related defect considered to be responsible for constitutive activation of KIT and autonomous growth of cells.[13-17] Therefore, recent attempts have been made to identify pharmacologic compounds that inhibit the TK activity of KIT-D816V, and thus the growth/accumulation of neoplastic cells.[9-12] We describe that the novel TK inhibitor dasatinib blocks the TK activity of KIT-D816V as well as several KIT D816V-dependent disease-related functions in neoplastic cells. In addition, we show that dasatinib synergizes with PKC412 as well as with other targeted and conventional drugs in producing growth-inhibition in neoplastic MC.

Dasatinib, also known as BMS-354825, is a novel TK inhibitor that exerts profound effects on several TK including BCR/ABL and KIT, and also displays considerable activity against several src kinases.[33-35] Based on its 'TK-targeting' activity, dasatinib has recently been considered as an antineoplastic agent that may inhibit the growth of neoplastic cells in various myeloid neoplasms.[33-35] In the present study, we found that dasatinib counteracts the TK activity of the SM-related oncoprotein KIT-D816V and inhibits in vitro growth of human MC harbouring this KIT mutation, which confirms previous publications.[34,35] In addition, we found that dasatinib counteracts KIT-D816V-dependent cluster formation in Ba/F3 cells as well as the expression of CD2 and CD63 in HMC-1.2 cells. Thus, dasatinib blocks several disease (SM)-related and KIT-D816V-dependent functions in neoplastic MC. With regard to growth-inhibition, an interesting observation was that the effect of dasatinib on wt KIT or KIT G560V was more pronounced compared to that seen with KIT D816V. A similar observation has recently been made with AMN107 and imatinib.[30] However, whereas the KIT mutation D816V confers almost complete resistance against imatinib, the other two TK inhibitors, i.e. AMN107 and dasatinib, retain considerable activity against KIT D816V, with lower IC50 values obtained for dasatinib compared to AMN107 on a molar basis, which may be explained by different drug-target interactions or by the fact that dasatinib not only counteracts KIT TK activity but also several other potential targets, such as src kinases. An interesting observation was that the growth-inhibitory effects of dasatinib on HMC-1.2 cells occur at pharmacological concentrations, confirming earlier publications.[34,35]

In most instances, TK inhibitors act as growth-inhibitors by blocking TK-dependent cell growth with consecutive apoptosis.[30,35] Similarly, in case of dasatinib, we were able to show that growth inhibition of HMC-1 cells is associated with loss of TK activity and is accompanied by signs of apoptosis. Apoptosis-inducing effects of dasatinib were demonstrable by light- and electron microscopy as well as in a Tunel assay. As expected, dasatinib showed more potent apoptosis-inducing effects on HMC-1.1 cells than in HMC-1.2, which is in line with recently published results.[35]

A key feature and major WHO criterion in SM is cluster formation of MC in visceral organs.[41,42] We have recently shown that KIT D816V induces not only mast cell differentiation but also cluster formation in Ba/F3 cells.[38] Thus, MC cluster formation may be an initial and most important step in the pathogenesis of SM. In the present study we were able to show that dasatinib and AMN107 counteract KIT D816V-induced cluster formation in Ba/F3 cells. This observation provides further evidence for the specific action and effectiveness of these drugs.

Several cell surface membrane antigens are typically (over)expressed on neoplastic MC.[48-50] Likewise, in contrast to normal MC, neoplastic MC in SM express CD2 and CD25.[48-50] Moreover, several cell surface molecules such as CD63, are overexpressed on neoplastic MC compared to normal MC.[49] In some cases (like CD63), expression of CD molecules may be KIT-D816V-dependent.[38] Therefore, we asked whether targeting of KIT D816V by dasatinib would be associated with a decrease in expression of these CD antigens. The results of our study show that dasatinib downregulates expression of CD2, CD63, and CD87 in HMC-1.2 cells (exhibiting KIT D816V), whereas no significant inhibition of expression of CD13, CD117=KIT, or CD164, was found. By contrast, in HMC-1.1 cells, dasatinib was also found to downregulate expression of CD13 and KIT. One explanation for this discrepancy would be the different sensitivity (IC50) of the two HMC-1 subclones to dasatinib. An alternative possibility would be that in HMC-1.2 cells, CD13 and KIT are in general non-susceptible to drug-induced modulation. This hypothesis would be supported by the observation that CD13 and KIT were also expressed at the same levels after incubation with PKC412, although the IC50 values for this compound are identical in the two HMC-1 subclones.

A number of recent data suggest that treatment of myeloid neoplasms with TK inhibitors as a single agent may not be sufficient to control the disease for a prolonged time period. This has been documented for imatinib and advanced CML[51,52] and may also apply for patients with ASM or MCL.[29] Thus, in many of these patients, drug resistance is found. To overcome resistance, a number of pharmacological strategies may be envisaged. One reasonable approach may be to apply drug-combinations.

In a previous study, we found that PKC412, AMN107, and 2CdA exhibit potent cooperative drug effects in HMC-1 cells.[30] However, whereas synergistic effects were seen with most drug combinations in HMC-1.1 cells lacking KIT D816V, no synergistic (but only additive) drug interactions were seen in HMC-1.2 cells harbouring KIT D816V. Therefore, we were highly interested to learn whether dasatinib, which exhibits potent effects on mast cells carrying KIT D816V as single agent, would produce synergistic effects on these cells when combined with other potent inhibitors of KIT D816V. Indeed, our results show that dasatinib and PKC412 as well as dasatinib and 2CdA, a drug used to treat ASM and MCL[54], inhibit growth of HMC-1.2 cells in a synergistic manner. To the best of our knowledge, this is the first combination of TK inhibitors producing a synergistic effect on growth of neoplastic MC carrying KIT D816V.

In summary, we show that dasatinib and PKC412 are most promising targeted drugs for the treatment of ASM and MCL. Based on our data, it seems reasonable to consider the application of combinations of these drugs or combinations between these drugs and 2CdA to improve therapy in patients with ASM or MCL.

Example 2 References

1. Griffin J. The biology of signal transduction inhibition: basic science to novel therapies. Semin Oncol. 2001; 28(5S):3-8.
2. Reilly J T. Class III receptor tyrosine kinases: role in leukaemogenesis. Br J. Haematol. 2002; 116:744-757.
3. Deininger M W, Druker B J. Specific targeted therapy of chronic myelogenous leukemia with imatinib. Pharmacol Rev. 2003; 55:401-423.
4. Pardanani A, Tefferi A. Imatinib targets other than bcr/abl and their clinical relevance in myeloid disorders. Blood. 2004; 104:1931-1939.
5. Chalandon Y, Schwaller J. Targeting mutated protein tyrosine kinases and their signaling pathways in hematologic malignancies. Haematologica. 2005; 90:949-968.
6. Lennert K, Parwaresch M R. Mast cells and mast cell neoplasia: a review. Histopathology. 1979; 3:349-365.
7. Metcalfe D D. Classification and diagnosis of mastocytosis: current status. J Invest Dermatol. 1991; 96:2S-4S.
8. Valent P. Biology, classification and treatment of human mastocytosis. Wien Klin Wochenschr. 1996; 108:385-397.
9. Valent P, Akin C, Sperr W R, et al. Diagnosis and treatment of systemic mastocytosis: state of the art. Br J. Haematol. 2003; 122:695-717.

10. Akin C, Metcalfe D D. Systemic mastocytosis. Annu Rev Med. 2004; 55:419-432.
11. Tefferi A, Pardanani A. Clinical, genetic, and therapeutic insights into systemic mast cell disease. Curr Opin Hematol. 2004; 11:58-64.
12. Valent P, Ghannadan M, Akin C, et al. On the way to targeted therapy of mast cell neoplasms: identification of molecular targets in neoplastic mast cells and evaluation of arising treatment concepts. Eur J Clin Invest. 2004; 34:41-52.
13. Nagata H, Worobec A S, Oh C K, et al. Identification of a point mutation in the catalytic domain of the protooncogene c-kit in peripheral blood mononuclear cells of patients who have mastocytosis with an associated hematologic disorder. Proc Natl Acad Sci (USA). 1995; 92:10560-10564.
14. Longley B J, Tyrrell L, Lu S Z, et al. Somatic c-kit activating mutation in urticaria pigmentosa and aggressive mastocytosis: establishment of clonality in a human mast cell neoplasm. Nat. Genet. 1996; 12:312-314.
15. Longley B J, Metcalfe D D, Tharp M, et al. Activating and dominant inactivating c-kit catalytic domain mutations in distinct forms of human mastocytosis. Proc Natl Acad Sci (USA). 1999; 96:1609-1614.
16. Fritsche-Polanz R, Jordan J H, Feix A, et al. Mutation analysis of C-KIT in patients with myelodysplastic syndromes without mastocytosis and cases of systemic mastocytosis. Br J. Haematol. 2001; 113:357-364.
17. Feger F, Ribadeau Dumas A, Leriche L, Valent P, Arock M. Kit and c-kit mutations in mastocytosis: a short overview with special reference to novel molecular and diagnostic concepts. Int Arch Allergy Immunol. 2002; 127:110-114.
18. Furitsu T, Tsujimura T, Tono T, et al. Identification of mutations in the coding sequence of the proto-oncogene c-kit in a human mast cell leukemia cell line causing ligand-independent activation of the c-kit product. J Clin Invest. 1993; 92:1736-1744.
19. Tefferi A, Pardanani A. Systemic mastocytosis: current concepts and treatment advances. Curr Hematol Rep. 2004; 3:197-202.
20. Akin C, Brockow K, D'Ambrosio C, et al. Effects of tyrosine kinase inhibitor STI571 on human mast cells bearing wild-type or mutated forms of c-kit. Exp Hematol 2003; 31:686-692.
21. Ma Y, Zeng S, Metcalfe D D, et al. The c-KIT mutation causing human mastocytosis is resistant to STI571 and other KIT kinase inhibitors; kinases with enzymatic site mutations show different inhibitor sensitivity profiles than wild-type kinases and those with regulatory type mutations. Blood 2002; 99:1741-1744.
22. Frost M J, Ferrao P T, Hughes T P, Ashman L K. Juxtamembrane mutant V5600GKit is more sensitive to Imatinib (STI1571) compared with wild-type c-kit whereas the kinase domain mutant D816VKit is resistant. Mol Cancer Ther. 2002; 1:1115-1124.
23. Akin C, Fumo G, Yavuz A S, Lipsky P E, Neckers L, Metcalfe D D. A novel form of mastocytosis associated with a transmembrane c-kit mutation and response to imatinib. Blood. 2004; 103:3222-3225.
24. Pardanani A, Ketterling R P, Brockman S R, et al. CHIC2 deletion, a surrogate for FIP1L1-PDGFRA fusion, occurs in systemic mastocytosis associated with eosinophilia and predicts response to imatinib mesylate therapy. Blood. 2003; 102:3093-3096.
25. Pardanani A, Elliott M, Reeder T, et al. Imatinib for systemic mast-cell disease. Lancet. 2003; 362:535-536.
26. Pardanani A. Systemic mastocytosis: bone marrow pathology, classification, and current therapies. Acta Haematol. 2005; 114:41-51.
27. Fabbro D, Ruetz S, Bodis S, et al. PKC412-a protein kinase inhibitor with a broad therapeutic potential. Anti-cancer Drug Des. 2000; 15:17-28.
28. Growney J D, Clark J J, Adelsperger J, et al. Activation mutations of human c-KIT resistant to imatinib are sensitive to the tyrosine kinase inhibitor PKC412. Blood. 2005; 106:721-724.
29. Gotlib J, Berube C, Growney J D, et al. Activity of the tyrosine kinase inhibitor PKC412 in a patient with mast cell leukemia with the D816V KIT mutation. Blood. 2005; 106:2865-2870.
30. Gleixner K V, Mayerhofer M, Aichberger K J, et al. The tyrosine kinase-targeting drug PKC412 inhibits in vitro growth of neoplastic human mast cells expressing the D816V-mutated variant of kit: comparison with AMN107, imatinib, and cladribine (2CdA), and evaluation of cooperative drug effects. Blood 2006; 752-759.
31. Weisberg E, Manley P W, Breitenstein W, et al. Characterization of AMN107, a selective inhibitor of native and mutant Bcr-Abl. Cancer Cell. 2005; 7:129-141.
32. von Bubnoff N, Gorantla S H, Kancha R K, Lordick F, Peschel C, Duyster J. The systemic mastocytosis-specific activating cKit mutation D816V can be inhibited by the tyrosine kinase inhibitor AMN107. Leukemia. 2005; 19:1670-1671.
33. Shah N P, Tran C, Lee F Y, Chen P, Norris D, Sawyers C L. Overriding imatinib resistance with a novel ABL kinase inhibitor. Science. 2004; 305:399-401.
34. Shah N P, Lee F Y, Luo R, Jiang Y, Donker M, Akin C. Dasatinib (BMS-354825) inhibits KITD816V, an imatinib-resistant activating mutation that triggers neoplastic growth in the majority of patients with systemic mastocytosis. Blood, in press. 2006.
35. Schittenhelm M M, Shiraga S, Schroeder A, et al. Dasatinib (BMS-354825), a dual SRC/ABL kinase inhibitor, inhibits the kinase activity of wild-type, juxtamembrane, and activation loop mutant KIT isoforms associated with human malignancies. Cancer Res. 2006; 66:473-481.
36. Butterfield J H, Weiler D, Dewald G, Gleich G J. Establishment of an immature mast cell line from a patient with mast cell leukemia. Leuk Res. 1988; 12:345-355.
37. Sillaber C, Strobl H, Bevec D, et al. IL-4 regulates c-kit proto-oncogene product expression in human mast and myeloid progenitor cells. J. Immunol. 1991; 147:4224-4228.
38. Mayerhofer M, Aichberger K J, Florian S, et al. c-kit D816V provides a strong signal for myelomastocytic differentiation and cluster formation in murine Ba/F3 cells. Blood. 2004; 104:141a.
39. Daley G Q, Baltimore D. Transformation of an interleukin 3-dependent hematopoietic cell line by the chronic myelogenous leukemia-specific P210bcr/abl protein. Proc Natl Acad Sci (USA). 1988; 85:9312-9316.
40. Sillaber C, Gesbert F, Frank D A, Sattler M, Griffin J D. STAT5 activation contributes to growth and viability in Bcr/Abl-transformed cells. Blood. 2000; 95:2118-2125.
41. Valent P, Horny H-P, Escribano L, et al. Diagnostic criteria and classification of mastocytosis: a consensus proposal. Conference Report of "Year 2000 Working Conference on Mastocytosis". Leuk Res. 2001; 25:603-625.
42. Valent P, Horny H-P, Li C Y, et al. Mastocytosis (Mast cell disease). World Health Organization (WHO) Classification of Tumours. Pathology & Genetics. Tumours of Haematopoietic and Lymphoid Tissues. eds: Jaffe E S, Harris N L, Stein H, Vardiman J W. 2001; 1:291-302.
43. Bühring H J, Ashman L K, Gattei V, et al. Stem-cell factor receptor (p145(c-kit)) summary report (CD117). in Leucocyte Typing V. White Cell Differentiation Antigens. eds: Schlossmann S F, Boumsell L, Gilks W, et al. Vol 2. pp 1882-1888. Oxford University Press. 1995.

44. Chou T C, Talalay P. Quantitative analysis of dose-effect relationships: the combined effects of multiple drugs or enzyme inhibitors. Adv Enzyme Regul. 1984; 22:27-55.
45. Van Cruchten S, Van Den Broeck W. Morphological and biochemical aspects of apoptosis, oncosis and necrosis. Anat Histol Embryol. 2002; 31:214-223.
46. Schedle A, Samorapoompichit P, Füreder W, et al. Metal ion-induced toxic histamine release from human basophils and mast cells. J Biomed Mater Res. 1998; 39:560-567.
47. Samorapoompichit P, Kiener H P, Schemthaner G H, et al. Detection of tryptase in cytoplasmic granules of basophils in patients with chronic myeloid leukemia and other myeloid neoplasms. Blood. 2001; 98:2580-2583.
48. Escribano L, Orfao A, Diaz-Agustin B, et al. Indolent systemic mast cell disease in adults: immunophenotypic characterization of bone marrow mast cells and its diagnostic implications. Blood. 1998; 91:2731-2736.
49. Escribano L, Diaz-Agustin B, Bellas C, et al. Utility of flow cytometric analysis of mast cells in the diagnosis and classification of adult mastocytosis. Leuk Res. 2001; 25:563-570.
50. Valent P, Schernthaner G H, Sperr W R, et al. Variable expression of activation-linked surface antigens on human mast cells in health and disease. Immunol Rev. 2001; 179:74-81.
51. Schemthaner G H, Hauswirth A W, Baghestanian M, et al. Detection of differentiation- and activation-linked cell surface antigens on cultured mast cell progenitors. Allergy. 2005; 60:1248-1255.
52. Weisberg E, Griffin J D. Resistance to imatinib (Glivec): update on clinical mechanisms. Drug Resist Updat. 2003; 6:231-238.
53. Daub H, Specht K, Ullrich A. Strategies to overcome resistance to targeted protein kinase inhibitors. Nat Rev Drug Discov. 2004; 3:1001-1010.
54. Kluin-Nelemans H C, Oldhoff J M, Van Doormaal J J, et al. Cladribine therapy for systemic mastocytosis. Blood 2003; 102:4270-4276.

What is claimed is:

1. A method of treating a mast cell-related proliferative disease, comprising administering a compound of formula (I):

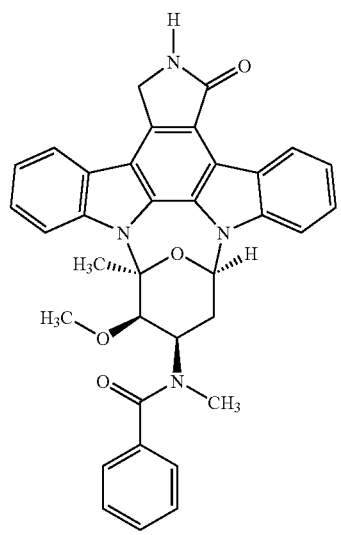

or a pharmaceutically acceptable salt thereof, in combination with a compound of formula (II):

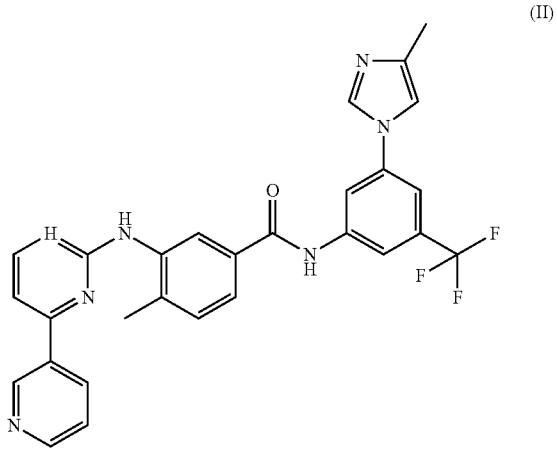

or pharmaceutically acceptable salts thereof.

2. The method according to claim 1 where the mast cell-related proliferative disease is systemic mastocytosis.

3. The method of claim 2, wherein the systemic mastocytosis has resistance to imatinib.

4. The method according to claim 1 wherein the systemic mastocytosis is associated with the oncogenic KIT-D816V mutation.

5. A method for treating mammals suffering from systemic mastocytosis comprising administering to a mammal in need of such treatment a KIT-activity inhibiting amount of a compound of formula (I):

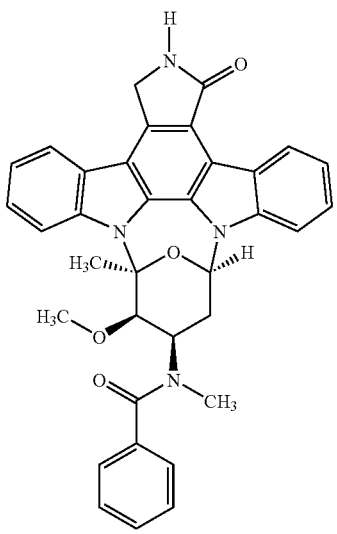

or a pharmaceutically acceptable salt thereof, in combination with a compound of formula (II):

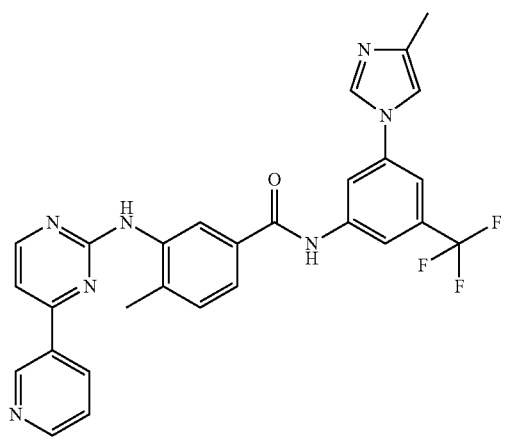

or pharmaceutically acceptable salts thereof.

6. A method for treating mammals, including man, suffering from systemic mastocytosis comprising administering to a mammal in need of such treatment a compound of formula (I):

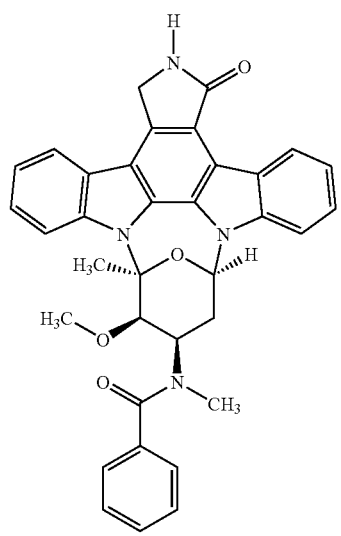

or a pharmaceutically acceptable salt thereof, in combination with a compound of formula (II):

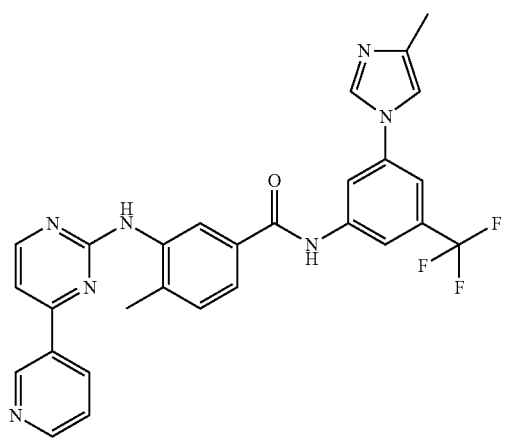

or pharmaceutically acceptable salts thereof.

7. A method of treating a mast cell-related proliferative disease, comprising administering a compound of formula (I):

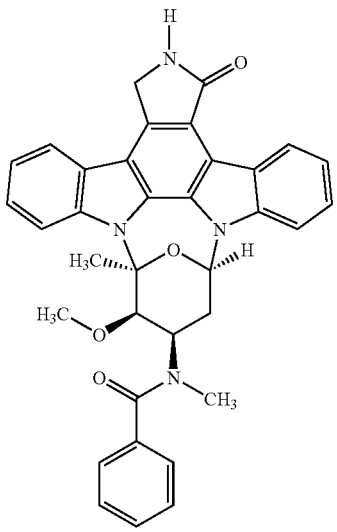

or a pharmaceutically acceptable salt thereof, in combination with a tyrosine kinase (TK) inhibitor selected from dasatinib and 2CdA;
or pharmaceutically acceptable salts thereof.

8. A method of treating systemic mastocytosis, comprising administering a compound of formula (I):

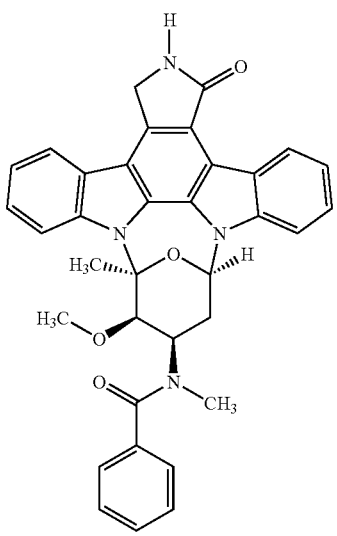

or a pharmaceutically acceptable salt thereof, in combination with a tyrosine kinase (TK) inhibitor selected from dasatinib and 2CdA,
or a pharmaceutically acceptable salt thereof.

9. The method according to claim 7 wherein the mast cell-related proliferative disease is selected from systemic mastocytosis, aggressive systemic mastocytosis and mast cell leukemia.

10. The method according to claim 7 where the mast cell-related proliferative disease has resistance to imatinib.

11. The method according to claim 7 for the treatment of a mast cell-related proliferative disease associated with wild type KIT or with an oncogenic KIT G560V or KIT-D816V mutation.

12. A method for treating mammals suffering from a mast cell-related proliferative disease comprising administering to a mammal in need of such treatment a KIT-activity inhibiting amount of a compound of formula (I):

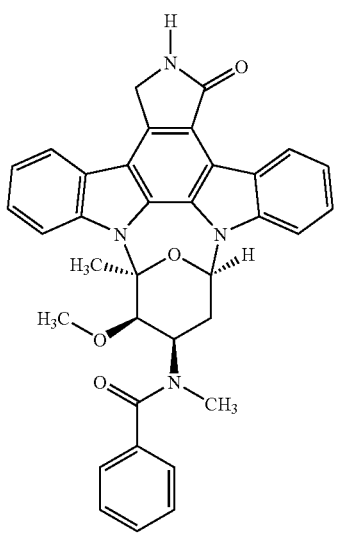

(I)

or a pharmaceutically acceptable salt thereof, in combination with a tyrosine kinase (TK) inhibitor, selected from dasatinib and 2CdA or pharmaceutically acceptable salts thereof.

13. The method according to claim 12 wherein the mast cell-related proliferative disease is selected from systemic mastocytosis, aggressive systemic mastocytosis and mast cell leukemia.

14. The method according to claim 12 where the mast cell-related proliferative disease has resistance to imatinib.

15. The method according to claim 12 for the treatment of a mast cell-related proliferative disease associated with wild type KIT or with an oncogenic KIT G560V or KIT-D816V mutation.

* * * * *